(12) United States Patent
Kendale et al.

(10) Patent No.: US 8,932,208 B2
(45) Date of Patent: Jan. 13, 2015

(54) APPARATUS AND METHODS FOR PERFORMING MINIMALLY-INVASIVE SURGICAL PROCEDURES

(75) Inventors: Amar Kendale, San Francisco, CA (US); Juan I. Perez, San Jose, CA (US); Fred Villagomez, Livermore, CA (US); Frederick Barrigar, Cupertino, CA (US); Joseph N. Lamberti, Castro Valley, CA (US); Amit Agarwal, San Francisco, CA (US); Peter Callas, Castro Valley, CA (US); Michael C. Stewart, Milpitas, CA (US); Arthur Lin, Fremont, CA (US); Ryan Abbott, San Jose, CA (US); Alfredo Cantu R., Pleasanton, CA (US)

(73) Assignee: MAQUET Cardiovascular LLC, Mahwah, NJ (US)

( * ) Notice: Subject to any disclaimer, the term of this patent is extended or adjusted under 35 U.S.C. 154(b) by 799 days.

(21) Appl. No.: 11/544,897

(22) Filed: Oct. 7, 2006

(65) Prior Publication Data

US 2007/0129719 A1     Jun. 7, 2007

Related U.S. Application Data

(63) Continuation-in-part of application No. 11/138,950, filed on May 26, 2005, now abandoned.

(51) Int. Cl.
| | |
|---|---|
| *A61B 1/06* | (2006.01) |
| *A61B 1/313* | (2006.01) |
| *A61B 1/012* | (2006.01) |
| *A61B 1/018* | (2006.01) |

(Continued)

(52) U.S. Cl.
CPC ............ *A61B 1/313* (2013.01); *A61B 1/00096* (2013.01); *A61B 1/00101* (2013.01); *A61B 1/0125* (2013.01); *A61B 1/018* (2013.01); *A61B 18/18* (2013.01); *A61B 2017/00243* (2013.01)
USPC ............ 600/176; 600/114; 600/127; 600/129

(58) Field of Classification Search
USPC ......... 600/105, 114, 127, 132, 153, 170, 171, 600/172, 175, 178, 129, 157, 176
See application file for complete search history.

(56) References Cited

U.S. PATENT DOCUMENTS 3,294,085 A * 12/1966 Wallace ........................ 600/134
3,862,627 A    1/1975 Hans, Sr.

(Continued)

FOREIGN PATENT DOCUMENTS

| EP | 1 181 896 | 2/2002 |
|---|---|---|
| EP | 1 639 936 A1 | 3/2006 |

(Continued)

OTHER PUBLICATIONS

Argenziano., Surgical Atrial Fibrillation Ablation. http://www.columbiasurgery.org/divisions/cardiac/afib_surg.html. pp. 1-4, Downloaded Jan. 13, 2005.

(Continued)

*Primary Examiner* — Alireza Nia

(57) ABSTRACT

Devices, tools and methods for performing minimally invasive surgical procedures. Methods of performing minimally invasive ablation procedures. Methods of performing rapid exchange of tools in a device while the device remains in a reduced-access surgical space.

197 Claims, 37 Drawing Sheets

(51) Int. Cl.
  *A61B 1/00* (2006.01)
  *A61B 1/04* (2006.01)
  *A61B 18/18* (2006.01)
  *A61B 17/00* (2006.01)

(56) References Cited

U.S. PATENT DOCUMENTS

| | | |
|---|---|---|
| 3,970,103 A | 7/1976 | McKee |
| 4,132,227 A * | 1/1979 | Ibe ............................... 600/105 |
| 4,316,472 A | 2/1982 | Mirowski et al. |
| 4,411,266 A | 10/1983 | Cosman |
| 4,449,528 A | 5/1984 | Auth et al. |
| 4,522,205 A | 6/1985 | Taylor et al. |
| 4,569,801 A | 2/1986 | Molley et al. |
| 4,615,333 A * | 10/1986 | Taguchi ........................ 600/171 |
| 4,641,649 A | 2/1987 | Walinsky et al. |
| 4,660,571 A | 4/1987 | Hess et al. |
| 4,662,368 A | 5/1987 | Hussein et al. |
| 4,669,469 A | 6/1987 | Gifford, III et al. |
| 4,672,962 A | 6/1987 | Hershenson |
| 4,673,563 A | 6/1987 | Berne et al. |
| 4,676,258 A | 6/1987 | Inokuchi et al. |
| 4,699,147 A | 10/1987 | Chilson et al. |
| 4,736,749 A | 4/1988 | Lundback |
| 4,757,820 A | 7/1988 | Itoh |
| 4,762,129 A | 8/1988 | Bonzel |
| 4,790,311 A | 12/1988 | Rutz |
| 4,802,475 A | 2/1989 | Weshahy |
| 4,807,620 A | 2/1989 | Strul et al. |
| 4,815,470 A | 3/1989 | Curtis et al. |
| 4,841,977 A | 6/1989 | Griffith et al. |
| 4,872,346 A | 10/1989 | Kelly-Fry et al. |
| 4,882,777 A | 11/1989 | Narula |
| 4,898,591 A | 2/1990 | Jang et al. |
| 4,917,095 A | 4/1990 | Fry et al. |
| 4,924,863 A | 5/1990 | Sterzer |
| 4,936,281 A | 6/1990 | Stasz |
| 4,940,064 A | 7/1990 | Desai |
| 4,945,912 A | 8/1990 | Langberg |
| 4,951,677 A | 8/1990 | Crowley et al. |
| 4,976,711 A | 12/1990 | Parins et al. |
| 4,991,565 A * | 2/1991 | Takahashi et al. ............ 600/123 |
| 4,991,578 A | 2/1991 | Cohen |
| 4,998,933 A | 3/1991 | Eggers et al. |
| 5,000,185 A | 3/1991 | Yock |
| 5,002,059 A | 3/1991 | Crowley et al. |
| 5,035,694 A | 7/1991 | Kasprzyk et al. |
| 5,078,717 A | 1/1992 | Parins et al. |
| 5,078,736 A | 1/1992 | Behl |
| 5,080,102 A | 1/1992 | Dory |
| 5,090,958 A | 2/1992 | Sahota |
| 5,104,393 A | 4/1992 | Isner et al. |
| 5,108,390 A | 4/1992 | Potosky et al. |
| 5,131,397 A | 7/1992 | Crowley |
| 5,147,355 A | 9/1992 | Friedman et al. |
| 5,156,157 A | 10/1992 | Valenta, Jr. et al. |
| 5,178,618 A | 1/1993 | Kandarpa |
| 5,186,177 A | 2/1993 | O'Donnell et al. |
| 5,190,540 A | 3/1993 | Lee |
| 5,193,525 A * | 3/1993 | Silverstein et al. ........... 600/125 |
| 5,195,990 A | 3/1993 | Weldon |
| 5,209,229 A | 5/1993 | Gilli |
| 5,222,501 A | 6/1993 | Ideker et al. |
| 5,224,943 A | 7/1993 | Goddard |
| 5,226,430 A | 7/1993 | Spears et al. |
| 5,228,442 A | 7/1993 | Imran |
| 5,231,995 A | 8/1993 | Desai |
| 5,246,438 A | 9/1993 | Langberg |
| 5,254,116 A | 10/1993 | Baust et al. |
| 5,255,679 A | 10/1993 | Imran |
| 5,263,493 A | 11/1993 | Avitall |
| 5,269,291 A | 12/1993 | Carter |
| 5,277,201 A | 1/1994 | Stern |
| 5,281,215 A | 1/1994 | Milder |
| 5,292,321 A | 3/1994 | Lee |
| 5,293,868 A | 3/1994 | Nardella |
| 5,293,869 A | 3/1994 | Edwards et al. |
| 5,295,484 A | 3/1994 | Marcus et al. |
| 5,311,859 A * | 5/1994 | Monroe et al. ................ 600/112 |
| 5,313,943 A | 5/1994 | Houser et al. |
| 5,314,466 A | 5/1994 | Stern et al. |
| 5,320,091 A * | 6/1994 | Grossi et al. .................. 600/104 |
| 5,323,781 A | 6/1994 | Ideken et al. |
| 5,324,184 A | 6/1994 | Morey |
| 5,324,255 A | 6/1994 | Passafaro et al. |
| 5,324,304 A * | 6/1994 | Rasmussen .................... 606/200 |
| 5,325,860 A | 7/1994 | Seward et al. |
| 5,331,966 A | 7/1994 | Bennett et al. |
| 5,342,292 A | 8/1994 | Nita et al. |
| 5,344,435 A | 9/1994 | Turner et al. |
| 5,345,936 A | 9/1994 | Pomeranz et al. |
| 5,345,940 A | 9/1994 | Seward et al. |
| 5,348,554 A | 9/1994 | Imran et al. |
| 5,368,035 A | 11/1994 | Hamm et al. |
| 5,368,557 A | 11/1994 | Nita et al. |
| 5,368,558 A | 11/1994 | Nita |
| 5,370,678 A | 12/1994 | Edwards et al. |
| 5,372,138 A | 12/1994 | Crowley et al. |
| 5,385,148 A | 1/1995 | Lesh et al. |
| 5,385,544 A | 1/1995 | Edwards et al. |
| 5,391,197 A | 2/1995 | Burdett et al. |
| 5,405,346 A | 4/1995 | Grundy et al. |
| 5,409,000 A | 4/1995 | Imran |
| 5,411,524 A | 5/1995 | Rahul |
| 5,421,338 A | 6/1995 | Crowley et al. |
| 5,423,808 A | 6/1995 | Edwards et al. |
| 5,423,811 A | 6/1995 | Imran et al. |
| 5,427,119 A | 6/1995 | Swartz et al. |
| 5,433,708 A | 7/1995 | Nichols et al. |
| 5,437,664 A | 8/1995 | Cohen et al. |
| 5,447,509 A | 9/1995 | Mills et al. |
| 5,449,380 A | 9/1995 | Chin |
| 5,454,373 A | 10/1995 | Kager et al. |
| 5,456,682 A | 10/1995 | Edwards et al. |
| 5,474,530 A | 12/1995 | Passafaro et al. |
| 5,484,400 A | 1/1996 | Edwards et al. |
| 5,486,155 A * | 1/1996 | Muller et al. .................. 600/137 |
| 5,487,385 A | 1/1996 | Avitall |
| 5,487,757 A | 1/1996 | Truckai et al. |
| 5,496,312 A | 3/1996 | Klicek |
| 5,496,346 A | 3/1996 | Horzewski et al. |
| 5,497,119 A | 3/1996 | Tedrow et al. |
| 5,497,774 A | 3/1996 | Swartz et al. |
| 5,500,012 A | 3/1996 | Brucker et al. |
| 5,501,227 A | 3/1996 | Yock |
| 5,505,702 A | 4/1996 | Arney |
| 5,505,730 A | 4/1996 | Edwards |
| 5,509,900 A | 4/1996 | Kirkman |
| 5,520,682 A | 5/1996 | Baust et al. |
| 5,522,873 A | 6/1996 | Jackman et al. |
| 5,536,267 A | 7/1996 | Edwards et al. |
| 5,545,161 A | 8/1996 | Imran |
| 5,545,193 A | 8/1996 | Fleischman et al. |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,558,672 A | 9/1996 | Edwards et al. |
| 5,558,720 A | 9/1996 | Sarraf et al. |
| 5,560,362 A | 10/1996 | Sliwa, Jr. et al. |
| 5,562,696 A * | 10/1996 | Nobles et al. ................. 606/185 |
| 5,562,720 A | 10/1996 | Stern et al. |
| 5,564,440 A | 10/1996 | Swartz et al. |
| 5,569,241 A | 10/1996 | Edwards |
| 5,571,088 A | 11/1996 | Lennox et al. |
| 5,571,159 A | 11/1996 | Alt |
| 5,571,215 A | 11/1996 | Sternman et al. |
| 5,573,493 A * | 11/1996 | Sauer et al. .................... 600/121 |
| 5,575,766 A | 11/1996 | Swartz et al. |
| 5,575,772 A | 11/1996 | Lennox |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |

(56) References Cited

U.S. PATENT DOCUMENTS

| | | |
|---|---|---|
| 5,588,432 A | 12/1996 | Crowley |
| 5,590,657 A | 1/1997 | Cain et al. |
| 5,595,183 A | 1/1997 | Swanson et al. |
| 5,606,974 A | 3/1997 | Castellano et al. |
| 5,607,422 A | 3/1997 | Smeets et al. |
| 5,607,462 A | 3/1997 | Imran |
| 5,609,606 A | 3/1997 | O'Boyle |
| 5,617,854 A | 4/1997 | Munsif |
| 5,620,479 A | 4/1997 | Diederich |
| 5,630,782 A | 5/1997 | Adair |
| 5,630,837 A | 5/1997 | Crowley |
| 5,637,090 A | 6/1997 | McGee et al. |
| 5,642,736 A | 7/1997 | Avitall |
| 5,643,197 A | 7/1997 | Brucker et al. |
| 5,645,082 A | 7/1997 | Sung et al. |
| 5,656,029 A | 8/1997 | Imran et al. |
| 5,658,278 A | 8/1997 | Imran et al. |
| 5,666,954 A | 9/1997 | Chapelon et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | LaFontaine |
| 5,678,550 A | 10/1997 | Bassen et al. |
| 5,680,860 A | 10/1997 | Imran |
| 5,681,278 A | 10/1997 | Igo et al. |
| 5,681,308 A | 10/1997 | Edwards et al. |
| 5,683,445 A | 11/1997 | Swoyer |
| 5,685,322 A | 11/1997 | Sung et al. |
| 5,685,839 A | 11/1997 | Edwards et al. |
| 5,685,878 A | 11/1997 | Falwell et al. |
| 5,687,723 A | 11/1997 | Avitall |
| 5,687,729 A | 11/1997 | Schaetzle |
| 5,688,267 A | 11/1997 | Panescu et al. |
| 5,690,611 A | 11/1997 | Swartz et al. |
| 5,693,078 A | 12/1997 | Desai et al. |
| 5,697,925 A | 12/1997 | Taylor |
| 5,697,927 A | 12/1997 | Imran et al. |
| 5,697,928 A | 12/1997 | Walcott et al. |
| 5,702,438 A | 12/1997 | Avitall |
| 5,713,942 A | 2/1998 | Stern et al. |
| 5,715,818 A | 2/1998 | Swartz et al. |
| 5,716,389 A | 2/1998 | Walinsky et al. |
| 5,718,231 A | 2/1998 | Dewhurst et al. |
| 5,718,241 A | 2/1998 | Ben-Haim et al. |
| 5,718,701 A | 2/1998 | Shai et al. |
| 5,720,775 A | 2/1998 | Larnard |
| 5,722,401 A | 3/1998 | Pietroski et al. |
| 5,722,403 A | 3/1998 | McKee et al. |
| 5,722,963 A | 3/1998 | Lurie et al. |
| 5,725,494 A | 3/1998 | Brisken |
| 5,725,512 A | 3/1998 | Swartz et al. |
| 5,728,062 A | 3/1998 | Brisken |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,733,315 A | 3/1998 | Burdette et al. |
| 5,735,280 A | 4/1998 | Sherman et al. |
| 5,735,290 A | 4/1998 | Sterman et al. |
| 5,735,811 A | 4/1998 | Brisken |
| 5,735,846 A | 4/1998 | Panescu et al. |
| 5,741,249 A | 4/1998 | Moss et al. |
| 5,741,320 A | 4/1998 | Thornton et al. |
| 5,743,870 A | 4/1998 | Edwards |
| 5,743,903 A | 4/1998 | Stern et al. |
| 5,749,880 A | 5/1998 | Banas et al. |
| 5,755,663 A | 5/1998 | Larsen et al. |
| 5,755,664 A | 5/1998 | Rubenstein |
| 5,755,715 A | 5/1998 | Stern et al. |
| 5,755,760 A | 5/1998 | Maguire et al. |
| 5,769,846 A | 6/1998 | Edwards et al. |
| 5,782,239 A | 7/1998 | Webster et al. |
| 5,782,828 A | 7/1998 | Chen et al. |
| 5,782,900 A | 7/1998 | de la Rama et al. |
| 5,785,706 A | 7/1998 | Bednarek |
| RE35,880 E | 8/1998 | Waldman et al. |
| 5,797,877 A | 8/1998 | Hamilton et al. |
| 5,797,903 A | 8/1998 | Swanson et al. |
| 5,797,905 A | 8/1998 | Fleisahman et al. |
| 5,797,960 A | 8/1998 | Stevens et al. |
| 5,800,378 A | 9/1998 | Edwards et al. |
| 5,800,379 A | 9/1998 | Edwards |
| 5,800,413 A | 9/1998 | Swartz et al. |
| 5,800,428 A | 9/1998 | Nelson et al. |
| 5,800,429 A | 9/1998 | Edwards |
| 5,800,432 A | 9/1998 | Swanson |
| 5,800,482 A | 9/1998 | Pomeranz et al. |
| 5,800,494 A | 9/1998 | Campbell et al. |
| 5,807,249 A | 9/1998 | Qin et al. |
| 5,807,308 A | 9/1998 | Edwards |
| 5,807,391 A | 9/1998 | Wijkamp |
| 5,807,395 A | 9/1998 | Mulier et al. |
| 5,810,802 A | 9/1998 | Panescu et al. |
| 5,824,046 A | 10/1998 | Smith et al. |
| 5,827,216 A | 10/1998 | Igo et al. |
| 5,836,947 A | 11/1998 | Fleischman et al. |
| 5,840,030 A | 11/1998 | Ferek-Petric et al. |
| 5,842,984 A | 12/1998 | Avitall |
| 5,844,349 A | 12/1998 | Oakley et al. |
| 5,846,218 A | 12/1998 | Brisken et al. |
| 5,849,028 A | 12/1998 | Chen |
| 5,851,232 A | 12/1998 | Lois |
| 5,853,409 A | 12/1998 | Swanson et al. |
| 5,871,523 A | 2/1999 | Fleischman et al. |
| 5,871,525 A | 2/1999 | Edwards et al. |
| 5,873,845 A | 2/1999 | Cline et al. |
| 5,876,399 A | 3/1999 | Chia et al. |
| 5,879,295 A | 3/1999 | Li et al. |
| 5,879,296 A | 3/1999 | Ockuly et al. |
| 5,882,346 A | 3/1999 | Pomeranz et al. |
| 5,885,278 A | 3/1999 | Fleischman |
| 5,891,134 A | 4/1999 | Goble et al. |
| 5,893,848 A | 4/1999 | Negus et al. |
| 5,895,417 A | 4/1999 | Pomeranz et al. |
| 5,897,554 A | 4/1999 | Chia et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,916,214 A | 6/1999 | Cosio et al. |
| 5,921,924 A | 7/1999 | Avitall |
| 5,921,982 A | 7/1999 | Lesh et al. |
| 5,927,284 A | 7/1999 | Borst et al. |
| 5,928,191 A | 7/1999 | Houser et al. |
| 5,928,279 A | 7/1999 | Shannon et al. |
| 5,931,810 A | 8/1999 | Grabek |
| 5,931,848 A | 8/1999 | Saadat |
| 5,938,660 A | 8/1999 | Swartz et al. |
| 5,954,661 A | 9/1999 | Greenspon et al. |
| 5,971,980 A | 10/1999 | Sherman |
| 5,971,983 A | 10/1999 | Lesh |
| 5,993,447 A | 11/1999 | Blewett et al. |
| 6,004,269 A | 12/1999 | Crowley et al. |
| 6,006,755 A | 12/1999 | Edwards |
| 6,007,499 A | 12/1999 | Martin et al. |
| 6,012,457 A | 1/2000 | Lesh |
| 6,024,740 A | 2/2000 | Lesh et al. |
| 6,030,379 A | 2/2000 | Panescu et al. |
| 6,042,556 A | 3/2000 | Beach et al. |
| 6,053,912 A | 4/2000 | Panescu et al. |
| 6,056,744 A | 5/2000 | Panescu et al. |
| 6,064,902 A | 5/2000 | Haissaguerre et al. |
| 6,071,233 A * | 6/2000 | Ishikawa et al. ............... 600/104 |
| 6,071,279 A | 6/2000 | Whayne et al. |
| 6,071,281 A | 6/2000 | Burnside et al. |
| 6,076,012 A | 6/2000 | Swanson et al. |
| 6,088,894 A | 7/2000 | Oakley et al. |
| 6,113,592 A | 9/2000 | Taylor |
| 6,117,101 A | 9/2000 | Diederich et al. |
| 6,120,496 A | 9/2000 | Whayne et al. |
| 6,138,043 A | 10/2000 | Avitall |
| 6,142,932 A * | 11/2000 | Morizumi ............... 600/166 |
| 6,142,994 A | 11/2000 | Swanson et al. |

(56) References Cited

U.S. PATENT DOCUMENTS

| | | |
|---|---|---|
| 6,152,920 A | 11/2000 | Thompson et al. |
| 6,161,543 A | 12/2000 | Cox et al. |
| 6,179,835 B1 | 1/2001 | Panescu et al. |
| 6,217,528 B1 | 4/2001 | Koblish et al. |
| 6,217,576 B1 | 4/2001 | Tu et al. |
| 6,231,518 B1 | 5/2001 | Grabek et al. |
| 6,237,605 B1 | 5/2001 | Vaska et al. |
| 6,238,347 B1 | 5/2001 | Nix et al. |
| 6,241,754 B1 | 6/2001 | Swanson et al. |
| 6,245,062 B1 | 6/2001 | Beruke et al. |
| 6,245,064 B1 | 6/2001 | Lesh et al. |
| 6,245,065 B1 | 6/2001 | Panescu et al. |
| 6,251,109 B1 | 6/2001 | Hassett et al. |
| 6,254,599 B1 | 7/2001 | Lesh et al. |
| 6,264,670 B1 | 7/2001 | Chin |
| 6,270,471 B1 | 8/2001 | Hechel et al. |
| 6,277,113 B1 | 8/2001 | Berube |
| 6,277,137 B1 | 8/2001 | Chin |
| 6,293,943 B1 | 9/2001 | Panescu et al. |
| 6,296,619 B1 | 10/2001 | Brisken et al. |
| 6,302,880 B1 | 10/2001 | Schaer |
| 6,308,091 B1 | 10/2001 | Avitall |
| 6,311,692 B1 | 11/2001 | Vaska et al. |
| 6,312,383 B1 | 11/2001 | Lizzi et al. |
| 6,312,427 B1 | 11/2001 | Berube et al. |
| 6,314,962 B1 | 11/2001 | Vaska et al. |
| 6,314,963 B1 | 11/2001 | Vaska et al. |
| 6,325,796 B1 | 12/2001 | Berube et al. |
| 6,325,797 B1 | 12/2001 | Stewart et al. |
| 6,332,881 B1 | 12/2001 | Carner et al. |
| 6,352,503 B1 * | 3/2002 | Matsui et al. .................. 600/104 |
| 6,358,197 B1 * | 3/2002 | Silverman et al. ............. 600/29 |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,375,654 B1 | 4/2002 | McIntyre |
| 6,383,151 B1 | 5/2002 | Diederich et al. |
| 6,383,182 B1 | 5/2002 | Berube et al. |
| 6,385,472 B1 | 5/2002 | Hall et al. |
| 6,387,044 B1 * | 5/2002 | Tachibana et al. ............. 600/114 |
| 6,398,792 B1 | 6/2002 | O'Connor |
| 6,413,254 B1 | 7/2002 | Hissong et al. |
| 6,419,648 B1 | 7/2002 | Vitek et al. |
| 6,421,556 B2 | 7/2002 | Swanson |
| 6,425,867 B1 | 7/2002 | Vaezy et al. |
| 6,428,537 B1 | 8/2002 | Swanson et al. |
| 6,428,556 B1 | 8/2002 | Chin et al. |
| 6,430,426 B2 | 8/2002 | Avitall |
| 6,447,507 B1 | 9/2002 | Bednarek et al. |
| 6,461,314 B1 | 10/2002 | Pant et al. |
| 6,461,956 B1 | 10/2002 | Hsuan et al. |
| 6,464,700 B1 | 10/2002 | Koblish et al. |
| 6,471,696 B1 | 10/2002 | Berube et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,179 B1 | 11/2002 | Wang et al. |
| 6,477,396 B1 | 11/2002 | Most et al. |
| 6,478,029 B1 | 11/2002 | Boyd et al. |
| 6,484,727 B1 | 11/2002 | Vaska et al. |
| 6,494,211 B1 | 12/2002 | Boyd et al. |
| 6,500,174 B1 | 12/2002 | Maguire et al. |
| 6,506,200 B1 | 1/2003 | Chin |
| 6,514,249 B1 | 2/2003 | Maguire et al. |
| 6,517,536 B2 | 2/2003 | Hooven et al. |
| 6,522,930 B1 | 2/2003 | Schaer et al. |
| 6,527,767 B2 | 3/2003 | Wang et al. |
| 6,527,768 B2 | 3/2003 | Berube |
| 6,527,769 B2 | 3/2003 | Langberg et al. |
| 6,529,756 B1 | 3/2003 | Phan et al. |
| 6,546,935 B2 | 4/2003 | Hooven |
| 6,547,788 B1 | 4/2003 | Maguire et al. |
| 6,551,303 B1 | 4/2003 | Van Tassel et al. |
| 6,569,082 B1 | 5/2003 | Chin |
| 6,572,612 B2 | 6/2003 | Stewart et al. |
| 6,582,425 B2 | 6/2003 | Simpson |
| 6,595,989 B1 | 7/2003 | Schaer |
| 6,599,288 B2 | 7/2003 | Maguire et al. |
| 6,607,502 B1 | 8/2003 | Maguire et al. |
| 6,607,520 B2 | 8/2003 | Keane |
| 6,610,055 B1 | 8/2003 | Swanson et al. |
| 6,635,054 B2 | 10/2003 | Fjield et al. |
| 6,645,202 B1 | 11/2003 | Pless et al. |
| 6,652,515 B1 | 11/2003 | Maguire et al. |
| 6,652,518 B2 | 11/2003 | Wellman et al. |
| 6,666,858 B2 | 12/2003 | Lafontaine |
| 6,673,068 B1 | 1/2004 | Berube |
| 6,679,269 B2 | 1/2004 | Swanson |
| 6,689,128 B2 | 2/2004 | Sliwa, Jr. et al. |
| 6,696,844 B2 | 2/2004 | Wong et al. |
| 6,701,931 B2 | 3/2004 | Sliwa, Jr. et al. |
| 6,706,052 B1 | 3/2004 | Chin |
| 6,719,755 B2 | 4/2004 | Sliwa, Jr. et al. |
| 6,728,563 B2 | 4/2004 | Rashidi |
| 6,802,840 B2 | 10/2004 | Chin et al. |
| 6,817,999 B2 | 11/2004 | Berube et al. |
| 6,823,218 B2 | 11/2004 | Berube |
| 6,849,075 B2 | 2/2005 | Bertolero et al. |
| 7,435,248 B2 * | 10/2008 | Taimisto et al. ................. 606/41 |
| 2001/0025174 A1 | 9/2001 | Daniel et al. |
| 2001/0031961 A1 | 10/2001 | Hooven |
| 2002/0017306 A1 | 2/2002 | Cox et al. |
| 2002/0032440 A1 | 3/2002 | Hooven et al. |
| 2002/0056460 A1 * | 5/2002 | Boyd et al. ..................... 128/898 |
| 2002/0068924 A1 | 6/2002 | Sinofsky |
| 2002/0068970 A1 | 6/2002 | Cox et al. |
| 2002/0087151 A1 | 7/2002 | Mody et al. |
| 2002/0087208 A1 | 7/2002 | Koblish et al. |
| 2002/0091382 A1 | 7/2002 | Hooven |
| 2002/0091383 A1 | 7/2002 | Hooven |
| 2002/0091384 A1 | 7/2002 | Hooven et al. |
| 2002/0103484 A1 | 8/2002 | Hooven |
| 2002/0107513 A1 | 8/2002 | Hooven |
| 2002/0107514 A1 | 8/2002 | Hooven |
| 2002/0107530 A1 | 8/2002 | Sauer et al. |
| 2002/0115993 A1 | 8/2002 | Hooven |
| 2002/0120316 A1 | 8/2002 | Hooven et al. |
| 2002/0128636 A1 | 9/2002 | Chin et al. |
| 2002/0143326 A1 | 10/2002 | Foley et al. |
| 2002/0183738 A1 | 12/2002 | Chee et al. |
| 2003/0018329 A1 | 1/2003 | Hooven |
| 2003/0024537 A1 | 2/2003 | Cox et al. |
| 2003/0029462 A1 | 2/2003 | Cox et al. |
| 2003/0032952 A1 | 2/2003 | Hooven |
| 2003/0065318 A1 | 4/2003 | Pendekanti |
| 2003/0065319 A1 | 4/2003 | Wellman |
| 2003/0065320 A1 | 4/2003 | Wellman et al. |
| 2003/0069572 A1 | 4/2003 | Wellman et al. |
| 2003/0069575 A1 | 4/2003 | Chin et al. |
| 2003/0078509 A1 | 4/2003 | Panescu |
| 2003/0083654 A1 | 5/2003 | Chin et al. |
| 2003/0093068 A1 | 5/2003 | Hooven |
| 2003/0109868 A1 | 6/2003 | Chin et al. |
| 2003/0125729 A1 | 7/2003 | Hooven et al. |
| 2003/0163128 A1 | 8/2003 | Patil et al. |
| 2003/0187460 A1 | 10/2003 | Chin et al. |
| 2003/0187461 A1 | 10/2003 | Chin |
| 2003/0191365 A1 * | 10/2003 | Kobayashi ..................... 600/127 |
| 2003/0199867 A1 | 10/2003 | Wellman |
| 2004/0102804 A1 | 5/2004 | Chin |
| 2004/0106918 A1 | 6/2004 | Cox et al. |
| 2004/0111101 A1 | 6/2004 | Chin |
| 2004/0138526 A1 | 7/2004 | Guenst |
| 2004/0216748 A1 | 11/2004 | Chin |
| 2004/0230097 A1 * | 11/2004 | Stefanchik et al. ............ 600/127 |
| 2004/0242963 A1 * | 12/2004 | Matsumoto et al. ........... 600/127 |
| 2004/0267303 A1 | 12/2004 | Guenst |
| 2005/0010201 A1 | 1/2005 | Abboud et al. |

FOREIGN PATENT DOCUMENTS

| | | |
|---|---|---|
| GB | 2 094 636 | 9/1982 |
| GB | 2 289 510 | 11/1995 |

(56) References Cited

FOREIGN PATENT DOCUMENTS

| | | |
|---|---|---|
| WO | WO 93/20770 | 10/1993 |
| WO | WO 93/20886 | 10/1993 |
| WO | WO 94/00050 | 1/1994 |
| WO | WO 94/21167 | 9/1994 |
| WO | WO 94/21168 | 9/1994 |
| WO | WO 94/21665 | 9/1994 |
| WO | WO 95/10318 | 4/1995 |
| WO | WO 95/10319 | 4/1995 |
| WO | WO 95/10321 | 4/1995 |
| WO | WO 95/10978 | 4/1995 |
| WO | WO 95/15115 | 6/1995 |
| WO | WO 95/17222 | 6/1995 |
| WO | WO 95/19738 | 7/1995 |
| WO | WO 95/30380 | 11/1995 |
| WO | WO 96/00036 | 1/1996 |
| WO | WO 96/10961 | 4/1996 |
| WO | WO 96/26675 | 9/1996 |
| WO | WO 96/32885 | 10/1996 |
| WO | WO 96/32897 | 10/1996 |
| WO | WO 96/39966 | 12/1996 |
| WO | WO 97/06727 | 2/1997 |
| WO | WO 97/17904 | 5/1997 |
| WO | WO 97/18853 | 5/1997 |
| WO | WO 97/25916 | 7/1997 |
| WO | WO 97/25918 | 7/1997 |
| WO | WO 97/25919 | 7/1997 |
| WO | WO 97/32525 | 9/1997 |
| WO | WO 97/33526 | 9/1997 |
| WO | WO 97/37607 | 10/1997 |
| WO | WO 97/41793 | 11/1997 |
| WO | WO 97/43970 | 11/1997 |
| WO | WO 97/45156 | 12/1997 |
| WO | WO 98/02201 | 1/1998 |
| WO | WO 98/17187 | 4/1998 |
| WO | WO 98/24488 | 6/1998 |
| WO | WO 98/26724 | 6/1998 |
| WO | WO 98/37822 | 9/1998 |
| WO | WO 98/48881 | 11/1998 |
| WO | WO 98/49957 | 11/1998 |
| WO | WO 98/52465 | 11/1998 |
| WO | WO 99/00064 | 1/1999 |
| WO | WO 99/02096 | 1/1999 |
| WO | WO 99/04696 | 2/1999 |
| WO | WO 99/48421 | 9/1999 |
| WO | WO 99/49788 | 10/1999 |
| WO | WO 99/56812 | 11/1999 |
| WO | WO 99/59486 | 11/1999 |
| WO | WO 00/45706 | 8/2000 |
| WO | WO 00/57495 | 9/2000 |
| WO | WO 0054653 A1 | 9/2000 |
| WO | WO 01/03594 | 1/2001 |
| WO | WO 01/05305 | 1/2001 |
| WO | WO 01/28623 | 4/2001 |
| WO | WO 01/45550 | 6/2001 |
| WO | WO 01/66189 | 9/2001 |
| WO | WO 01/70112 | 9/2001 |
| WO | WO 01/72234 | 10/2001 |
| WO | WO 01/72373 | 10/2001 |
| WO | WO 01/82778 | 11/2001 |
| WO | WO 02/05720 | 1/2002 |
| WO | WO 02/05722 | 1/2002 |
| WO | WO 02/05868 | 1/2002 |
| WO | WO 02/09610 | 2/2002 |
| WO | WO 02/21995 | 3/2002 |
| WO | WO 02/24050 | 3/2002 |
| WO | WO 02/26142 | 4/2002 |
| WO | WO 02/30310 | 4/2002 |
| WO | WO 02/40093 | 5/2002 |
| WO | WO 02/45608 | 6/2002 |
| WO | WO 02/007774 | 10/2002 |
| WO | WO 2005016181 A2 | 2/2005 |

OTHER PUBLICATIONS

Balkhy, et al., Minimally Invasive Atrial Fibrillation Ablation Combined with a New Technique for Thoracoscopic Stapling of the Left Atrial Appendage: Case Report. pp. 1-2, http://www.hsforum.com/vol7/issue 6/2004.html.

Bernbard., Cardiovascular Endoscopy: Historical Perspectives. Chapter 3, pp. 13-30, 1989.

Benussi et al., Surgical Ablation of Trial Fibrillation Using the Epicardial Radiofrequency Approach: Mid-Term Results and Risk Analysis, pp. 1050-1057, 2002.

Cox et al., The Surgical treatment of atrial fibrillation. II. Intraoperative electrophysiologic mapping and description of the electrophysiologic basis of atrial flutter and atrial fibrillation. pp. 406-426, 1991.

Cox et al., The Surgical treatment of atrial fibrillation. III. Development of a definitive surgical procedure. vol. 101, No. 4, pp. 569-583, Apr. 1991.

Cox et al., Current Status of the Maze Procedure for the Treatment of Atrial Fibrillation. vol. 12, No. 1, pp. 15-19, Jan. 2000.

Chen et al., Specialized Conduction Cells in Human Pulmonary Veins: Fact and Controversy. vol. 14, pp. 810-811, Aug. 2003.

Chen et al., Initiation of Atrial Fibrillation by Ectopic Beats Originating From the Pulmonary Veins. pp. 1879-1886, 1999.

Fuster et al., Pathophysiological Mechanisms. vol. 38, pp. 1234-1236, Nov. 2001.

Gaita et al., Atrial Mapping and Radiofrequency Catheter Ablation in Patients with Idiopathic Atrial Fibrillation. pp. 2136-2145, Jun. 2, 1998.

Gillinov et al., Atrial Fibrillation: Current Surgical Options and their Assessment. pp. 2210-2217, 2002.

Gillinov et al., Microwave Ablation of Atrial Fibrillation During Mitral Valve Operations. pp. 1259-1261, 2002.

Gillinov et al., Atricure Bipolar Radiofrequency Clamp for Intraoperative Ablation of Atrial Fibrillation, pp. 2165-2168, 2002.

Guden et al., Intraoperative Saline-Irrigated Radiofrequency Modified Maze Procedure for Atrial Fibrillation. pp. S1301-S1306, 2000.

Haissaguerre et al., Spontaneous Initiation of Atrial Fibrillation by Ectopic Beats Originating in the Pulmonary Veins, vol. 339 No. 10, pp. 659-666, Sep. 3, 1998, downloaded from www.nejm.org.at GUIDANT Corp on Feb. 4, 2004.

Haissaguerre et al., Electrophysiological Breakthroughs from the Left Atrium to the Pulmonary Veins. 2465, (Circulation, 2000; 102: pp. 2463-2465.).

Hammer, et al., "Irrigated Bipolar Radiofrequency Ablation with Transmurality Feedback for the Surgical Cox-Maze Procedure", The Heart Surgery Forum, #2003-11770, 6 (5), 2003.

Hornero, et al., "Biatrial Radiofrequency Ablation for Atrial Fibrillation: Epicardial and Epicardial and Endocardial Surgical Approach", Interactive Cardiovascular and Thoracic Surgery 1 (2002) 72-77.

Kamohara et al., A novel device for left atrial appendage exclusion. The Journal of Thoraicic and Cardiovascular Surgery. vol. 130, No. 6, pp. 1639-1644, Dec. 2005.

Keane et al., Linear Atrial Ablation with a Diode Laser and Fiberoptic Catheter. pp. E59-E60, Oct. 5, 1999.

Keane, et al., "Pulmonary Vein Isolation for Atrial Fibrillation", Review in Cardiovascular Medicine, vol. 3, No. 4, pp. 167-175, 2002.

Kress et al., Validation of a Left Atrial Lesion Pattern for Intraoperative Ablation of Atrial Fibrillation. pp. 1160-1168, 2002.

Kondo et al., Left Atrial Maze Procedure: A Useful Addition to other Corrective Operations. pp. 1490-1494, 2003.

Keane, et al., "Pulmonary Vein Isolation for Atrial Fibrillation", Review in Cardiovascular Medicine, vol. 3, No. 4, 2002.

Levy et al., International Consensus on Nomenclature and Classification of Atril Fibrillation. pp. 443-445, 2003.

Lin et al., Pulmonary Vein Morphology in Patients with Paroxysmal Atril Fibrillation Initiated by Ectopic Beats Originating from the Pulmonary Veins. pp. 1274-1281, Mar. 21, 2000.

Maesseri et al., Beating-Heart Surgical Treatment of Atrial Fibrillation with Microwave Ablation. pp. S1307-S1311, 2002.

Melo et al., Endocardial and epicardial radiofrequency ablation in the treatment of atrial fibrillation with a new Intra-operative device. pp. 182-186, 2000.

Mitchell et al., Linear Atrial Ablations in a Canine Model of Chronic Atrial Fibrillation. pp. 1176-1185, Mar. 31, 1998.

(56) References Cited

OTHER PUBLICATIONS

Mohr et al., Curative treatment of atrial fibrillation with intraoperative radiofrequency ablation: Short-term and midterm results. vol. 123, No. 5, pp. 919-927, 2002.

Natale et al., First Human Experience with Pulmonary Vein Isolation Using a Through-the-Balloon Circumferential Ultrasound Ablation System for Recurrent Atrial Fibrillation. pp. 1879-1882, Oct. 17, 2000. http://www.circulationaha.org.

National Institute for Clinical Excellence, Interventional Procedures Programme. pp. 1-12, Jul. 2004.

L.W. Organ, Electrophysiologic Principles of Radiofrequency Lesion Making. pp. 69-76, 1976.

Pasic et al., Intraoperative Radiofrequency Maze Ablation for Atrial Fibrillation: The Berlin Modification. pp. 1481-1491, 2001.

Saltman et al., A Completely Endoscopic Approch to Microwave Ablation for Atrial Fibrillation. pp. E38-E41. www.hsforum.com/vol6/issue 3/2003-11333.html.

Saltman., Microwave Ablation—A New Use for an Old Technology. pp. 1-8, 2004.

Song et al., Recent Advances in Surgery for Atrial Fibrillation. pp. 1-12, Downloaded Jan. 13, 2005. http://www.ctsnet.org/doc/8509.

Stabile et al., Circulation, Published online before print Aug. 4, 2003, 10.1161/01.CIR.0000086980.42626.34. Is Pulmonary Vein Isolation Necessary for Curing Atrial Fibrillation? http://circ.ahajournals.org/cgi/content/full/108/6/657.

Sueda et al., Efficacy of pulmonary vein isolation for the elimination of chronic atrial fibrillation in cardiac valvular surgery. *Ann Thorac Surg* 2001;71:1189-1193 © 2001 *The Society of Thoracic urgeons*.

Thomas et al., PubMed. Comparison of epicardial and endocardial linear ablation using handheld probes. http://www.ncbi.nlm.nih.gov/entrez/query.fcgi?cmd=Retrieved&db=PubMed&list_uids=12607670&.2003.

Williams et al., Surgical treatment of atrial fibrillation using radiofrequency energy. *Ann Thorac Surg* 2001;71:1939-1944.

Williams et al., Application of Microave Energy in Cardiac Tissue Ablation: From In Vitro Analyses to Clinical Use. *Ann Thorac Surg* 2002;74:1500-1505.

Yufera et al., An Integrated Circuit for Tissue Impedance Measure. pp. 88-93, 2002.

\* cited by examiner

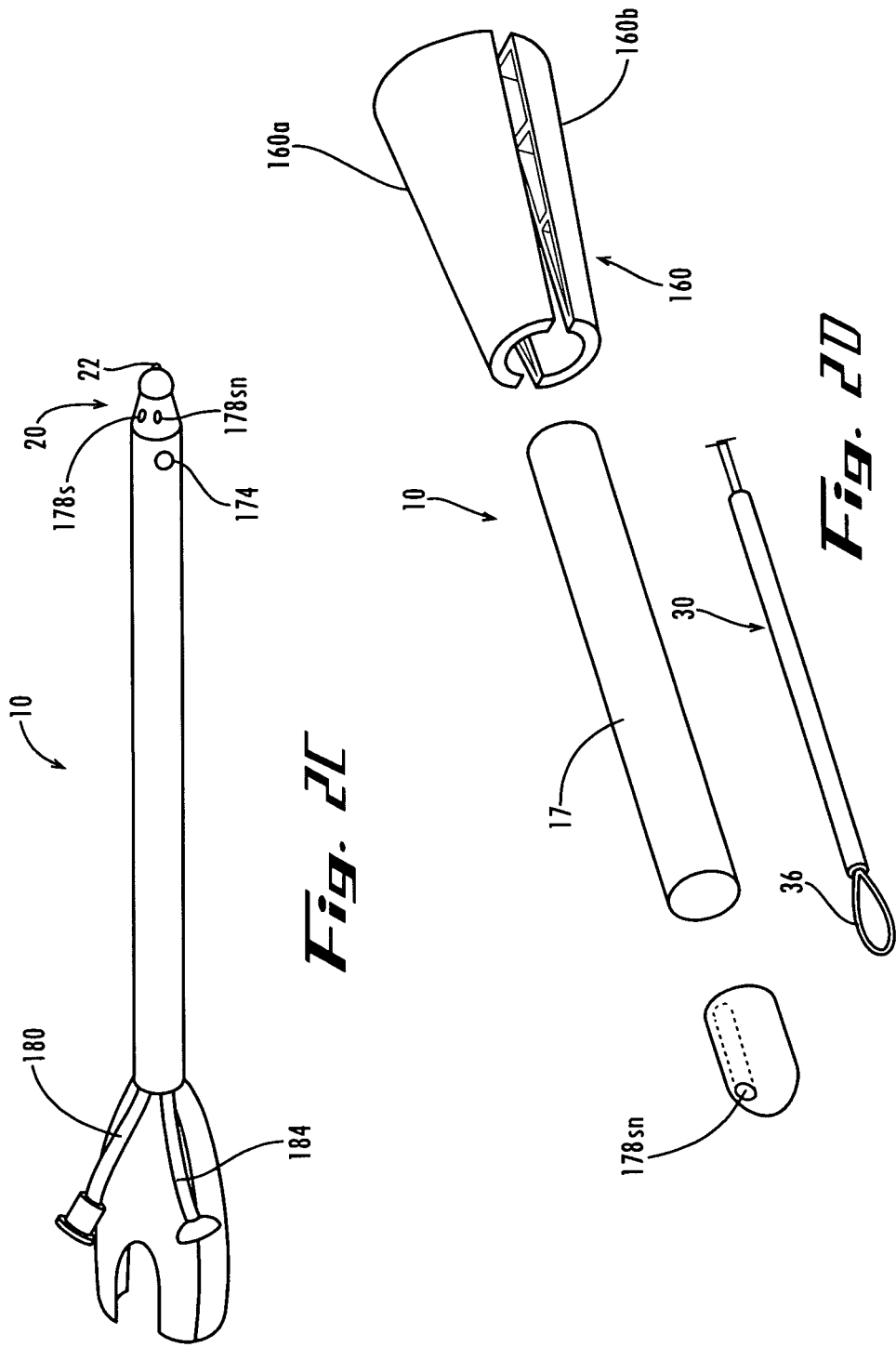

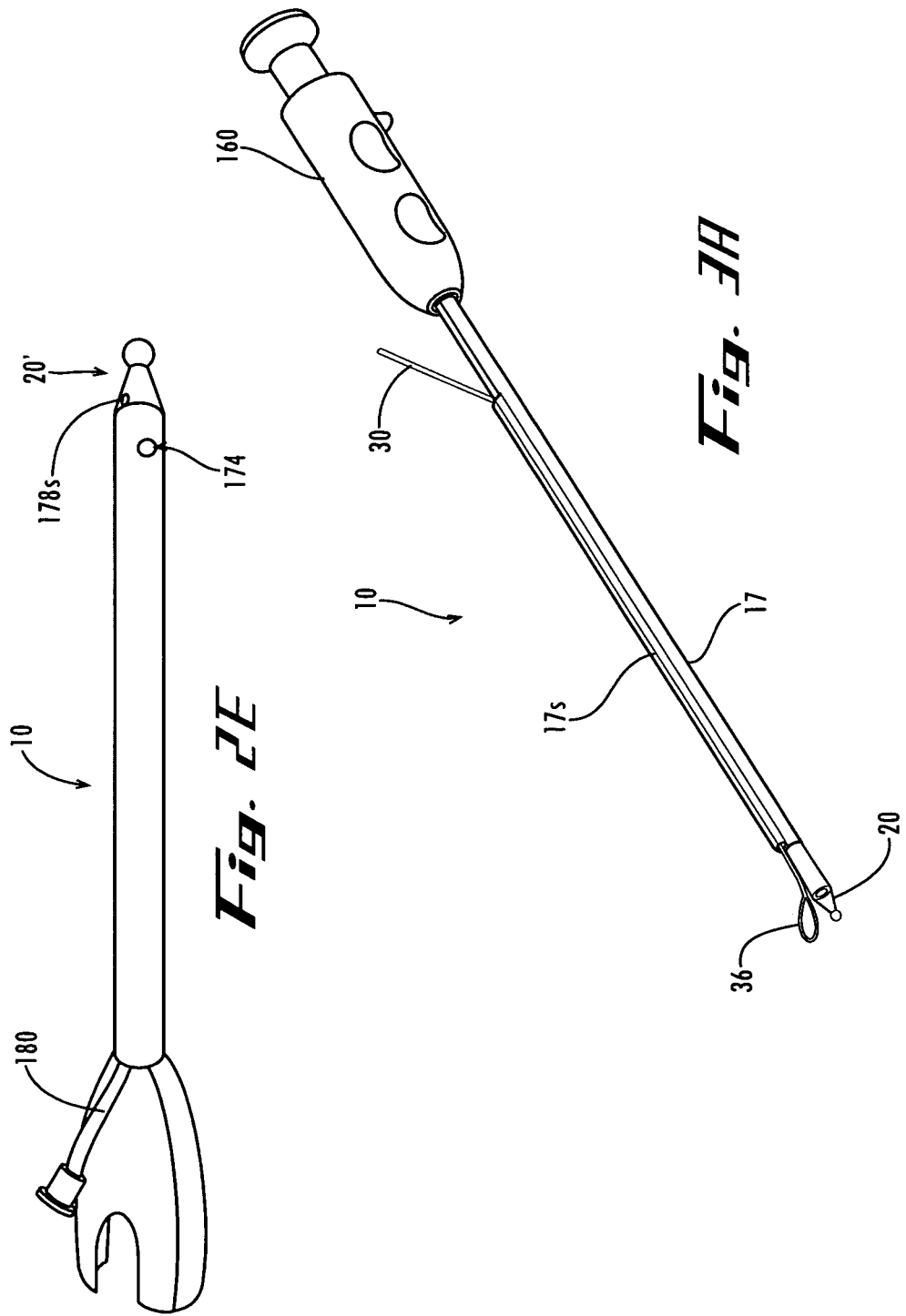

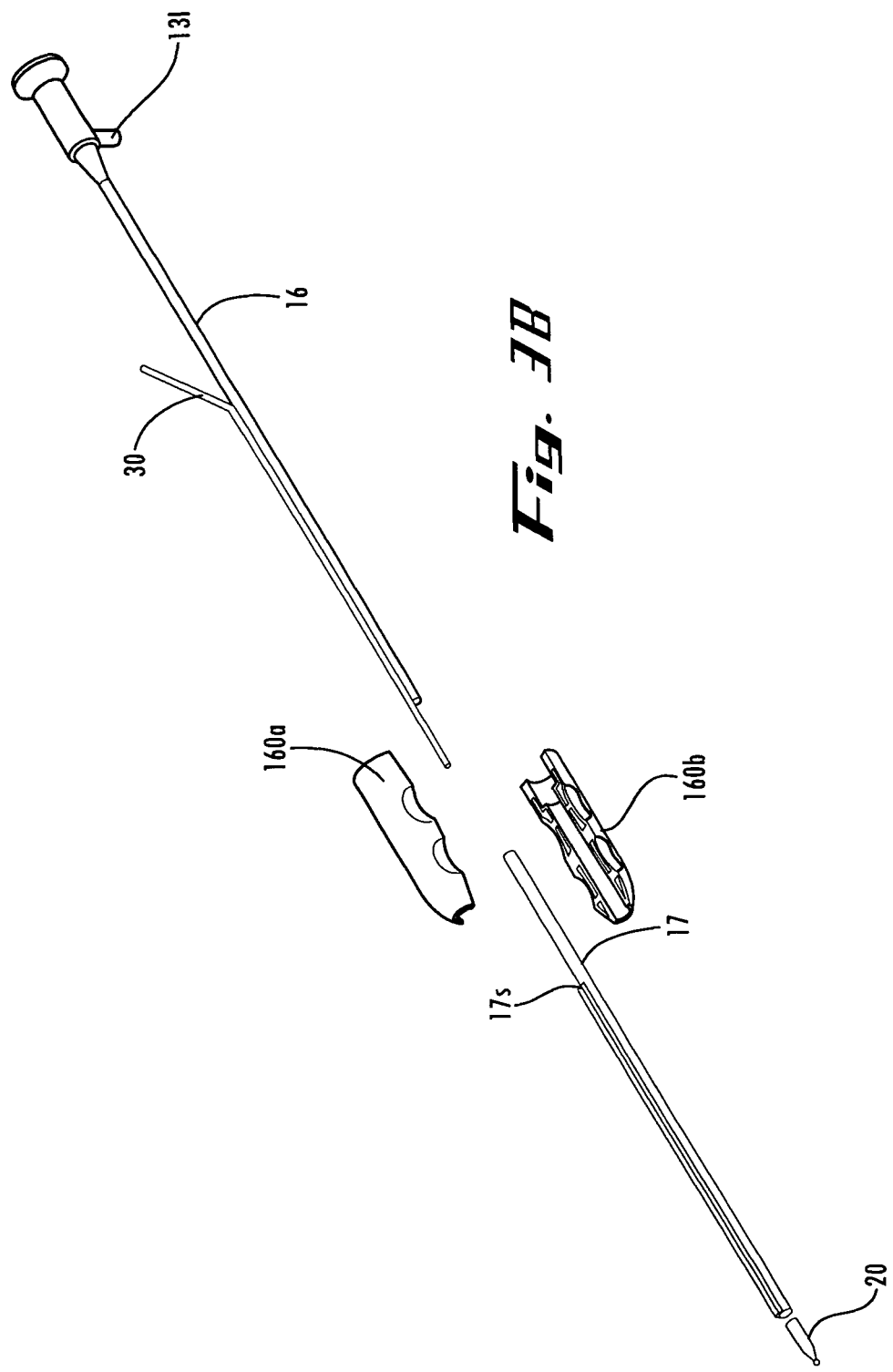

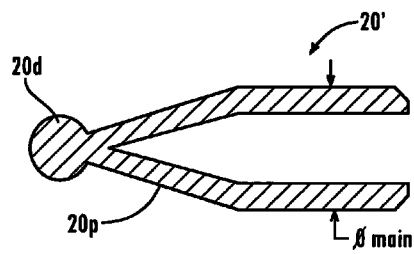
Fig. 4K
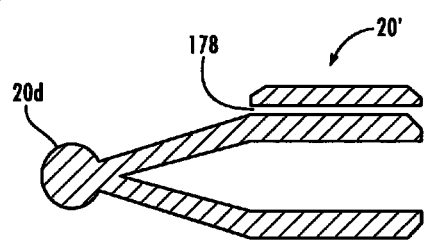
Fig. 4N
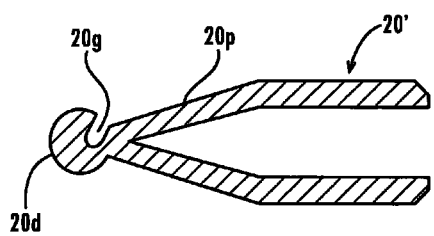
Fig. 4L
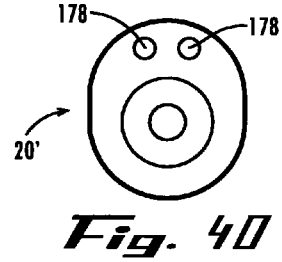
Fig. 4O
Fig. 4M

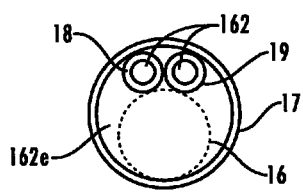
Fig. 6I
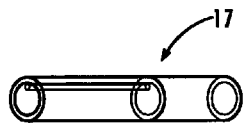
Fig. 6L
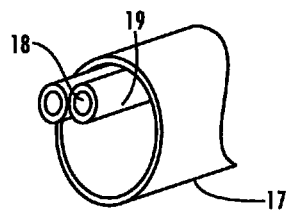
Fig. 6J
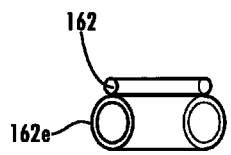
Fig. 6M
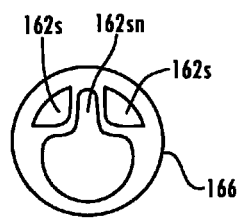
Fig. 6K
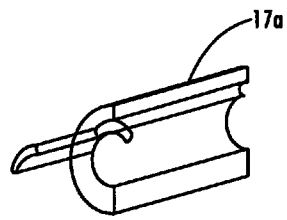
Fig. 6N
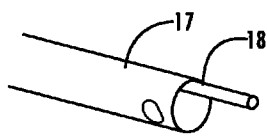
Fig. 6O
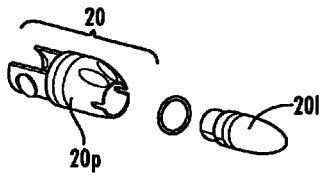

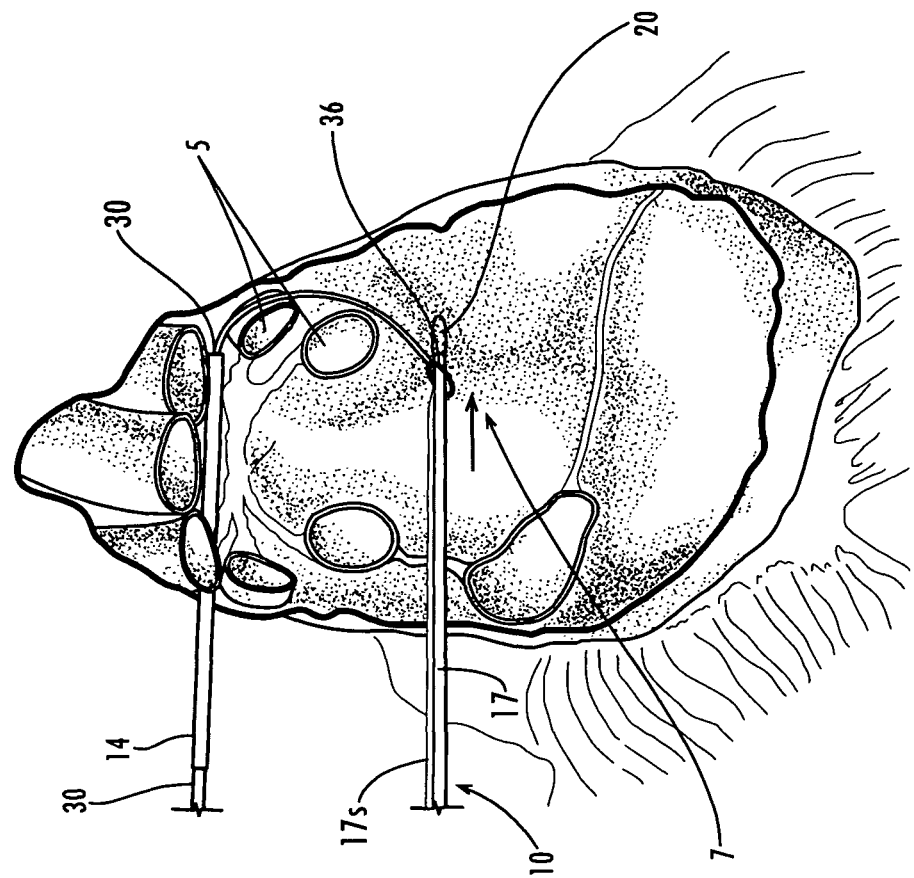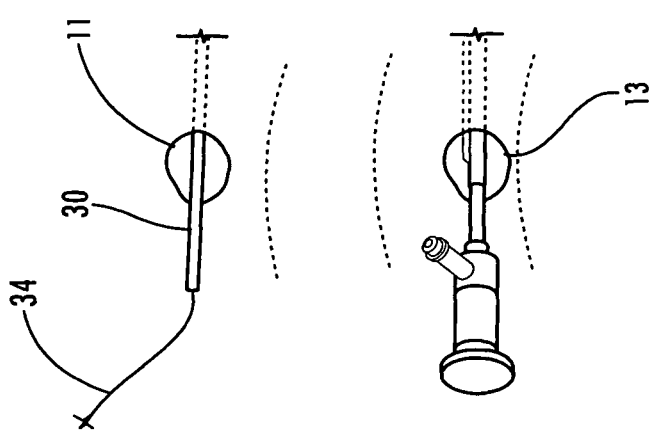
Fig. 12C

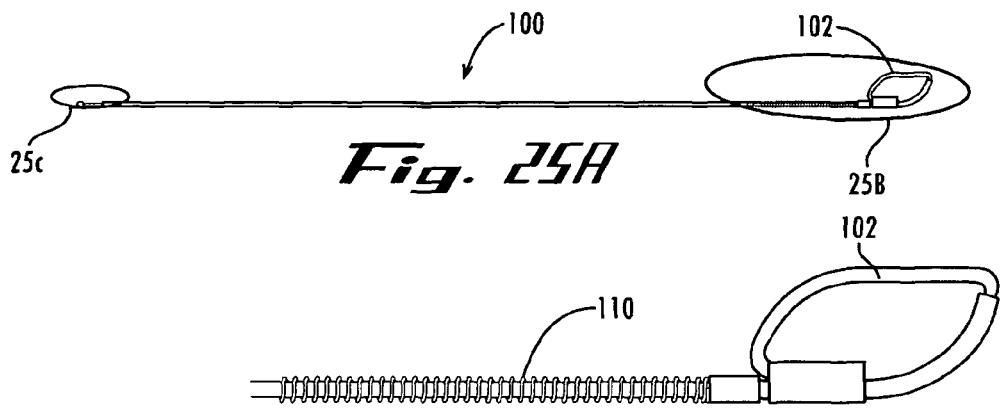
Fig. 25A
Fig. 25B
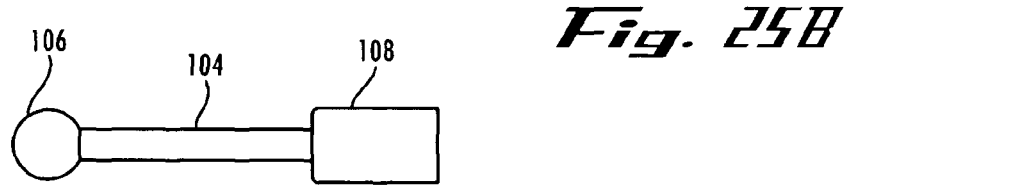
Fig. 25C
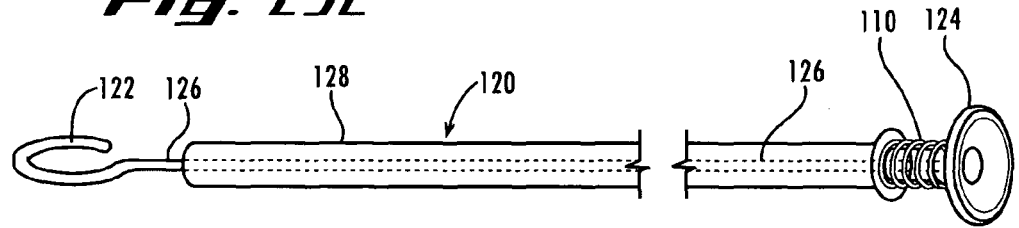
Fig. 26A
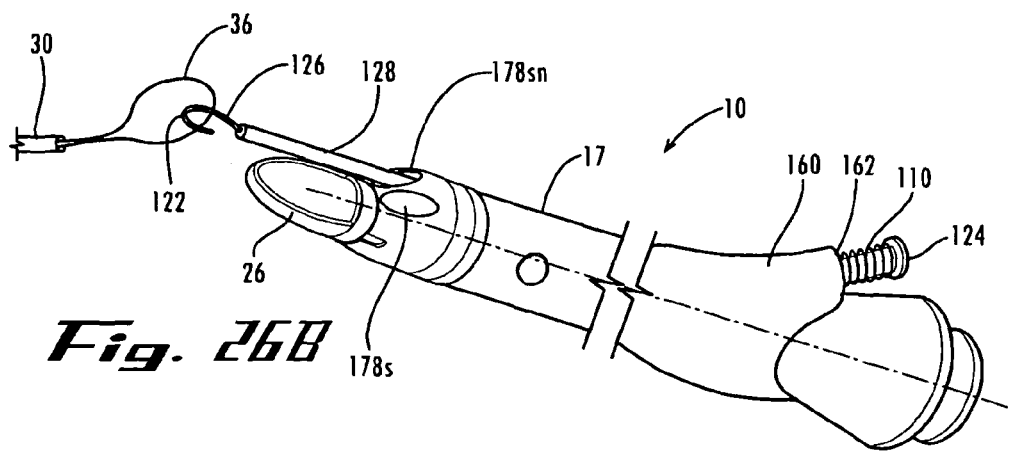
Fig. 26B

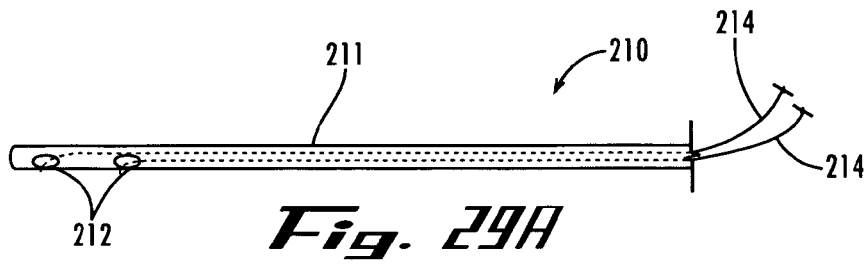
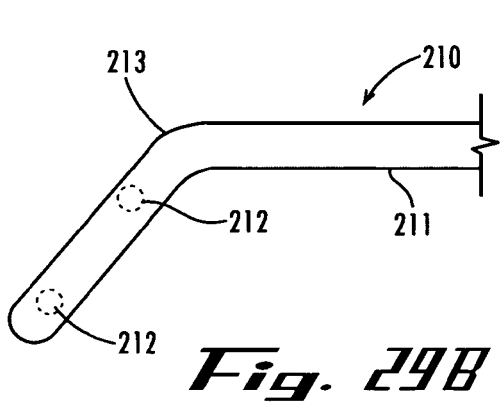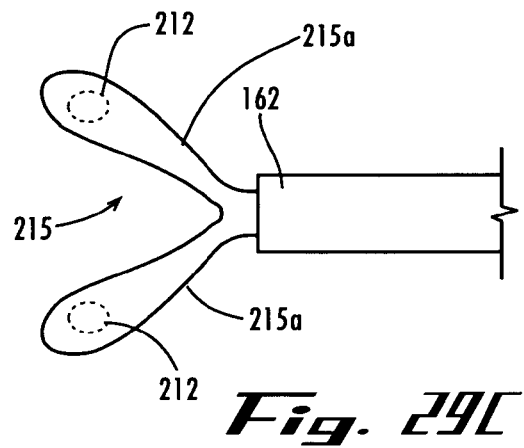
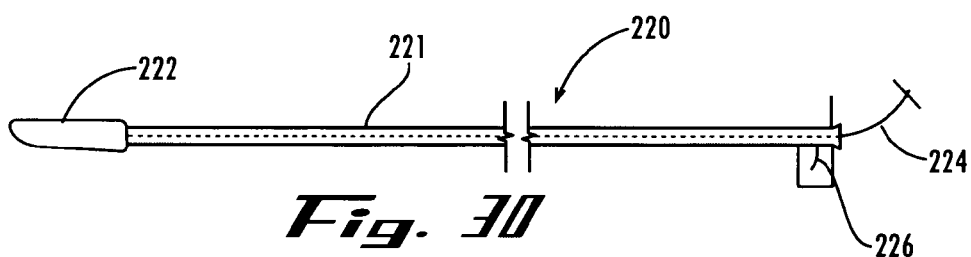
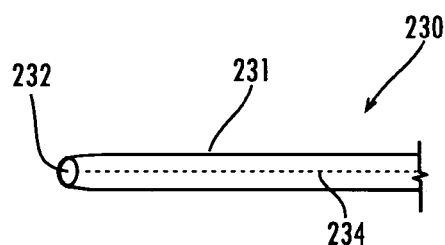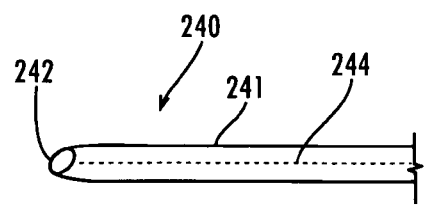

APPARATUS AND METHODS FOR PERFORMING MINIMALLY-INVASIVE SURGICAL PROCEDURES

CROSS-REFERENCE

This application is a continuation-in-part application of U.S. application Ser. No. 11/138,950, filed May 26, 2005, which is incorporated herein by reference in its entirety and to which application we claim priority under 35 USC §120.

FIELD OF THE INVENTION

The field of the present invention is apparatus and methods for performing minimally invasive surgery, more particularly to ablation procedures performed with minimally invasive surgical techniques and apparatus.

BACKGROUND OF THE INVENTION

Various medical conditions, diseases and dysfunctions may be treated by ablation, using various ablation devices and techniques. Ablation is generally carried out to kill or destroy tissue at the site of treatment to bring about an improvement in the medical condition being treated.

In the cardiac field, cardiac arrhythmias, and particularly atrial fibrillation are conditions that have been treated with some success by various procedures using many different types of ablation technologies. Atrial fibrillation continues to be one of the most persistent and common of the cardiac arrhythmias, and may further be associated with other cardiovascular conditions such as stroke, congestive heart failure, cardiac arrest, and/or hypertensive cardiovascular disease, among others. Left untreated, serious consequences may result from atrial fibrillation, whether or not associated with the other conditions mentioned, including reduced cardiac output and other hemodynamic consequences due to a loss of coordination and synchronicity of the beating of the atria and the ventricles, possible irregular ventricular rhythm, atrioventricular valve regurgitation, and increased risk of thromboembolism and stroke.

As mentioned, various procedures and technologies have been applied to the treatment of atrial arrhythmias/fibrillation. Drug treatment is often the first approach to treatment, where it is attempted to maintain normal sinus rhythm and/or decrease ventricular rhythm. However, drug treatment is often not sufficiently effective and further measures must be taken to control the arrhythmia.

Electrical cardioversion and sometimes chemical cardioversion have been used, with less than satisfactory results, particularly with regard to restoring normal cardiac rhythms and the normal hemodynamics associated with such.

A surgical procedure known as the MAZE III (which evolved from the original MAZE procedure) procedure involves electrophysiological mapping of the atria to identify macroreentrant circuits, and then breaking up the identified circuits (thought to be the drivers of the fibrillation) by surgically cutting or burning a maze pattern in the atrium to prevent the reentrant circuits from being able to conduct therethrough. The prevention of the reentrant circuits allows sinus impulses to activate the atrial myocardium without interference by reentering conduction circuits, thereby preventing fibrillation. This procedure has been shown to be effective, but generally requires the use of cardiopulmonary bypass, and is a highly invasive procedure associated with high morbidity.

Other procedures have been developed to perform transmural ablation of the heart wall or adjacent tissue walls. Transmural ablation may be grouped into two main categories of procedures: endocardial and epicardial. Endocardial procedures are performed from inside the wall (typically the myocardium) that is to be ablated, and is generally carried out by delivering one or more ablation devices into the chambers of the heart by catheter delivery, typically through the arteries and/or veins of the patient. Epicardial procedures are performed from the outside wall (typically the myocardium) of the tissue that is to be ablated, often using devices that are introduced through the chest and between the pericardium and the tissue to be ablated. However, mapping may still be required to determine where to apply an epicardial device, which may be accomplished using one or more instruments endocardially, or epicardial mapping may be performed. Various types of ablation devices are provided for both endocardial and epicardial procedures, including radiofrequency (RF), microwave, ultrasound, heated fluids, cryogenics and laser. Epicardial ablation techniques provide the distinct advantage that they may be performed on the beating heart without the use of cardiopulmonary bypass.

When performing procedures to treat atrial fibrillation, an important aspect of the procedure generally is to isolate the pulmonary veins from the surrounding myocardium. The pulmonary veins connect the lungs to the left atrium of the heart, and join the left atrial wall on the posterior side of the heart. When performing open chest cardiac surgery, such as facilitated by a full sternotomy, for example, epicardial ablation may be readily performed to create the requisite lesions for isolation of the pulmonary veins from the surrounding myocardium. Treatment of atrial ablation by open chest procedures, without performing other cardiac surgeries in tandem, has been limited by the substantial complexity and morbidity of the procedure. However, for less invasive procedures, the location of the pulmonary veins creates significant difficulties, as typically one or more lesions are required to be formed to completely encircle these veins.

One example of a less invasive surgical procedure for atrial fibrillation has been reported by Saltman, "A Completely Endoscopic Approach to Microwave Ablation for Atrial Fibrillation", The Heart Surgery Forum, #2003-11333 6 (3), 2003, which is incorporated herein in its entirety, by reference thereto. In carrying out this procedure, the patient is placed on double lumen endotracheal anesthesia and the right lung is initially deflated. Three ports (5 mm port in fifth intercostal space, 5 mm port in fourth intercostal space, and a 10 mm port in the sixth intercostal space) are created through the right chest of the patient, and the pericardium is then dissected to enable two catheters to be placed, one into the transverse sinus and one into the oblique sinus. Instruments are removed from the right chest, and the right lung is re-inflated. Next, the left lung is deflated, and a mirror reflection of the port pattern on the right chest is created through the left chest. The pericardium on the left side is dissected to expose the left atrial appendage and the two catheters having been initially inserted from the right side are retrieved and pulled through one of the left side ports. The two catheter ends are then tied and/or sutured together and are reinserted through the same left side port and into the left chest. The leader of a Flex 10 microwave probe (Guidant Corporation, Santa Clara, Calif.) is sutured to the end of the upper catheter on the right hand side of the patient, and the lower catheter is pulled out of a right side port to pull the Flex 10 into the right chest and lead it around the pulmonary veins. Once in proper position, the Flex 10 is incrementally actuated to form a lesion around the pulmonary veins. The remaining catheter and Flex 10 are then pulled out of the chest and follow-up steps are carried out to close the ports in the patient and complete the surgery.

Although advances have been made to reduce the morbidity of atrial ablation procedures, as noted above, there remains a continuing need for devices, techniques, systems and procedures to further reduce the invasiveness of such procedures, thereby reducing morbidity, as well as potentially reducing the amount of time required for a patient to be in surgery, as well as reducing recovery time.

SUMMARY OF THE INVENTION

Apparatus, devices tools and methods for performing endoscopic surgical procedures are provided where only a minimal number of (or even one) openings are required to perform the procedures. Ablation procedures, including epicardial ablation procedures and apparatus for performing such procedures are described. Epicardial atrial ablation may be performed epicardially with access through only one side of a patient's chest required to perform all procedures.

Surgical device for performing minimally invasive surgical procedures are provided, including an elongated body having distal and proximal end portions and at least two lumens extending generally along a direction of a longitudinal axis of the elongated body; and a distal tip attachable to the distal end portion of the elongated body, the distal tip including a lens that is viewable therethrough and aligned with one of the at least two lumens that is configured for receiving an endoscope therein.

In at least one embodiment, a handle is attached to the proximal end portion of the elongated body. In at least one embodiment, a bell is rotatably attached to the handle.

In at least one embodiment, the elongated body is substantially rigid.

In at least one embodiment, at least one of the at least two lumens other than the lumen configured for receiving an endoscope therein comprises a service port adapted to receive a tool other than an endoscope. In at least one embodiment, two such service ports are provided.

In at least one embodiment, each service port provided comprises a tube received within the elongated body of the device.

In at least one embodiment, each tube extending from a service port comprises a stainless steel hypotube.

In at least one embodiment, an endoscope is positioned in the lumen that is configured for receiving an endoscope therein.

In at least one embodiment, the distal tip of the device comprises at least one lumen therethrough, wherein each lumens of the tip is configured and dimensioned to receive one of the tubes therein and provide an exit opening for a service port through the tip.

In at least one embodiment, a seal is provided between the lens and a portion of the tip proximal to the lens.

In at least one embodiment, a proximal end portion of each tube is securely held by a handle attached to the proximal end portion of the elongated body.

In at least one embodiment, the lens is removably mounted to a remainder of the distal tip via mechanical connection.

In at least one embodiment, the lens is removably mounted to the remainder of the distal tip via at least one of friction fitting and threads.

In at least one embodiment, the lens is fixed to a remainder of the distal tip via adhesive.

In at least one embodiment, the distal tip is fixable to a distal end piece that includes at least one lumen, wherein the distal end piece is mountable to the distal end portion of the elongated body, and wherein the at least one lumen of the distal end piece aligns in communication with respective ones of at least one of the at least two lumens of the elongated body, in fluid communication therewith, to function as at least one service port.

In at least one embodiment, a protrusion extends distally from a distal end of the distal tip.

In at least one embodiment, a snare device extends through one of the at least two lumens, and the snare device includes a snare on a distal end thereof.

In at least one embodiment, the snare device further comprises a snare on a proximal end thereof.

In at least one embodiment, a handle provided on the proximal end portion of the device comprises an open proximal end configured to receive an endoscope therethrough. In at least one embodiment, the handle captures the proximal end portion of the elongated body, thereby preventing axial movement of the elongated body with respect to the handle. In at least one embodiment, the handle allows rotation of the elongated body with respect thereto. In at least one embodiment, the handle prevents rotation of the elongated body with respect thereto.

In at least one embodiment, a recess is provided in a portion of the handle, wherein the recess is configured and dimensioned to receive a light cable that extends from an endoscope, when the endoscope is received in the elongated body.

In at least one embodiment, an insert is mounted within the elongated body, wherein the insert and the elongated body cooperate to define the at least two lumens. In at least one embodiment, the insert forms a friction fit with the elongated body within said elongated body.

In at least one embodiment, a second insert can be provided to be interchanged with the first insert, wherein the second insert and the elongated body cooperate to form lumens having at least one of: a different size, different relative positioning and different number of lumens relative to size, positioning and number of the at least two lumens formed in cooperation between the elongated main body and the first insert.

In at least one embodiment, a second tip is provided that is interchangeable with the first tip, the second tip comprising at least one of: a different size, different relative positioning and different number of lumens relative to size, positioning and number of the at least one lumen formed in the first tip.

In at least one embodiment, the distal tip is axially aligned with the lumen that is configured for receiving the endoscope therein, and at least one of the at least two lumens that is not configured for receiving the endoscope therein is positioned radially outwardly from the lumen that is configured to receive the endoscope therein, such that an implement can be delivered though each lumen positioned radially outward, and a distal end portion of the implement is deliverable alongside the tip.

In at least one embodiment, the distal tip comprises a ball-ended tip.

In at least one embodiment, the distal tip is bullet shaped.

In at least one embodiment, the distal tip comprises a notch configured and dimensioned to receive a portion of a snare therein.

In at least one embodiment, a suction luer is provided in fluid communication with one of the at least two lumens, wherein the suction luer extends from the proximal end portion of the elongated body.

In at least one embodiment, an introducer tube is provided in fluid communication with one of the at least two lumens, wherein the introduce tube extends from the proximal end portion of the elongated body.

In at least one embodiment, the elongated body comprises three lumens, and the device further includes an introducer tube in fluid communication with a lumen other than the lumen configured and adapted to receive an endoscope and the lumen in fluid communication with the suction luer, wherein the introducer tube extends from the proximal end portion of the elongated body.

In at least one embodiment, the tip of the device is releasably attachable to the elongated body. In at least one embodiment, the tip comprises protrusions on a proximal end portion thereof, and the elongated body comprises openings through the walls of the distal end portion thereof, wherein the openings are configured and dimensioned to receive the protrusions.

In at least one embodiment, a suction tube extends through one of the at least two lumens and provides fluid communication between the distal and proximal end portions of the elongated body.

In at least one embodiment, a suction tube extends through one of the at least two lumens and provides fluid communication between the distal tip and the proximal end portion of the elongated body.

In at least one embodiment, the tip of the device includes an inner stop configured to prevent distal advancement of a distal end of the endoscope therepast, to establish an offset between a distal end of the distal tip and the distal end of the endoscope.

In at least one embodiment, a cage is mounted to the distal tip to extend distally therefrom.

In at least one embodiment, the lens of the distal tip comprises an outer lens, and the distal tip further includes an inner tapered lens configured to break up reflections when viewing through the endoscope.

In at least one embodiment, the distal end portion of the elongated body has a first cross-sectional area and the proximal end portion of the elongated body has a second cross-sectional area, wherein the second cross-sectional area is greater than the first cross-sectional area. In at least one embodiment, the distal end portion of the elongated body is teardrop-shaped in cross-section. In at least one embodiment, the proximal end portion of the elongated body is circular in cross-section.

In at least one embodiment, the lumens are formed by metal tubes within the elongated tubular body.

In at least one embodiment, the distal tip of the device comprises at least one inflatable member mounted to a proximal end portion thereof.

In at least one embodiment, a snare capture tool extends through one of the at least two lumens, and has a ball-shaped distal end.

In at least one embodiment, a retrieval hook tool extends through one of the at least two lumens, and has a hook at a distal end thereof.

In at least one embodiment, a bolo tool extends through one of the at least two lumens, and has a ball at a distal end thereof. In at least one embodiment, the bolo tool also has a ball at a proximal end thereof.

In at least one embodiment, a trigger snare tool extends through one of the at least two lumens, the trigger snare tool comprising a snare at a distal end thereof that is extendable distally from the distal end portion of the elongated body, and a trigger configured to actuate the snare, wherein the trigger is located proximally of the proximal end portion of the elongated body.

In at least one embodiment, the snare of the trigger snare tool is angled relative to a longitudinal axis of the trigger snare tool.

In at least one embodiment, a perforation tool extends through one of the at least two lumens, and the perforation tool includes a needle or barbed needle at a distal end thereof, wherein the needle or barbed needle is extendable distally of the distal end portion of the elongated body. In at least one embodiment, the perforation tool further includes a cutter blade, wherein the barbed needle is retractable proximally to draw tissue engaged by the barb needle into contact with the cutter blade.

In at least one embodiment, a perforation tool extends through one of the at least two lumens, wherein the perforation tool comprises graspers adapted to be extended distally to grasp tissue, and a cutter blade, and wherein the graspers are retractable proximally to draw tissue engaged by the graspers into contact with the cutter blade.

In at least one embodiment, a perforation tool extends through one of the at least two lumens, and the perforation tool includes a cork screw adapted to be extended distally to engage tissue, and a cutter blade, wherein the corkscrew is retractable proximally to draw tissue engaged by the corkscrew into contact with the cutter blade.

In at least one embodiment, a perforation tool extends through one of the at least two lumens, and the perforation tool comprises a spike configured to pierce through tissue upon an impulsive impact, and a plunger type actuator located on a proximal end portion of the perforation tool.

In at least one embodiment, a mapping probe tool extends through one of the at least two lumens of the device, and the mapping probe tool includes at least a pair of mapping elements on a distal end portion thereof, wherein the mapping elements are extendable distally of a distal opening of the lumen. In at least one embodiment, the distal end portion of the mapping probe tool is bent at an angle to a longitudinal axis of a remainder of the mapping probe tool when the mapping probe tool is in an unbiased state. In at least one embodiment, the distal end portion of the mapping probe tool is formed in a Y-shape when in an unbiased state, one of the mapping elements being located on one arm of the Y-shape and a second of the mapping elements being located on an arm opposite the one arm.

In at least one embodiment, a linear ablating probe tool extends through one of the at least two lumens, the linear ablating probe tool comprising a linear ablation element on a distal end portion thereof.

In at least one embodiment, a point ablation probe tool extends through one of the at least two lumens, the point ablation probe tool comprising an ablation probe point on a distal tip thereof.

In at least one embodiment, a cautery tool extends through one of the at least two lumens, the cautery tool comprising a cauterizing element on a distal end portion thereof.

In at least one embodiment, graspers extend through one of the at least two lumens, and the graspers include a tube having sufficient length to simultaneously extend from both distal and proximal openings of the lumen, grasping jaws provided at a distal end portion of the graspers, and an actuator located at a proximal end portion of the graspers, wherein the actuator is linked to the grasping jaws for operation thereof.

In at least one embodiment, scissors extend through one of the at least two lumens, wherein the scissors include a tube having sufficient length to simultaneously extend from both distal and proximal openings of the lumen, scissor jaws provided at a distal end portion of the scissors, and an actuator located at a proximal end portion of the scissors, and wherein the actuator is linked to the scissor jaws for operation thereof.

In at least one embodiment, the device further includes an inflatable member that is expandable around a base of the distal tip to achieve a temporary, atraumatic increase in diameter at a distal end portion of the device. In at least one embodiment, a fitting plug is positioned over the elongated body and fixed to the inflatable member for holding the inflatable member in position over the base of the distal tip. In at least one embodiment, a tensioning member interconnects the fitting plug and the inflatable member, and the tensioning member is adjustable to draw the inflatable member into a desired position at the base of the distal tip.

In at least one embodiment, the lumen of the device that is configured for receiving an endoscope therein comprises a positioning feature for positioning the endoscope at more than one predetermined location. In at least one embodiment, the positioning feature comprises biased sockets configured to receive protrusions on the endoscope therein.

In at least one embodiment, the distal tip of the device includes at least one window proximal of a distal end of the distal tip, through which viewing by the endoscope is permitted.

In at least one embodiment, a handle of the device includes proximal and distal stops so that when the endoscope is inserted in the lumen that is configured for receiving an endoscope therein, a light cable of the endoscope abuts the proximal stop for placing the endoscope in one predetermined location relative to the elongated body, and abuts the distal stop for placing the endoscope in a second location relative to the elongated body.

A surgical device for performing minimally invasive surgical procedures is provided, including: a first elongated body having distal and proximal end portions and at least one lumen extending generally along a direction of a longitudinal axis of the first elongated body and configured and dimensioned for receiving an endoscope therein; a second elongated body aligned substantially parallel with the first elongated body, the second elongated body having distal and proximal end portions and at least one lumen extending generally along a direction of a longitudinal axis of the second elongated body and configured and dimensioned for receiving a tool other than the endoscope therein; and a distal tip attachable to the distal end portion of the first elongated body, wherein the distal tip includes a lens that is viewable therethrough and aligned with the lumen that is configured and dimensioned for receiving an endoscope therein. In at least one embodiment, an endoscope is positioned in the lumen that is configured and dimensioned for receiving an endoscope therein.

In at least one embodiment, a handle is attached to the proximal end portion of the first elongated body.

In at least one embodiment, the first and second elongated bodies are substantially rigid.

In at least one embodiment, the second elongated body is fixed externally to the first elongated body. In at least one embodiment, the second elongated body is welded to the first elongated body.

In at least one embodiment, a snare device extends through one of the at least one lumen of the second elongated body, wherein the snare device has a snare on a distal end thereof. In at least one embodiment, the snare device further includes a snare on a proximal end thereof.

In at least one embodiment, the distal tip is attached to the distal end portion of the first elongated body, and a distal end of the endoscope is positioned within the distal tip.

In at least one embodiment, the distal tip comprises a ball-ended tip.

In at least one embodiment, the distal tip is bullet shaped.

In at least one embodiment, the distal tip comprises a notch configured and dimensioned to receive a portion of a snare therein.

In at least one embodiment, a tool other than an endoscope extends through one of the at least one lumens of the second elongated body. In at least one embodiment, the tool is selected from the group consisting of: suction tool, snare capture tool, retrieval hook tool, bolo tool, trigger snare tool, perforation tool, mapping probe tool, linear ablating probe tool, point ablation probe tool, cautery tool, graspers tool, and scissors tool.

A surgical device for performing minimally invasive surgical procedures is provided, including: an elongated body having distal and proximal end portions and at least two lumens extending generally along a direction of a longitudinal axis of the elongated body; and an endoscope positioned in one of the at least two lumens that is configured and dimensioned for receiving the endoscope therein; wherein a distal end of the elongated body extends distally past a distal end of the endoscope to shield the distal end of the endoscope during use.

In at least one embodiment, the distal end of the elongated body is open.

In at least one embodiment, one of the at least one lumens comprises an irrigation lumen. In at least one embodiment, a nozzle is provided at a distal end of the irrigation lumen. In at least one embodiment, the nozzle is oriented toward the distal end of the endoscope. In at least one embodiment, the nozzle is located out of a field of view of the endoscope.

In at least one embodiment, the distal end portion of the elongated body is transparent to allow visualization therethrough.

In at least one embodiment, a snare device extends through one of the at least two lumens of the elongated body, the snare device having a snare on a distal end thereof. In at least one embodiment, the snare device further comprises a snare on a proximal end thereof.

A surgical device for performing minimally invasive surgical procedures is provided, including: an elongated body comprising a semi-flexible sleeve having distal and proximal end portions and at least one lumen extending generally along a direction of a longitudinal axis of said elongated body; and a rigid distal tip attached to a distal end of said elongated body, said distal tip being viewable therethrough.

In at least one embodiment, the sleeve is sufficiently flexible to navigate around pulmonary veins to at least partially encircle the pulmonary veins and the sleeve is sufficiently rigid so that a proximal portion of the sleeve outside of a patient can be pushed on to advance the distal end portion of the sleeve within the patient.

In at least one embodiment, an endoscope is inserted in the sleeve, the endoscope having a rigid shaft and being positioned for viewing through the distal tip.

In at least one embodiment, the distal tip comprises a ball at a distal end thereof.

In at least one embodiment, the distal tip comprises at least one port in fluid communication with the at least one lumen in the elongated body.

A surgical device for performing minimally invasive surgical procedures is provided, including: an elongated body comprising a semi-flexible sleeve having distal and proximal end portions; and a capturing feature extending distally from a distal end of said elongated body.

In at least one embodiment, an endoscope is inserted in the sleeve, wherein the endoscope has a distal tip attached thereto that extends distally of the distal end of the elongated body.

In at least one embodiment, the capturing feature comprises a snare threaded through openings in the distal tip to extend distally therefrom. In at least one embodiment, the elongated body is slidable proximally with respect to the distal tip to cinch down the snare.

In at least one embodiment, the capturing feature comprises a pad of either a hook or a loop portion of a hook and loop type fastening mechanism.

In at least one embodiment, the capturing feature comprises a magnet.

A surgical device for performing minimally invasive surgical procedures is provided, including: an elongated body having distal and proximal end portions and at least two lumens extending generally along a direction of a longitudinal axis of the elongated body, wherein at least one of the lumens comprises a slot opening to an external surface of the elongated body, and the slot is configured and dimensioned to releasably secure a tool therein via friction fit.

In at least one embodiment, the tool comprises a snare catheter.

In at least one embodiment, a distal tip attachable to the distal end portion of the elongated body, wherein the distal tip includes a lens that is viewable therethrough and aligned with one of the at least two lumens that is configured for receiving an endoscope therein.

In at least one embodiment, the slot extends over a majority of a length of the elongated body.

In at least one embodiment, the slot is formed in an eyelet on the distal end portion of the elongated body.

In at least one embodiment, the tool includes a distal end portion having a first outside diameter larger than an outside diameter of a portion of the tool immediately proximal of the distal end portion of the tool, wherein the portion immediately proximal is slidable through the slot, and wherein retraction of the tool being positioned through the slot and into the lumen that the slot opens to, secures the distal end portion in the eyelet.

In at least one embodiment, the slot is formed by a keyed socket on the distal end portion of the elongated member.

In at least one embodiment, the at least one lumen having a slot is asymmetrical in cross-section and forms a cam surface permitting the tool to be rotated into the at least one lumen having a slot.

A surgical device for performing minimally invasive surgical procedures is provided, including: an endoscope having an elongated shaft having distal and proximal end portions; a distal tip attachable to the distal end portion of the endoscope, the distal tip including a lens that is viewable therethrough; and a ring provided over the elongated shaft and axially slidable with respect thereto, the ring being configured and dimensioned to releasably fix a distal end portion of a tool thereto.

In at least one embodiment, the ring comprises a releasable locking mechanism.

In at least one embodiment, the tool comprises a snare catheter.

A surgical device for performing minimally invasive surgical procedures is provided, including: a jig having slots configured and dimensioned to receive and releasably fix an endoscope and at least one tool thereto for rapid exchange procedures.

In at least one embodiment, a pair of such jigs each configured with the slots, is provided.

In at least one embodiment, an endoscope and a snare catheter are each releasably fixed to the jig.

A surgical device for performing minimally invasive surgical procedures is provided, including: a jig having at least one opening configured and dimensioned to receive and releasably fix a tool thereto for rapid exchange procedures; and an opening configured and dimensioned to receive an endoscope therethrough, wherein the endoscope is freely slidable with respect to the jig.

In at least one embodiment, a pair of such jigs are provided.

In at least one embodiment, each jig comprises at least two openings for releasably fixing at least two tools.

In at least one embodiment, an endoscope is slidably received within the jig, and a snare catheter is releasably fixed to the jig.

In at least one embodiment, an endoscope is slidably received within the jig, a snare catheter is releasably fixed to the jig, and a second tool is releasably fixed to the jig. In at least one embodiment, the second tool comprises a suction tube.

A surgical device for performing minimally invasive surgical procedures is provided, including: an elongated body having distal and proximal end portions and configured and dimensioned to receive an endoscope therethrough and to apply suction therethrough; and a distal tip attachable to the distal end portion of the elongated body, the distal tip including a lens that is viewable therethrough, the distal tip having a proximal opening having an outside diameter that is greater than an outside diameter of a distal end of the elongated body, such that a gap is formed between the distal tip and the elongated body when the distal tip is attached to the elongated body, facilitating diffuse application of suction.

In at least one embodiment, struts interconnect the distal tip and the elongated body.

A routing snare tool configured and dimensioned to be slid through a lumen of a device that also receives an endoscope is provided, including: a flexible outer tube having sufficient column strength to advance the tool through the lumen by pushing on a proximal portion of the outer tube from a location outside of the lumen, to advance the tube without buckling; a snare line having a length greater than a length of the flexible outer tube; and a snare loop fixed to an end of the snare line via heat shrink tubing.

In at least one embodiment, a second snare loop is fixed to an opposite end of the snare line via heat shrink tubing.

In at least one embodiment, both ends of the outer tube are chamfered.

In at least one embodiment, the heat shrink tubing is color coded differently with respect to each snare loop to facilitate ready visual distinction between the two snare loops.

In at least one embodiment, the snare loop comprises a kink extending distally from a remainder of the snare loop.

In at least one embodiment, the snare loop is angled, with respect to a longitudinal axis of the snare line, by an angle of less than about thirty degrees.

In at least one embodiment, a lock is configured to fix a position of the snare line relative to the outer tube to maintain the snare loop in a cinched configuration. In at least one embodiment, the lock comprises an actuator configured to move a clamp into contact with the snare line. In at least one embodiment, the lock comprises a pair of locking clasps that are alternatively lockable and releasable by the same actuating movement by a user.

A snare capture tool configured and dimensioned to be slid through a lumen of a device that also receives an endoscope is provided, including: an elongated mandrel configured and dimensioned to be slid through the lumen; a handle fixed to a proximal end of the mandrel; and a ball fixed at a distal end of the mandrel.

In at least one embodiment, a polymeric layer is formed over a majority of the mandrel, wherein a distal end portion of the mandrel extends from a distal end of the polymeric layer and is not covered thereby.

In at least one embodiment, a compressible spring is provided over the polymeric layer, a proximal end portion of the spring abuts the handle, and the spring has a outside diameter larger than an inside diameter of the lumen, thereby being prevented from insertion into the lumen.

In at least one embodiment, the snare capture tool is configured and dimensioned, so that when the spring is compressed against a proximal end of the lumen by advancing the handle distally with respect to the lumen, the ball and at least a portion of the distal portion not covered by the polymeric layer extend distally from a distal end of the lumen, and when a driving force is released from the handle, the spring expands, thereby retracting the ball and the at least a portion of the distal portion not covered by the polymeric layer, into the lumen.

A retrieval hook tool configured and dimensioned to be slid through a lumen of a device that also receives an endoscope is provided, including: an elongated mandrel configured and dimensioned to be slid through the lumen; a handle fixed to a proximal end of the mandrel; and a hook provided at a distal end of the mandrel.

In at least one embodiment, a polymeric layer is formed over a majority of the mandrel, wherein a distal end portion of the mandrel extends from a distal end of the polymeric layer and is not covered thereby.

In at least one embodiment, a compressible spring is provided over the mandrel, a proximal end portion of the spring abutting said handle, said spring having a outside diameter larger than an inside diameter of said lumen, thereby being prevented from insertion into said lumen.

In at least one embodiment, the retrieval hook tool is configured and dimensioned, so that when the spring is compressed against a proximal end of the lumen by advancing the handle distally with respect to the lumen, the hook extends distally from a distal end of the lumen, and when a driving force is released from the handle, the spring expands, thereby retracting the hook into the lumen.

In at least one embodiment, the mandrel is offset in the polymeric layer, such that longitudinal axes of the mandrel and the polymeric layer do not coincide.

A bolo tool configured and dimensioned to be slid through a lumen of a device that also receives an endoscope is provided, including: an elongated mandrel configured and dimensioned to be slid through the lumen; a first ball provided at a proximal end of the mandrel; and a second ball provided at a distal end of the mandrel.

A trigger snare tool and dimensioned to be slid through a lumen of a device that also receives an endoscope is provided, including: an elongated mandrel configured and dimensioned to be slid through the lumen; a snare provided at a distal end of the mandrel; and a snare guide into which the elongated mandrel is slidably received, the snare guide being configured and dimensioned to be slid through the lumen, wherein the snare guide is slidable distally with respect to the mandrel to cinch down the snare.

In at least one embodiment, a handle is provided at a proximal end of the mandrel; a trigger is slidably positioned over the handle and fixed to a proximal end of the snare guide; and a biasing member is provided that biases the trigger distally from the handle.

In at least one embodiment, the snare, when uncinched, is oriented at an acute angle with respect to a longitudinal axis of the mandrel.

A perforation tool configured and dimensioned to be slid through a lumen of a device that also receives an endoscope is provided, including: a perforating member connected to an actuator via an elongated shaft; a sheath configured and dimensioned to be slid through the lumen of the device and to surround the perforating member and the shaft during sliding within the lumen; wherein the actuator is operable to slide the perforating member distally with respect to the sheath to extend the perforating member distally beyond a distal end of the sheath.

In at least one embodiment, the perforating member comprises a needle.

In at least one embodiment, the perforating member comprises a spike.

In at least one embodiment, the perforation tool includes a handle mounted to a proximal portion of the tool, the handle being configured to be mated with a connector of a suction assembly.

In at least one embodiment, a cutting blade is positioned proximally of the perforating member, and the perforating member is configured to engage tissue, wherein the actuator is actuatable to retract the perforating member, after engaging tissue, to draw the tissue against the cutting blade, thereby cutting an opening through the tissue.

In at least one embodiment, a second actuator is provided, wherein the second actuator is linked to the cutting blade and is operable to rotate the cutting blade.

In at least one embodiment, the perforating member comprises a barbed needle.

In at least one embodiment, the perforating member comprises a corkscrew.

In at least one embodiment, the perforating member comprises graspers.

In at least one embodiment, the actuator is further actuatable to open and close the graspers.

A mapping probe tool configured and dimensioned to be slid through a lumen of a device that also receives an endoscope is provided, including: an elongated member configured and dimensioned to be positioned in the lumen and having a length sufficient to extend a proximal end portion of the elongated member from the proximal end of the lumen while a distal end portion extends distally from a distal end of the lumen; wherein the distal end portion includes at least a pair of probe mapping elements, and the probe mapping elements are electrically connectable to a power source located proximally of the tool via at least one electrical wire connected thereto.

In at least one embodiment, a handle is fixed to a proximal end portion of the elongated member; and a biasing member is configured to bias the handle away from the lumen, the biasing member being configured and dimensioned to prevent insertion of the biasing member into the lumen.

In at least one embodiment, the mapping tool is configured and dimensioned, so that when the handle is slid distally with respect to the lumen, thereby biasing the biasing member, the probe mapping elements extend distally from a distal end of the lumen, and when a driving force is released from the handle, the biasing member drives the handle proximally with respect to the lumen, thereby retracting the probe mapping elements into the lumen.

In at least one embodiment, the distal end portion is Y-shaped in an unbiased configuration, with one of each pair of probes being located on opposite ones of open arms of the Y-shape.

In at least one embodiment, the distal end portion is angled to a longitudinal axis of a remainder of the elongated member when the elongated member is in an unbiased configuration.

A linear ablating probe tool configured and dimensioned to be slid through a lumen of a device that also receives an endoscope is provided, including: an elongated member configured and dimensioned to be positioned in the lumen and having a length sufficient to extend a proximal end portion of the elongated member from the proximal end of the lumen while a distal end portion extends distally from a distal end of the lumen; a linear ablation member located at the distal end portion of the elongated member and configured to form a linearly extending lesion in tissue being treated thereby; and at least one ablation conduit connected to the linear ablation member and extending from the linear ablation member to a proximal end portion of the elongated member, a proximal end of each ablation conduit being configured to be connected to a source of ablation energy located proximally of the tool.

In at least one embodiment, an actuator is located on the proximal end portion of the elongated member, the actuator being operable by a user to deliver ablation energy to the linear ablation member.

In at least one embodiment, a handle is fixed to a proximal end portion of the elongated member; and a biasing member is configured to bias the handle away from the lumen, the biasing member being configured and dimensioned to prevent insertion of the biasing member into the lumen.

In at least one embodiment, the linear ablating tool is configured and dimensioned, so that when the handle is slid distally with respect to the lumen, thereby biasing the biasing member, the linear ablation member extends distally from a distal end of the lumen, and when a driving force is released from the handle, the biasing member drives the handle proximally with respect to the lumen, thereby retracting the linear ablation member into the lumen.

A point ablation probe tool configured and dimensioned to be slid through a lumen of a device that also receives an endoscope is provided, including: an elongated member configured and dimensioned to be positioned in the lumen and having a length sufficient to extend a proximal end portion of the elongated member from the proximal end of the lumen while a distal end portion extends distally from a distal end of the lumen; an ablation probe point provided on a distal end of the elongated member and configured to form a point lesion in tissue being treated thereby; and an ablation conduit connected to the ablation probe point and extending from the ablation probe point to a proximal end portion of the elongated member, a proximal end of the ablation conduit being configured to be connected to a source of ablation energy located proximally of the tool.

In at least one embodiment, an actuator is located on the proximal end portion of the elongated member, the actuator being operable by a user to deliver ablation energy to the ablation probe point.

In at least one embodiment, a handle is fixed to a proximal end portion of the elongated member; and a biasing member is configured to bias the handle away from the lumen, the biasing member being configured and dimensioned to prevent insertion of the biasing member into the lumen.

In at least one embodiment, the point ablation probe tool is configured and dimensioned, so that when the handle is slid distally with respect to the lumen, thereby biasing the biasing member, the ablation probe point extends distally from a distal end of the lumen, and when a driving force is released from the handle, the biasing member drives the handle proximally with respect to the lumen, thereby retracting the ablation probe point into the lumen.

A cautery tool configured and dimensioned to be slid through a lumen of a device that also receives an endoscope is provided, including: an elongated member configured and dimensioned to be positioned in the lumen and having a length sufficient to extend a proximal end portion of the elongated member from the proximal end of the lumen while a distal end portion extends distally from a distal end of the lumen; a cauterizing element provided on a distal end of the elongated member and configured to cauterize tissue; and an electrical wire connected to the cauterizing element and extending from the cauterizing element to a proximal end portion of the elongated member, a proximal end of the electrical wire being configured to be connected to a power source located proximally of the tool.

In at least one embodiment, an actuator is located on the proximal end portion of the elongated member, the actuator being operable by a user to deliver energy to the cauterizing element.

In at least one embodiment, a handle is fixed to a proximal end portion of the elongated member; and a biasing member is configured to bias the handle away from the lumen, the biasing member being configured and dimensioned to prevent insertion of the biasing member into the lumen.

In at least one embodiment, the cautery tool is configured and dimensioned, so that when the handle is slid distally with respect to the lumen, thereby biasing the biasing member, the cauterizing element extends distally from a distal end of the lumen, and when a driving force is released from the handle, the biasing member drives the handle proximally with respect to the lumen, thereby retracting the cauterizing element into the lumen.

A graspers tool configured and dimensioned to be slid through a lumen of a device that also receives an endoscope is provided, including: grasping jaws connected to an actuator via an elongated linkage; a sheath configured and dimensioned to be slid through the lumen of the device and to surround the grasping jaws and the linkage during sliding within the lumen; the actuator being operable to slide the grasping jaws distally with respect to the sheath to extend the grasping jaws distally beyond a distal end of the sheath.

In at least one embodiment, the actuator is further actuatable to open and close the grasping jaws.

A scissors tool configured and dimensioned to be slid through a lumen of a device that also receives an endoscope is provided, including: scissors jaws connected to an actuator via an elongated linkage; a sheath configured and dimensioned to be slid through the lumen of the device and to surround the scissors jaws and the linkage during sliding within the lumen; the actuator being operable to slide the scissors jaws distally with respect to the sheath to extend the scissors jaws distally beyond a distal end of the sheath.

In at least one embodiment, the actuator is further actuatable to open and close the scissors jaws.

A minimally invasive method of routing a flexible tool around an internal structure in a patient's body is provided, including the steps of: inserting a device including an endoscope through a small opening in the patient and advancing the device to position a distal end of the device into a surgical space in which the internal structure resides; inserting the flexible member through a service port in the device and extending a distal end portion of the flexible member distally of a lumen joined by the service port; visually confirming positioning of the distal end portion via the endoscope; removing the device from the patient via the small opening while maintaining the flexible member in the patient, substantially in the current position of the flexible member; inserting the device through a second small opening in the patient and advancing the device to position the distal end of the device into the surgical space in which the internal structure resides, on a side of the internal structure opposite to the side in which the flexible member is placed; connecting the distal end of the device with the distal end portion of the flexible member; and removing the device from the patient via the second small opening, thereby drawing the flexible member around the internal structure.

In at least one embodiment, the method further includes further comprising advancing the distal end of the flexible member partially around the internal structure after removing the device from the patient via the small opening while maintaining the flexible member in the patient, substantially in the current position of the flexible member.

In at least one embodiment, the method includes visualizing the distal end of the flexible member through the endoscope to align the device with the flexible member to perform the connecting step.

In at least one embodiment, the distal end of the flexible member comprises a snare loop and the connecting step comprises cinching the snare loop over a distal end portion of the device.

In at least one embodiment, the method includes fixing an ablation device to the proximal end of the flexible member and further advancing the flexible member by drawing the flexible member out of the second opening, thereby routing the ablation device around the internal structure.

In at least one embodiment, the internal structure comprises a plurality of pulmonary veins.

In at least one embodiment, the method includes ablating tissue along a pathway defined by the ablation device around the internal structure.

In at least one embodiment, the distal end of the flexible member comprises a ball and the connecting step comprises inserting a retrieval hook tool through a service port of the device, extending a hook of the retrieval hook tool distally of a distal end of a lumen that is in fluid communication with the service port, and hooking the distal end portion of the flexible member with the hook.

In at least one embodiment, the distal end of the flexible member comprises a snare loop and the connecting step comprises inserting a retrieval hook tool through a service port of the device, extending a hook of the retrieval hook tool distally of a distal end of a lumen that is in fluid communication with the service port, and hooking the snare loop with the hook.

In at least one embodiment, the distal end of the flexible member comprises a ball and the connecting step comprises inserting a trigger snare tool through a service port of the device, extending a snare of the trigger snare tool distally of a distal end of a lumen that is in fluid communication with the service port, and snaring the distal end portion of the flexible member by cinching down the snare loop after placing the snare loop over the ball.

In at least one embodiment, after said inserting the through a small opening in the patient and prior to advancing the device to position a distal end of the device into a surgical space in which the internal structure resides, a step of perforating at least one tissue layer to establish a pathway for the advancing step is performed.

In at least one embodiment, the perforating step comprises inserting a perforating tool through a service port of the device, extending a perforating member distally of a distal end of a lumen that is in fluid communication with the service port and into contact with tissue to be perforated, and perforating the tissue.

In at least one embodiment, the perforating step comprises inserting a perforating tool through a service port of the device, extending a perforating member distally of a distal end of a lumen that is in fluid communication with the service port and into contact with tissue to be perforated, grasping the tissue and retracting the grasped tissue against a cutting blade, thereby perforating the tissue.

In at least one embodiment, the method further includes reinserting the device into at least one of the first and second openings, advancing the distal end of the device toward the internal structure, and visually inspecting at least a portion of the lesion formed around the internal structure via the endoscope.

In at least one embodiment, the method further includes reinserting the device into at least one of the first and second openings, advancing the distal end of the device toward the internal structure, inserting a mapping probe tool through a service port in the device, extending mapping probe elements distally of a distal opening of a lumen in fluid connection with the service port, contacting tissue on opposite sides of a lesion, formed by the ablating step, with at least one mapping probe on each side of the lesion, and measuring sufficiency of the lesion formed with the mapping probe tool.

A minimally invasive method of routing a flexible tool around an internal structure in a patient's body is provided, including: inserting a device including an endoscope through a small opening in the patient and advancing the device to position a distal end of the device into a surgical space in which the internal structure resides; inserting the flexible member through a service port in the device and extending a distal end portion of the flexible member distally of a lumen joined by the service port; visually confirming the distal end portion via the endoscope; retracting the device to remove the flexible member from a distal end of the lumen, while maintaining the flexible member in the patient, substantially in the current position of the flexible member; distally advancing the device into patient to position the distal end of the device into the surgical space in which the internal structure resides, on a side of the internal structure opposite to the side in which the flexible member is placed; connecting the distal end of the device with the distal end portion of the flexible member; and removing the device from the patient via the small opening, thereby drawing the flexible member around the internal structure.

In at least one embodiment, the method further includes advancing the distal end of the flexible member partially around the internal structure after removing the flexible member from the device while maintaining the flexible member in the patient, substantially in the current position of the flexible member.

In at least one embodiment, the method further includes fixing an ablation device to the proximal end of the flexible member and further advancing the flexible member by drawing the flexible member out of the opening, thereby routing the ablation device around the internal structure.

In at least one embodiment, the method further includes ablating tissue along a pathway defined by the ablation device around the internal structure.

A minimally invasive method of routing a flexible tool around an internal structure in a patient's body is provided, including the steps of: inserting a device including a semi-flexible sheath slid over an endoscope through a small opening in the patient and advancing the device to position a distal end of the device into a surgical space in which the internal structure resides, the semi-flexible sheath including a rigid, transparent distal end that allows viewing therethrough via the endoscope; visually confirming placement of the distal end of the semi-flexible member via the endoscope; removing the device endoscope from the patient via the small opening while maintaining the semi-flexible member and rigid distal end in the patient, substantially in the current position of the semi-flexible member and rigid distal end; inserting the endoscope through a second small opening in the patient and advancing the endoscope to position the distal end thereof into the surgical space in which the internal structure resides, on a side of the internal structure opposite to the side in which the semi-flexible member is placed; connecting the distal end of the endoscope with the distal end of the semi-flexible member; and removing the endoscope from the patient via the second small opening, thereby drawing the semi-flexible member around the internal structure.

In at least one embodiment, the method further includes advancing the distal end of the semi-flexible member partially around the internal structure after the removal of the endoscope from the patient via the small opening while maintaining the semi-flexible member in the patient, substantially in the current position of the flexible member.

In at least one embodiment, the method further includes visualizing the distal end of the flexible member through the endoscope to align the device with the flexible member to perform the connecting step.

In at least one embodiment, the method further includes sliding a sleeve having a distal tip over the endoscope prior to inserting the endoscope through a second small opening.

In at least one embodiment, the sleeve comprises a snare loop extending from the distal tip, the snare loop being threaded through a distal tip and the distal tip being mounted to the endoscope.

In at least one embodiment, the connecting step comprises cinching the snare loop around the distal end of the semi-flexible member.

In at least one embodiment, the cinching is performed by sliding the sleeve proximally with respect to the endoscope.

In at least one embodiment, the method further includes fixing an ablation device to the proximal end of the semi-flexible member and further advancing the semi-flexible member by drawing the semi-flexible member out of the second opening, thereby routing the ablation device around the internal structure.

In at least one embodiment, the method further includes ablating tissue along a pathway defined by the ablation device around the internal structure.

A method of performing rapid exchange of tools in a device while performing a minimally invasive surgical procedure is provided, including the steps of: inserting a device having at least and an endoscope and a first tool received therein, through a small opening in the patient and advancing the device to position a distal end of the device into a reduced-access surgical space; removing the first tool from the device, while maintaining the device and the endoscope in the surgical space; and inserting a second tool into the device, thereby replacing the tool having been removed.

In at least one embodiment, the removing step comprises removing the first tool through a slot opening to an external surface of the device from a lumen in the device.

In at least one embodiment, the first tool comprises a snare catheter.

In at least one embodiment, the removing step comprises removing the first tool from an eyelet on a distal end portion of the device.

In at least one embodiment, the lumen from which the slot opens is asymmetrical in cross-section and forms a cam surface permitting the second tool to be rotated into the lumen.

In at least one embodiment, the device comprises a ring provided over an elongated shaft of the endoscope and axially slidable with respect thereto, and wherein the removing step comprises releasing the first tool from the ring.

In at least one embodiment, the device comprises a jig having slots configured and dimensioned to receive and releasably fix the endoscope and the first tool.

In at least one embodiment, the device comprises a pair of such jigs.

In at least one embodiment, the device comprises a jig having an opening configured and dimensioned to receive and releasably fix the first tool thereto for rapid exchange procedures; and an opening configured and dimensioned to receive the endoscope therethrough, wherein the endoscope is freely slidable with respect to the jig.

A method of relieving side loading by an operating room suction tubing on a device in fluid communication with the operating room suction tubing is provided, including the steps of: providing a length of tubing having a lighter gauge than a gauge of the operating room suction tubing, the length of tubing having proximal and distal ends; connecting the distal end of the length of tubing to a suction assembly of a device to be used to apply suction; and connecting the proximal end of the length of tubing to the operating room suction tubing, thereby putting the suction assembly of the device in fluid communication with the operating room suction tubing.

In at least one embodiment, the method further comprises clamping the length of tubing to a support.

In at least one embodiment, the length of tubing comprises a tether extending therefrom, and the clamping step comprises clamping the tether to the support.

In at least one embodiment, the support is a surgical drape.

A tool for relieving side loading on a device in fluid communication with an operating room suction tube is provided, including: a length of tubing having a lighter gauge than a gauge of the operating room suction tubing, the length of tubing having proximal and distal ends; a first connector at a distal end of the length of tubing configured and dimensioned to be connected to a suction assembly of the device, to establish fluid communication between the suction assembly and the length of tubing; a second connector at a proximal end of the length of tubing configured and dimensioned to be connected to the operating room suction tube, to establish fluid communication between the operating room suction tube and the length of tubing; and a tether extending from the length of tubing, the tether adapted to be clamped to a support.

These and other features of the invention will become apparent to those persons skilled in the art upon reading the details of the devices, tools and methods as more fully described below.

BRIEF DESCRIPTION OF THE DRAWINGS

FIG. 2C is a plan view of a device, similar to that shown in FIG. 2A, but having a dissecting tip.

FIG. 2D is an exploded view of a device that is similar to device shown in FIG. 2A, configured for routing an implement along a navigational course in a reduced access surgical environment.

FIG. 2E is a plan view of a device, similar to that shown in FIG. 2A, but having a ball tip.

FIG. 3A shows an assembled view of a device with an endoscope inserted.

FIG. 3B shows an exploded view of the arrangement shown in FIG. 3A.

FIG. 4K shows a ball ended tip that may be used for routing an implement along a navigational course in a reduced access surgical environment, and/or for retrieving an implement already having been so routed.

FIG. 4L shows a variation of the tip shown in FIG. 4K, in which a slot, groove, notch or other securement feature is provided at the proximal end portion of the ball.

FIG. 4M shows a tip similar to that of FIG. 4K and in which a similar offset has been designed and in which the distal end portion of the lens has varied thickness.

FIGS. 4N and 4O show sectional and distal end views of a variation of a ball-ended tip that includes openings configured to communicate with lumens in a device to which it is attachable.

FIG. 25A shows a snare capture tool.

FIG. 25B is an enlarged view of the proximal end portion of the snare capture tool shown in FIG. 25A.

FIG. 25C is an enlarged view of the distal end portion of the snare capture tool shown in FIG. 25A.

FIG. 26A shows an elongated retrieval hook tool configured and dimensioned to be slid though a lumen of a device described herein.

FIG. 26B illustrates the tool shown in FIG. 26A in use.

FIG. 29A illustrates a partial view of a mapping probe tool that may be used in a device described herein.

FIG. 29B shows a variation of the tool of FIG. 29A.

FIG. 29C shows another variation of the tool of FIG. 29A.

FIG. 30 illustrates a partial view of a linear ablating probe tool that may be used in a device described herein.

FIG. 31 illustrates a distal end portion of a point/disk ablation probe tool that may be used in a device described herein.

FIG. 32 illustrates a distal end portion of a monopolar cautery tool that may be used in a device described herein.

DETAILED DESCRIPTION OF THE INVENTION

Figure 1A:
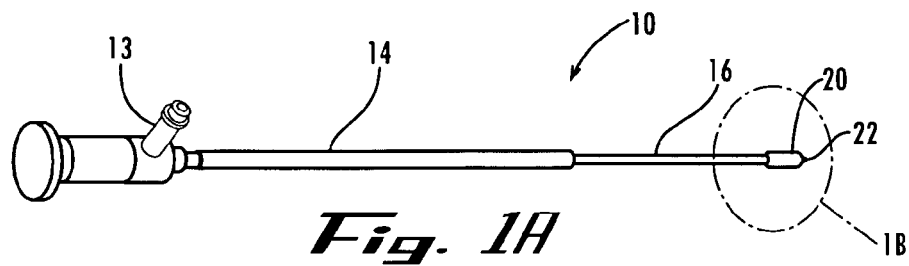
FIG. 1A shows a dissecting instrument that may be used to carry out procedures during the performance of methods described herein.

Before the present devices and methods are described, it is to be understood that this invention is not limited to particular surgeries, tools, materials, methods or devices described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods, devices and materials are now described. All publications mentioned herein are incorporated herein by reference to disclose and describe the methods, devices and/or materials in connection with which the publications are cited.

It must be noted that as used herein and in the appended claims, the singular forms "a", "an", and "the" include plural referents unless the context clearly dictates otherwise. Thus, for example, reference to "a lesion" includes a plurality of such lesions and reference to "the location" includes reference to one or more locations and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "open-chest procedure" refers to a surgical procedure wherein access for performing the procedure is provided by a full sternotomy or thoracotomy, a sternotomy wherein the sternum is incised and the cut sternum is separated using a sternal retractor, or a thoracotomy wherein an incision is performed between a patient's ribs and the incision between the ribs is separated using a retractor to open the chest cavity for access thereto.

The term "closed-chest procedure" or "minimally invasive procedure" refers to a surgical procedure wherein access for performing the procedure is provided by one or more openings which are much smaller than the opening provided by an open-chest procedure, and wherein a traditional sternotomy is not performed. Closed-chest or minimally invasive procedures may include those where access is provided by any of a number of different approaches, including mini-sternotomy, thoracotomy or mini-thoracotomy, or less invasively through a port provided within the chest cavity of the patient, e.g., between the ribs or in a subxyphoid area, with or without the visual assistance of a thoracoscope. It is further noted that minimally invasive procedures are not limited to closed-chest procedures but may be carried out in other reduced-access, surgical sites, including, but not limited to, the abdominal cavity, for example.

The term "reduced-access surgical site" refers to a surgical site or operating space that has not been opened fully to the environment for access by a surgeon. Thus, for example, closed-chest procedures are carried out in reduced-access surgical sites. Other procedures, including procedures outside of the chest cavity, such as in the abdominal cavity or other locations of the body, may be carried out as reduced access procedures in reduced-access surgical sites. For example, the surgical site may be accessed through one or more ports, cannulae, or other small opening(s), sometimes referred to as "minimally invasive surgery". What is often referred to as endoscopic surgery is surgery carried out in a reduced-access surgical site.

Conventional minimally invasive thoracoscopy surgery typically uses three ports on each side of the patient from which access is required. A camera (e.g., an endoscope) is inserted through one port, typically the central port to give the surgeon a "bird's eye" or "god's eye" view of the surgical target. Instruments (e.g., graspers, scissors or other instruments) may then be inserted through the other two ports (e.g., on opposite sides of the camera) and manipulated to perform a surgical procedure, as the working ends of the instruments are viewed via the camera. For example, graspers may be inserted through one of the other two ports and a Kitner sponge stick may be inserted through the other of the two ports. This type of procedure also takes at least two people to perform it: typically an assistant will hold and operate the endoscope through the central port, while a surgeon manipulates the tools through the other two ports. For example, the surgeon may lift up the vena cava with one instrument, and then use the sponge stick to perform the dissection of pericardial layers. As the dissection progresses further inwardly, it can no longer be seen by the endoscope where it is originally positioned. When moving the endoscope in closer to regain a view of the dissection, there is risk of contacting the lens of the scope with the vena cava or other tissue, which blurs the view. Accordingly, the endoscope must then be taken all the way back out of the body through the central port, and wiped off or otherwise cleaned and reinserted. However, the same risk of smudging or blurring the lens persists each time the endoscope needs to be further advanced into the operative site. Accordingly, such a procedure is man-hour intensive, requiring at least two operators, and time consuming, as well as difficult. The present endoscopes use tips that are self-cleaning, and provide a direct view of the surgical procedure that is being performed, while at the same time, being controllable by the surgeon that is also performing the surgical procedure.

With regard to thoracoscopic endocardial atrial ablation procedures, some current surgical techniques may take in the neighborhood of three hours just to accomplish the task of encircling the pulmonary veins in preparation for performing an epicardial ablation.

The present invention provides simple, reliable and safe techniques for minimally invasive procedures, such as closed-chest cardiac procedures that require ports (typically three or less) on only one side of the patient, thereby reducing the invasiveness of procedures that typically require ports on both sides of the patient. Further, the present techniques are much faster, typically requiring only minutes (e.g., about thirty to sixty minutes), as opposed to hours (e.g., about three hours) to encircle the pulmonary veins, for example. Even for procedures that typically are single sided, the present invention may reduce the number of ports that are required on one side of the patient, compared to the three previously required by conventional techniques. Not only are the present techniques less invasive, but devices provided make the procedures easier and safer to carry out.

Referring now to FIG. 1A, a dissecting instrument 10 is shown that may be used to carry out procedures during the performance of methods described herein. Dissecting instrument 10 includes an endoscope having an elongated tube or shaft 16 (e.g., a rigid tube/telescope having a diameter of about 5 to about 7 mm and length of about 25-40 cm). Such endoscopes are available from various companies, including Olympus (Japan), and Stortz and Scholly (Germany). Tube or shaft 16 is typically rigid to provide the best maneuverability, once instrument 10 has been inserted into an area to perform surgical techniques, for dissecting using tip 20. As the dissection can be viewed using the endoscope of the same instrument 10, only one opening, such as a thoracotomy or port, or other small opening, such as a sub-xyphoid opening, to permit the insertion of instrument 10 is required for performing dissection.

For purposes of maintaining an established pathway through tissue, such as may be established by dissection as described, a non-collapsing, flexible or rigid tube 14 may be placed coaxially over the endoscope shaft 16 as shown in FIG. 1A. Tube 14 may be made from flexible material such as polyvinyl chloride or polyethylene, incorporated with metal (e.g., stainless steel, NITINOL™ (nickel-titanium alloy) or the like) or plastic (nylon, polyester, or the like) mesh to render it non-collapsing; or tube 14 may be constructed of rigid plastic, such as polycarbonate, liquid crystal plastic (LCP), ULTEM® (amorphous thermoplastic polyetherimide), or the like, or from stainless steel or the like. Tube 14 is freely slidable over shaft 16 and is initially positioned over the proximal portion of shaft 16 as shown in FIG. 1A, thereby leaving a distal portion with a smaller diameter profile for better mobility around the surgical space during dissection. For example, tube 14 may be about two thirds the length of shaft 16 for use in non-invasive epicardial ablation techniques as described below, wherein tube is about 27 cm. Of course, the present invention is not limited to this length or to the proportion of the lengths of tube 14 to shaft 16, as these may vary depending upon the applications that the instrument 10 may be used for, as well as other factors.

Figure 1B:
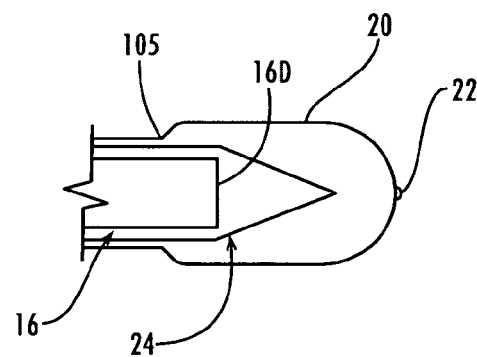
FIG. 1B shows an optional tapered or conical transparent tip mounted concentrically with respect to the endoscope and tip 20 and within tip 20 of FIG. 1A.

Tip 20 is transparent and generally blunt and may be of a generally spherical or other blunt curvature. However, a small (e.g., about 1 mm diameter) nipple or protrusion 22 may be provided to extend from the distal end of tip 20 to increase friction with the tip 20 against tissue to facilitate dissection. Tip 20 is transparent to enable direct viewing to the surgical site through endoscope 16 and of the dissection as it is proceeding. Tip 20 may be distanced from the lens at the distal end 16d of endoscope shaft 16 so that any tissue that contacts tip 20 can still be viewed by the endoscope, as the endoscope lens does not become smeared or blurred. Also, the distance between the external distal surface of tip 20 and the lens at the distal end of shaft 16d permits a field of view by endoscope 10, so that the anatomy can be better discerned since all tissue in contact with the length or long axis of the tip is viewed, rather than having a view that is limited to tissue that the endoscope lens contacts, as is the case when using a standard endoscope arrangement. For example, without a tip, an endoscope may bump up against the vena cava, but the view will not permit identification of such, as a constant wall of tissue will be seen in the field of view. Using a tip, however, a length of the vessel will be seen, with some surrounding background in the field of view, so that the vessel can be identified as such. Tip 20 may be removable to allow interchanging tip 20 with another tip for carrying out another function, as will be described in more detail below. Optionally, a tapered or conical transparent tip 24 may be mounted concentrically with respect to the endoscope and tip 20 and within tip 20, as shown in FIG. 1B. The surface of angled or conical tip 24 breaks up the reflected waves from the blunt tip 20 and prevents the formation of a ring of reflected light in the visualization through endoscope 16 that might otherwise occur. Further details about such an arrangement are described in co-pending application Ser. No. 11/137,987 filed May 26, 2005 and titled "Ablation Instruments and Methods for Performing Ablation", which is incorporated herein, in its entirety, by reference thereto. This configuration of a sharper tip 24 within a blunt tip 20 may be employed in ablation devices 10 that use a blunt tip 20 as described above, as well as other instruments designed to contact tissues while providing visualization.

A light emitter (not shown) may be provided in the distal end portion of instrument 10 to direct light out of the distal end so that the operator may visualize the position of the distal end in the surgical site by viewing through the endoscope 16. Like some existing endoscopes, the endoscope 16 provided with instrument 10 contains a visualization portion (e.g., rod lenses) and a fiber optic light-carrying portion (e.g., optical transmission fibers). A light cable connects to endoscope 16 and supplies light to the light-carrying portion, from an external light source (e.g., Xenon light source, which may be in the vicinity of 300 Watts power). Thus, a surgeon or operator may directly view the positioning and movements of the distal end of instrument 10 from outside the patient, without the need to resort to any indirect visualization or sensing techniques for positioning, and this greatly increases the accuracy and precision of placement of instrument 10 for performing dissection. The fact that the procedure can be viewed through the same instrument that is carrying out the dissection also removes the requirement for placing an additional opening through the patient to insert a separate endoscope, as is done with traditional endoscopic surgeries. A power supply line (not shown) may be connected to the light source to extend proximally out of the instrument 10 where it can be connected to an external power source.

While typically rigid, the distal end portion of instrument 10 may be formed to be articulating, to provide a greater range of motion during dissecting as well as for directing placement of tube 14 in examples where tube 14 is flexible. Further alternatively, endoscope 16 may be made flexible or malleable for situations where it would be advantageous for the particular application or technique being practiced.

Figure 2A:
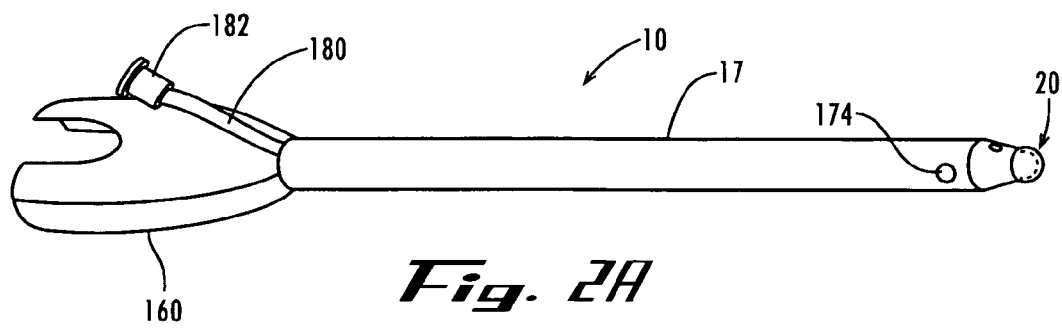
FIG. 2A shows another example of an instrument useful for performing procedures described herein.

FIG. 2A shows another example of an instrument 10 useful for performing procedures for epicardial atrial ablation. Instrument 10 includes main tube 17 that is configured to receive an endoscope therethrough, similar to the instrument shown in FIGS. 1A and 1B. Additionally, other lumens may be provided within main tube 17 to permit greater functionality of device 10, as described in more detail below with reference to FIG. 2D. The blunt, generally rounded tip 20 may be used in conjunction with an endoscope inserted into device 10 to provide visualization to facilitate navigation through into the body. In one embodiment, described below, visualization is provided to navigate through the transverse and oblique sinuses in a closed chest cavity.

Figure 2B:
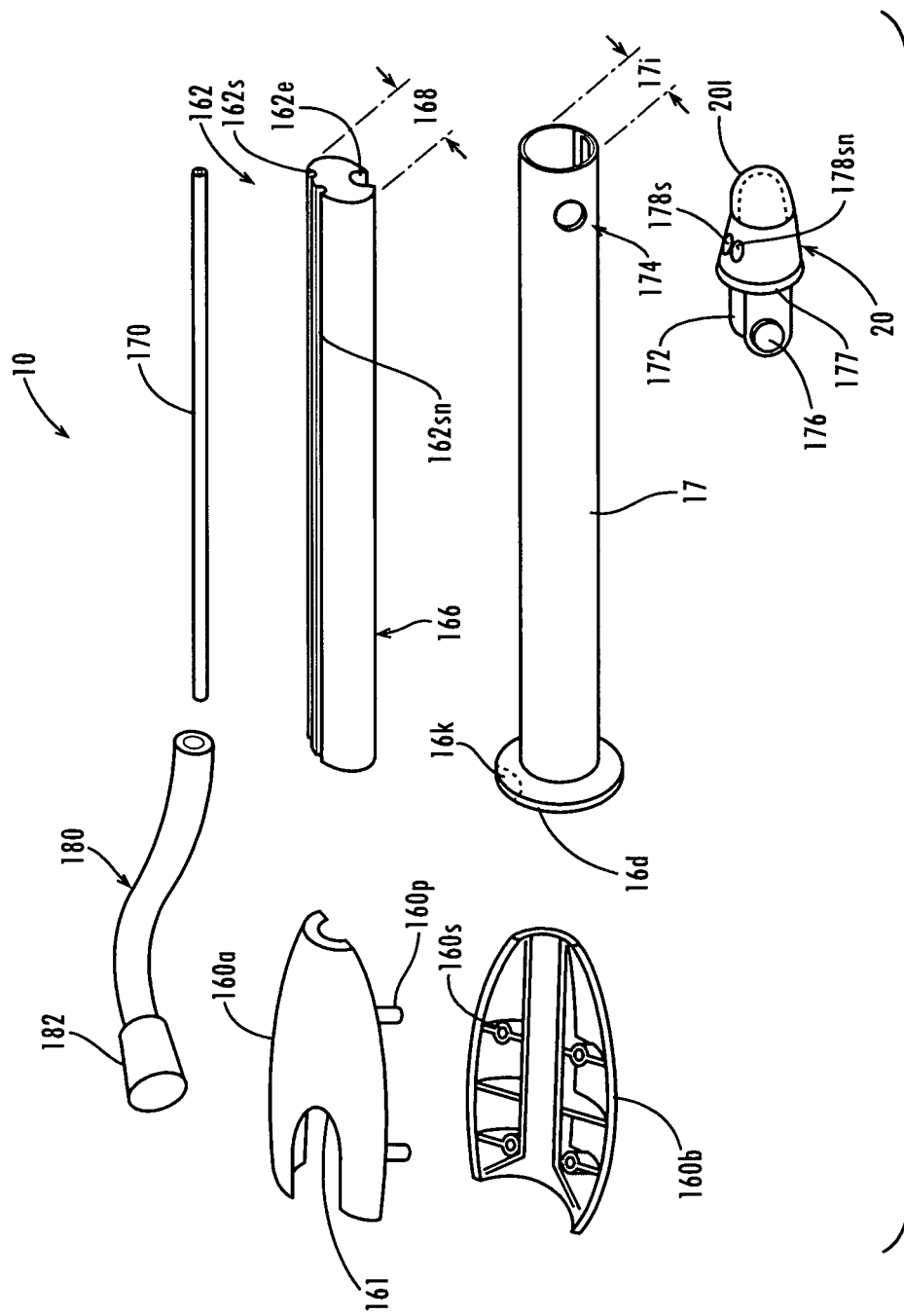
FIG. 2B is an exploded view of the device shown in FIG. 2A.

FIG. 2B is an exploded view of device 10 shown in FIG. 2A. FIG. 2C is a plan view of a device 10 having a dissecting tip 22. FIG. 2D is an exploded view of a device 10 that is similar to device 10 as shown in FIG. 2A, configured for routing an implement along a navigational course in a reduced access surgical environment. In one embodiment described below, device 10 may be used to route a snare device through the transverse sinus of a chest cavity and leave it there as device 10 is withdrawn. Device 10 may then be inserted into the oblique sinus to capture the snare as the loop of the snare is cinched around the ball tip 20 of device 10. In FIG. 2D, snare 30 may be inserted through a lumen in tube 17 so that loop 36 extends distally of opening 178sn for routing snare 30. Snare 30 can then be pushed through the lumen in tube 17 and out of opening 178sn, thereby leaving snare 30 in place as device 10 is withdrawn.

In all of the embodiments shown in FIGS. 2A-2E, main tube 17 is substantially rigid and may be made from stainless steel, or other biocompatible metal, alloy, rigid polymer or composite. The proximal end portion of main tube 17 is captured by handle 160. The proximal end of handle 160 is open to receive an endoscope that is guided therethrough and through main tube 17 via endoscope lumen 162e for viewing through tip 20. Handle 160 is typically formed in halves 160a,160b that may be assembled over the proximal end portion of main tube 17, thereby capturing tube 17 to prevent axial movements with respect to handle 160. Tube 17 may be mounted to allow rotation with respect to handle 160 (as shown in FIG. 2B), or may be mounted to prevent rotation. In order to prevent rotation, for example, proximal disk or washer may be formed with one or more scallops 16k (shown in phantom in FIG. 2B) and handle 160 may then be provided with a mating projection or key that mates with scallop 16k thereby preventing relative rotation between handle 160 and tube 17 once handle 160 has been assembled on tube 17.

Handle 160 is rigid and may be made of any of the materials described above for making tube 17. Typically handle 17 is molded form a rigid polymer, such as polycarbonate, for example. Pegs 160p (e.g., see FIG. 2B) may be provided to protrude from one portion 160b (such as in FIG. 7C, for example) of handle to mate with sockets or holes 160s (FIG. 7B) provided in corresponding locations of the other portion 160a of handle 160. Handle 160 may be further secured upon assembly by screws, bolts, adhesives, or the like or combinations of the same. FIGS. 7A-7C and 8A-8C show enlarged views of two variations of handles 160. In both of these handles 160, a recess 161 is provided in at least one of the handle halves 160a, 160b and is configured to receive the light post 13 that extends from the proximal end portion of endoscope 16 to be connected to a light source via fiber optic cable, for example, to thereby capture the endoscope and maintain it integrally with the handle 160, tube 17 and tip 20,20'.

Insert 166 (FIG. 2B) may be provided as a convenient way to form multiple lumens within main tube 17. Insert 166 has a major cross-section dimension 168 that is slightly less, but nearly equal to the inside diameter 17i of main tube 17, so that when insert 166 is inserted into main tube 17, it forms a friction fit with main tube 17. Alternatively, insert 166 may be configured to loosely slide within main tube 17, and upon insertion to the desired position, may be secured by one or more set screws or other mechanical and/or chemical expedient. Insert 166 may be further provided with one or more grooves or "half-lumens" 162 that, together with the inside wall of main tube 17 form full lumens when insert 166 is positioned within tube 17. In the example shown in FIG. 2B, a large half lumen 162e is provided to form a lumen in device 10 through which an endoscope will be passed, half lumen 162s is provided to form a lumen to receive suction tube 170, and half lumen 162sn is provided to form a lumen to pass a snare catheter through.

A further advantage provided by insert 166 is that multiple, interchangeable inserts 166 may be provided to change the lumen configuration of device 10. Thus, any or all of the size, relative positioning and number of lumens can be altered by use of a replacement insert 166 having a different configuration. For example, an additional insert may be provided to form four lumens 162 with tube 17. By removing the insert 166 shown in FIG. 2B from tube 17 and inserting the insert with four half lumens (not shown), device 10 would then be configured with four lumens. Device 10 may also be provided with the capability of interchanging tips 20, and therefore a tip having an additional through hole could also be interchanged to accommodate the additional lumen. Of course, inserts 166 with less than the number of half lumens 162 shown in FIG. 2B may be provided and interchanged to configure device 10 to have less than three lumens.

Figure 6A:
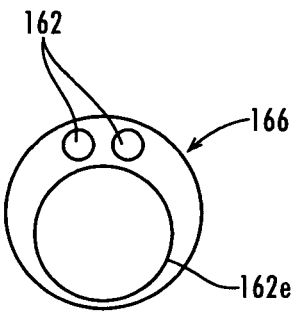
FIGS. 6A-6N show alternative arrangements for forming multiple lumens within a tube.

FIGS. 6A-6N show alternative arrangements for forming multiple lumens within a tube 17. In FIG. 6A insert 166 is shown which includes a primary, or relatively large lumen through which an endoscope may be passed, and two secondary, or relatively smaller lumens 162 for any of the uses described above. Insert 166 may be extruded from a suitable biocompatible polymer, such as polycarbonate or ABS plastic, for example. In FIG. 6B, lumen 162e and lumens 162 are each formed as independent tubes and then installed in tube 17. Alternatively, the independently formed tubes may be joined together with a heat shrink tubing to from tube 17, for example. The tubes defining lumens 162 may be metallic, such as stainless steel or other biocompatible metal known and used in the art, or may be made of substantially rigid polymer. The tube defining lumen 162e may be made from similar materials. The tubes defining the lumens may be installed in tube 17 as shown in cross-section in FIG. 6B and may be fixed to tube 17 by adhesives, ultrasonic welding, heat bonding, or in a releasably mechanical fixture, such as by using screws and/or set screws, brackets, clamps, or other mechanical expedient that would be readily apparent to one of ordinary skill in the art.

Figure 6E:
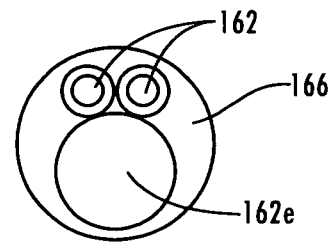
FIG. 6O is a partial, exploded view of a device showing a proximal end portion of a distal tip configured to function as a bracket to maintain a distal position of an inner tube relative to an outer tube.
FIG. 6P shows an example where a handle of the device functions as a bracket to maintain proximal end portions of inner in position relative to the outer tube.
Figure 6B:
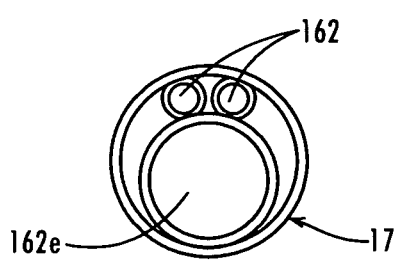
Figure 6F:
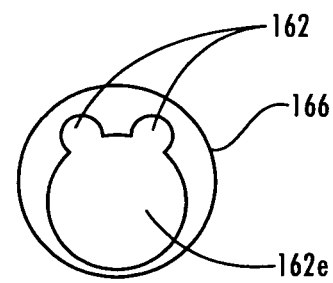
Figure 6C:
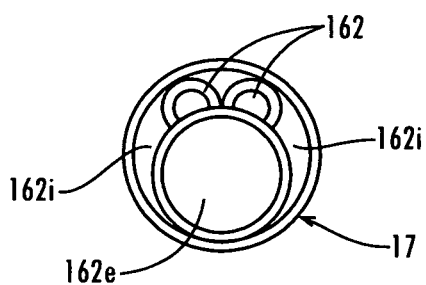

FIG. 6C shows a variation in which lumens 162 are not fully circular, but are formed by partial cylinders of material, such as half-pipes, or some other fraction of a full tubular structure. These partial cylinders may be made of any of the same materials described above with regard to the tubes defining lumens 162 in FIG. 6B. The spaces 162i resulting between the cylinders and partial cylinders may function as additional lumens, and may be used for irrigation, suction or delivery of a wire therethrough, for example. The tube defining lumen 162e may be the same as that described with regard to FIG. 6B. The partial tube may form a more secure fixation to the tube defining lumen 162e. Additionally or alternatively, the partial tubes may enable a lower profile tube 17 to be used, while still providing the number of lumens needed therewithin, with sufficiently large dimensions for each lumen.

Figure 6G:
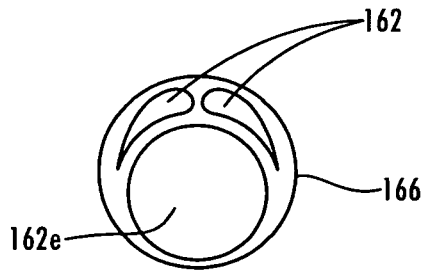
Figure 6D:
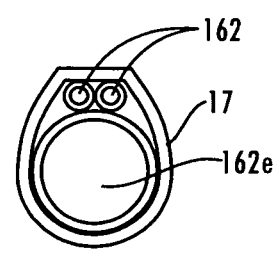

In FIG. 6D, the tubes defining the lumens may be the same as those described with regard to FIG. 6B. In this arrangement, tube 17 is form fitted around the configuration of tubes forming the lumens, to form a device have an overall more compact, smaller cross section, as the cross section of tube 17 is smaller relative to that shown in FIG. 6B, and is consequently not circular in cross-section, when using the same dimension tubes to form the lumens. In this example, the lumens are formed by three stainless steel tubes, around which a heat shrink wrapping is formed to make the outer enclosure 17.

In FIG. 6E, the main body of insert 166 may be formed of plastic, such as by extruding, for example, similar to that shown in FIG. 6A. In this arrangement, however, steel tubes are inserted through openings in insert 166 to define the smaller lumens 162. In this case, insert 166 may be formed by insert molding, coextrusion, or by forcing the steel tubes into the openings in insert 166.

FIG. 6F shows another variation of an extruded plastic insert configured to be inserted into a tube 17. In this arrangement, lumens 162e and 162 are continuously connected, as the smaller lumens 162 are formed as partial cylinders that open up to, or join lumen 162e.

FIG. 6G shows another insert 166 that may be extruded from plastic and that, in addition to primary lumen 162e, has a pair of secondary lumens 162e of non-circular cross-section. In FIG. 6G, lumens 162 are tear drop shaped, but lumens 162 may be formed to have any cross-sectional shape that can be extruded. Also, more or fewer than two lumens 162 can be formed, as in any of these examples. Further, the lumens 162 do not have to be symmetrical or of equal cross-sectional area.

Figure 6H:
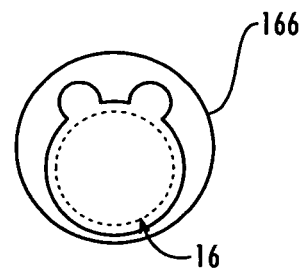
Figure 6P:
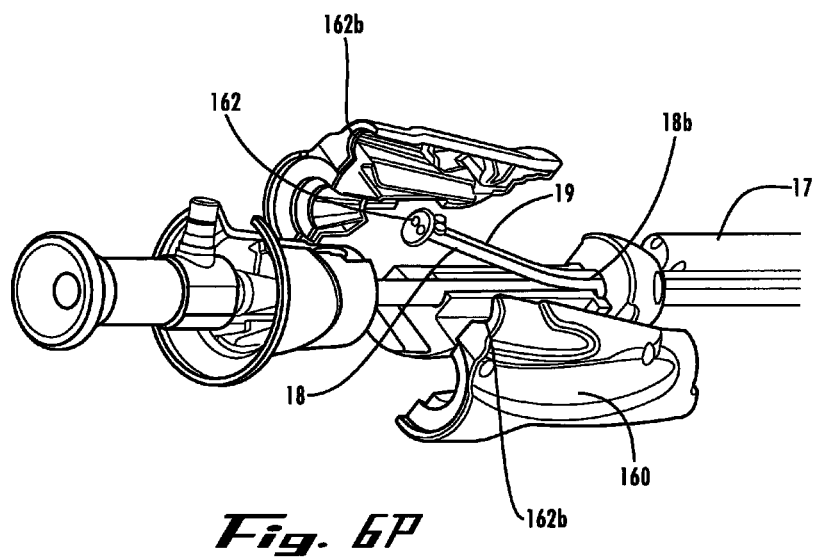
Figure 7A:
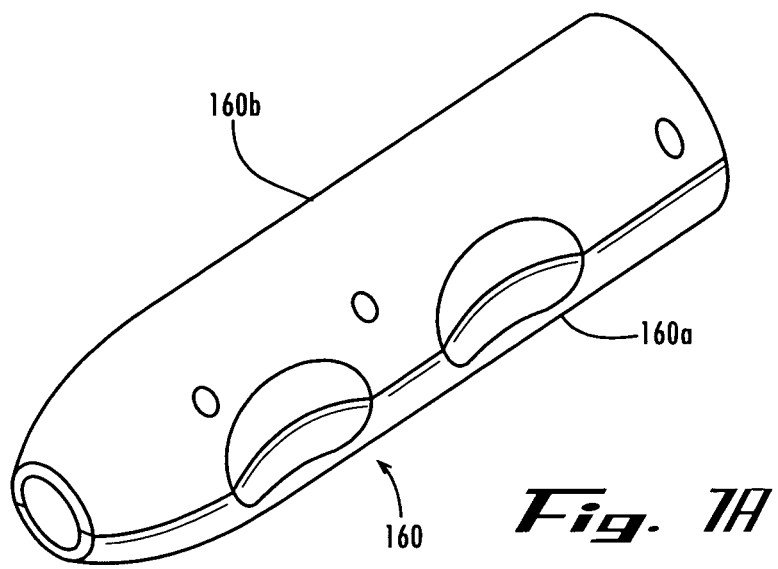
FIG. 7A is a perspective view of a handle employable in at least one device embodiment described herein.
Figure 7B:
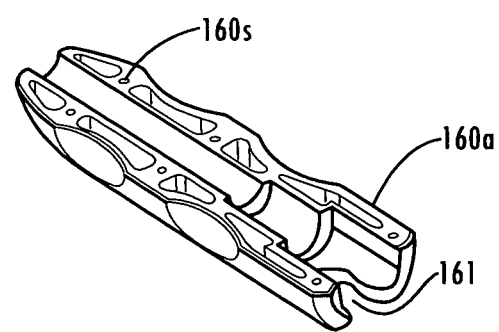
FIGS. 7B and 7C show opposite handle haves of the handle shown in FIG. 7A.
Figure 7C:
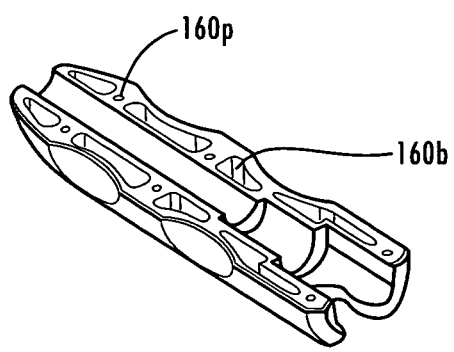
Figure 8A:
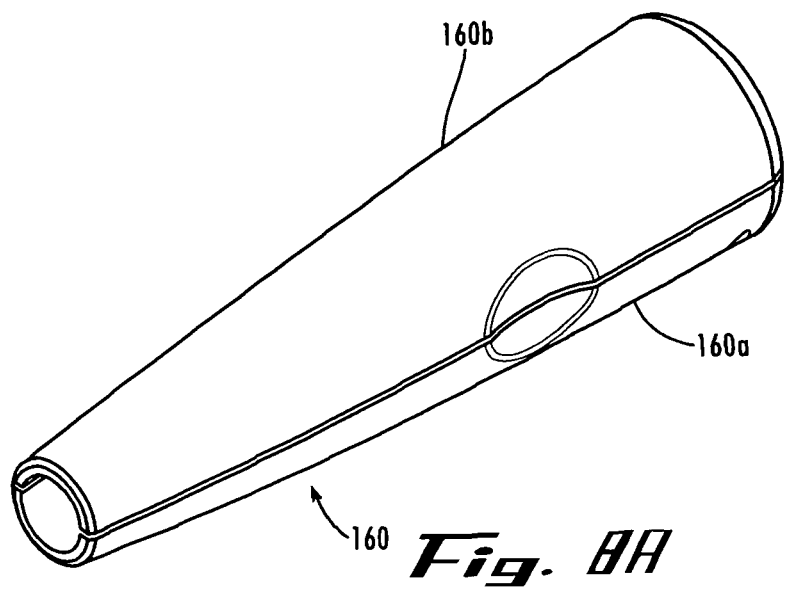
FIG. 8A is a perspective view of a variation of a handle employable in at least one device embodiment described herein.
Figure 8B:
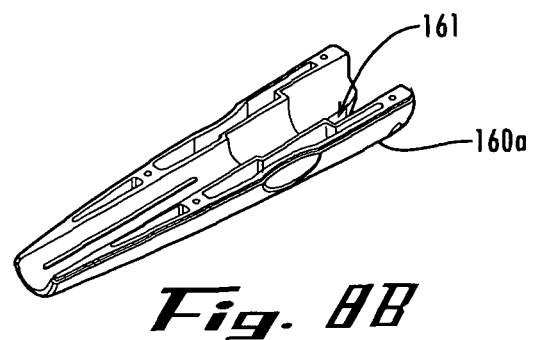
FIGS. 8B and 8C show opposite handle haves of the handle shown in FIG. 8A.
Figure 8C:
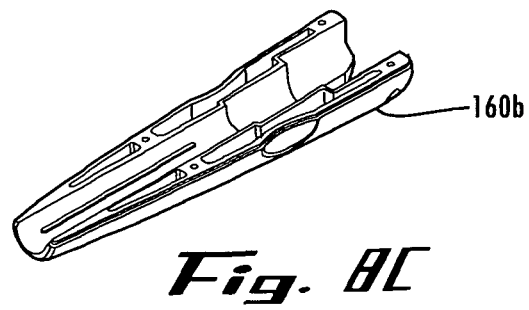

FIG. 6H illustrates a cross-sectional view of insert 166 from FIG. 6F with a shaft 16 of an endoscope residing therein as shown in phantom lines. In FIG. 6I, tube 17 has a pair of smaller tubes 18,19 (which may be steel) inserted therein and mounted thereto to form secondary lumens 162. FIG. 6I also illustrates endoscope shaft 16 (in phantom) installed in tube 17. The arrangement shown in FIG. 6H-6J eliminates the need to extrude the lumens 162, and requires no further manipulation or machining of tubes, as standard tubes can be assembled to form this arrangement. Furthermore, the tubes forming lumens 162 are not glued or welded or attached to each other in any way, but are held in position (mounted) by assemblies or brackets at their distal and proximal ends. For example, the distal end may be held by proximal portion 20p of distal tip shown in FIGS. 6O and 23B. Note that only one tube 18 is shown in FIG. 6I as an alternative to providing two tubes 18,19. FIG. 6P shows an example where handle 160 functions as a bracket 18b to maintain the proximal end portions of tubes 18,19 in position relative to tube 17. Additionally, handle 160 may fix a proximal adapter 162 of the tubes 18,19 via handle portion 162b.

FIG. 6J shows a perspective view of the distal portion of the arrangement shown in FIG. 6I (without the endoscope shaft 16), and shows that the tubes 18,19 that define lumens 162 may extend distally of tube 17 for registration with mating openings 178s,178m in a distal tip 20,20' to be connected thereto. FIG. 6K shows another configuration of an insert 166 which may be extruded from plastic. In this arrangement, snare lumen 162sn extends from and is continuous with main or primary (endoscope) lumen 162e. A pair of lumens 162s which may be used to apply suction, for example, extend on opposite sides of snare lumen 162sn. It will be appreciated that many more lumen configurations may be substituted for those shown, whether in an insert, or configured by tubes installed within tube 17.

FIGS. 6L-6N show another arrangement in which lumens 162 and 162e are formed by two stainless steel tubes of appropriate diameter that are joined together lengthwise (FIG. 6L), such as by welding, adhesives, or other expedient, see FIG. 6M. In this arrangement, in order to make device 10 as compact as possible, particularly at the distal working end of the device, the distal end portion of tube 17 is formed to be teardrop shaped, to minimize the cross-sectional area of the tube to substantially what is required by lumens 162,162e. The proximal end portion of tube is made circular to form a better seal with the opening made in the patient. Accordingly, tube 17 is completed by attached two half shells 17a,17b (FIG. 6N, 17b not shown) around the steel tubes that define the lumens 162, 162e. The proximal portions of shells 17a, 17b are semicircular in cross section, and the distal portions combine to make the reduced, teardrop cross-sectional shape.

Tip 20 may be configured to be interchanged, as noted above. In the example shown in FIG. 2B, tip 20 has prongs 172 extending proximally therefrom, with pins, pegs or other protrusions 176 extending therefrom. Tip 20 may further be optionally provided with a gasket or other seal 177 to prevent fluid flow into tube 17 where tip 20 meets tube 17. Main tube 17 is provided with openings 174 configured to receive protrusions 176, thereby locking tip 20 to main tube 17. Upon inserting, prongs 172 are flexed inwardly to allow protrusions 176 to pass within tube 17. The potential energy stored in prongs 172 by such flexing, drives prongs into openings 174 as the potential energy is converted to kinetic energy, and maintains them there, thereby locking tip 20 with respect to tube 17. To remove tip 20 for interchange, protrusions 176 are pressed inwardly to clear the walls of openings 174 and the tip can then be simply pulled out from its attachment with tube 17.

Figure 9A:
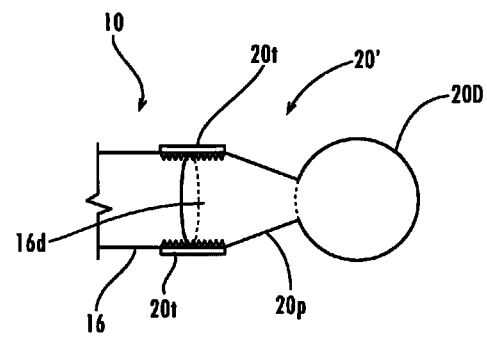
FIG. 9A illustrates a tip having threads provided at a proximal end portion thereof.
Figure 9B:
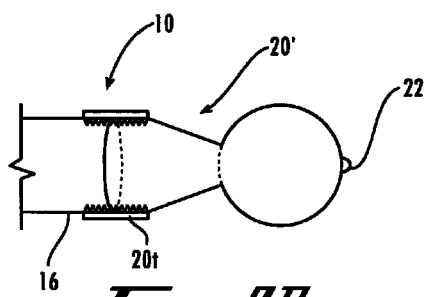
FIG. 9B illustrates another tip having threads provided at a proximal end portion thereof.

Alternatively, tip 20,20' may be provided with threads 20t (e.g., see tip 20, FIG. 9A and tip 22, FIG. 9B) at a proximal end portion thereof, for connecting tip 20,20' with mating threads on the distal end of shaft 16,17. Tips 20,20' may be injection molded in one piece from polycarbonate plastic, for example or from some other rigid, biocompatible and transparent plastic, glass or composite, or may be machined, for example.

Figure 9C:
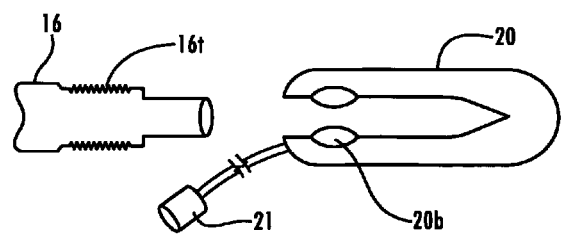
FIG. 9C shows an arrangement in which a tip is provided with a quick release mechanism.

FIG. 9C shows another arrangement in which any of tips 20,20' described may be provided with a quick release mechanism. In FIG. 9C, tip 20 is provided with an annular balloon 20b or a plurality of balloons arranged annularly within a proximal end portion of tip 20. Tip 20, when placed over the distal end of endoscope shaft 16 or main tube 17 is inflated to expand balloon 20b against the distal end portion of shaft 16 or tube 17. Shaft 16 or tube 17 may be provided with exterior threads, undercuts, an annular channel, a shoulder, knurling or other roughened features 16t to increase the friction and or anchor the positioning between the inflated balloon 20b and shaft/tube 16,17. Balloon 20b may be inflated by attaching an irrigation or suction catheter 21 to a valve provided in tip 20,20' and inputting compressed gas or saline or other biocompatible fluid under pressure. Catheter 21 is then removed and the valve automatically closes to maintain balloon 20b in the expanded configuration. To remove the tip, the pressurized gas or fluid is removed from balloon 20b, thereby reducing its size and releasing the friction grip/anchoring of the tip against the shaft/tube. Catheter 21 may be reattached to the valve of the tip to release pressure.

Tip 20,20' may be configured to provide the endoscope with an improved depth of field. The lens 201 of tip 20 (FIG. 2B) may be provided with a constant wall thickness throughout (and may be formed of clear polycarbonate, for example), and with a radius of curvature that allows the distal end of an endoscope to butt up against the inner surface of lens 201 and still be able to focus on tissues outside of the tip. Alternatively, the tip of the endoscope may stop at a predetermined distance from the inner surface of lens 201, without butting up against the inner surface. As noted, tips may be interchanged to provide specialized functions. For example, device 10 in FIG. 2C shows the tip 20 of FIG. 2A having been interchanged with tip 20 having a protrusion 22, similar to tips having been described above to facilitate dissection. FIG. 2E shows device 10 in which tip 20 has been replaced by ball tip 20'.

Figure 4A:
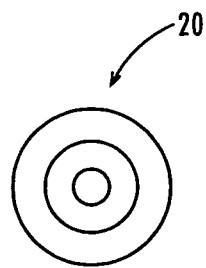
FIGS. 4A and 4B show an end view and longitudinal sectional view of a tip configured as an atraumatic viewing tip that offsets tissue from the endoscope lens by an offset distance.
Figure 4B:
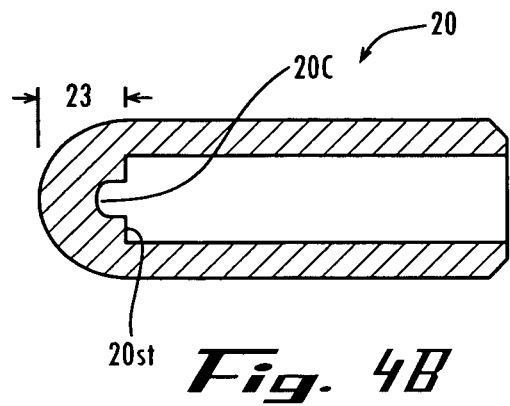
Figure 4C:
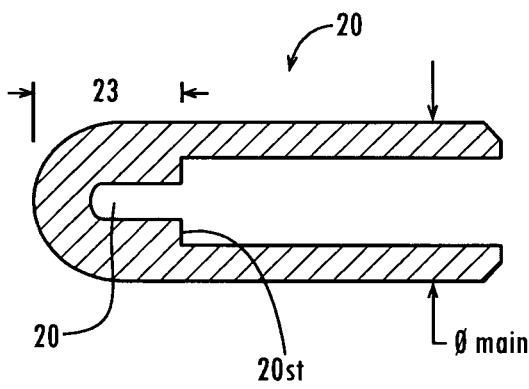
FIG. 4C shows one example of a tip having a different offset length than that of the example of FIG. 4B.

FIGS. 4A and 4B show an end view and longitudinal sectional view of tip 20 configured as an atraumatic viewing tip that offsets tissue from the endoscope lens by an offset distance 23, measured from an inner stop 20st that prevents further distal advancement of the distal end of the endoscope inserted within tip 20 to the distal end of tip 20. A smaller central channel 20c maintains the wall thickness of the tip at a substantially constant thickness to avoid visual distortion. Tips may be provided with varying offsets 23 to vary the depth of field available to the endoscope. FIG. 4C shows one example of tip 20 having a different offset length 23 than that of FIG. 4B.

Figure 4E:
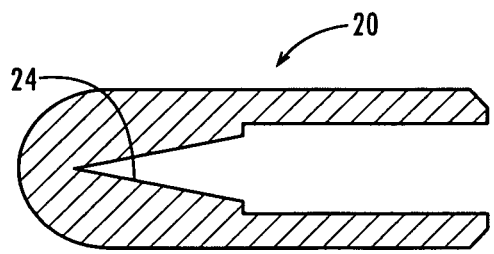
FIG. 4E shows another modification of a tip in which the distal surface has a parabolic profile or "bullet tip".
Figure 4D:
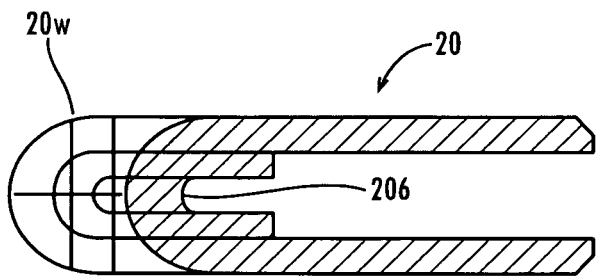
FIG. 4D shows a tip provided with a cage.

FIG. 4D shows another alternative arrangement, in which tip 20,20' may be provided with a cage, such as a metallic or polymeric, substantially rigid, atraumatic wire cage 20w. The structural members of cage 20w are spaced sufficiently so as not to substantially obstruct viewing through tip 20 and the endoscope, while offsetting the smooth distal surface of tip 20 from tissues, thereby further reducing smearing or obstruction of visualization. Cage 20w may be mounted to tip 20 by friction fit (press fit), threading, or other fixing means allowing removability of the cage from the tip, or may be adhered thereto, for example.

Figure 4F:
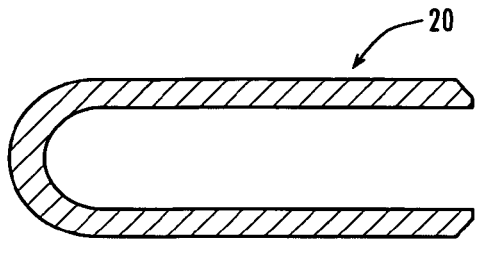
FIGS. 4F and 4G show tips which differ in configuration by the thickness of the lens at the distal end portion of the tip.
Figure 4G:
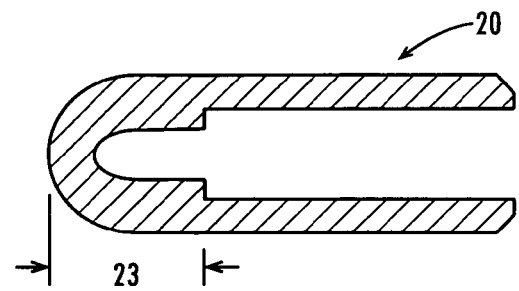

FIG. 4E shows another modification of tip 20 in which the distal surface has a parabolic profile or "bullet tip". Additionally, this or any other tip described herein may be provided with an inner tapered lens 24, which has been found to break up certain reflections that may otherwise be viewed through the endoscope. The configurations of FIGS. 4F and 4G differ by the thickness of the lens at the distal end portion of tip 20, wherein tip 20 in FIG. 4G is provided with a thicker distal lens portion to provide greater magnification. The relative thickness of the lens affects the magnification, but this also works in combination with the curvature of the lens (e.g., the degree of concavity or convexity). Thus, variation in the thickness of the lens wall can be provided to vary the degree of magnification and in this way compensate for optical distortions that would otherwise occur. The offset 23 of the two configurations shown in FIGS. 4F and 4G is about the same. Lens 20 can be configured to offset tissue from the distal end or lens of the endoscope by a distance of about 3 mm to about 20 mm. In one embodiment, the offset 23 is about 14 mm (between the distal tip of endoscope 16 and the distal tip of lens 20). The diameter of lens 20 can range from about 1 mm to about 20 mm. In one embodiment, the lens 20 diameter is about 7 mm.

Figure 4H:
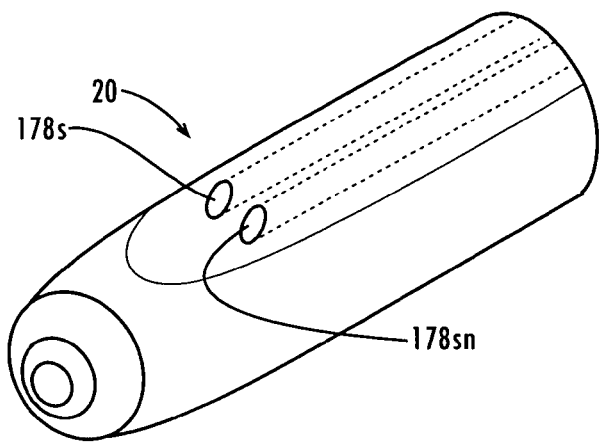
FIG. 4H shows a tip that is further provided with openings that communicate with lumens in a device to which the tip is connected.
Figure 4I:
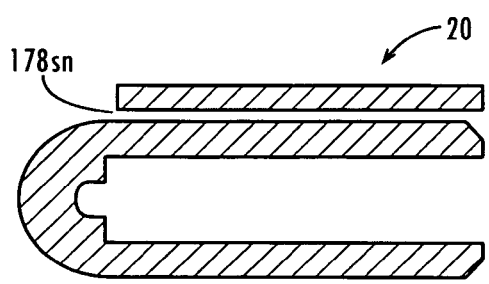
FIG. 4I is a sectional view of the tip of FIG. 4H.
Figure 4J:
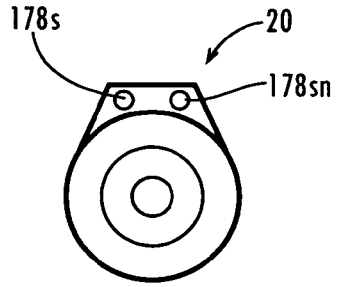
FIG. 4J is a distal end view of the tip of FIG. 4H.

Tip 20,20' may be further provided with openings 178 that communicate with lumens 162 in device 10. For example, while endoscope lumen 162e directs to lens 201 of tip 20 shown in FIG. 2B, opening 178s fluidly communicates with lumen 162s so that suction can be delivered outside of tip 20 (see also the embodiment shown in FIGS. 4I, 4J and 4H). Additionally, opening 178sn communicates with lumen 162sn, permitting a snare catheter to be passed distally of device 10 through lumen 162sn and opening 178sn. In instances where more or fewer lumens are provided in device 10, as described above, more or fewer openings 178 may be provided in tip 20, respectively.

FIGS. 4K-4O show still further alternative tip configurations that may be provided. FIG. 4K shows a ball ended tip 20 that may be used for routing an implement along a navigational course in a reduced access surgical environment, and/or for retrieving an implement already having been so routed, connecting to the implement, and further routing the implement along a further course. Tip 20' is a ball-ending tip that includes a tapered proximal portion 20p that may be conical or some other tapering shape that reduces in cross section in a distal direction. At the distal-most portion of proximal portion 20p, where proximal portion may be smallest in cross-section, a ball-shaped or spherical distal portion 20d is integral therewith and extends distally therefrom. Spherical portion 20d may be sized on the order of about 2-4 mm in diameter, for example, typically about 3 mm. Tip 20' may be injection molded in one piece from polycarbonate plastic, for example or from some other rigid, biocompatible and transparent plastic, glass or composite, or may be machined, for example.

Tip 20' (e.g., see FIGS. 2E, 4K, 4M, 5B, 9B) is particularly well-suited for engaging a snare catheter. When endoscope 10 is provided with tip 20' as described above, as endoscope 10 is manipulated within a closed surgical space for advancement of ball end 20d through suture loop 36, this procedure may be completely visualized through endoscope 10, as noted. After the ball end 20d of tip 20' passes through suture loop 36, suture loop 36 is cinched down on dissecting endoscope 10 proximal to ball end 20d at and against the proximal portion of the ball 20d as it is tightened and slides distally along tapered portion 20p to abut the ball 20d.

FIG. 4L shows a variation of the tip 20' shown in FIG. 4K, in which a slot, groove, notch or other securement feature 20g is provided at the proximal end portion of ball 20d. Upon cinching a snare 36 around tip 20' in a manner as described above, further insurance that snare 36 will not slip from its grasp of tip 20' is provided as a portion of snare 36 slides into groove 20g. FIG. 4M shows a tip 20' similar to that of FIG. 4K and in which a similar offset 23 has been designed and in which the distal end portion of the lens has varied thickness. FIGS. 4N and 4O show a variation of a ball-ended tip 20' that includes openings 178 configured to communicate with lumens in a device to which it is attachable.

Figure 4P:
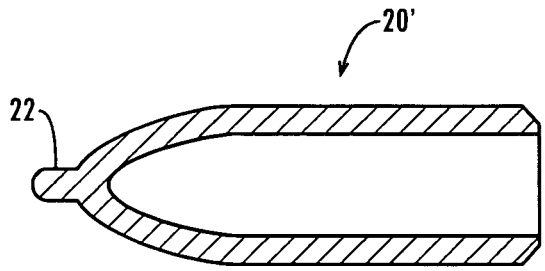
FIGS. 4P-4S show various tips that are adapted to facilitate dissection when connected to a device and inserted into a surgical space.
Figure 4S:
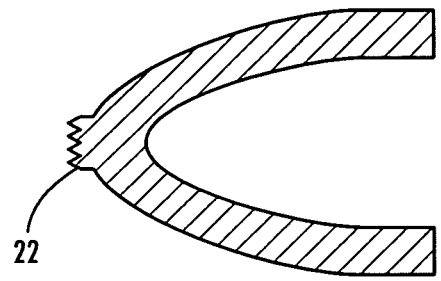
Figure 4Q:
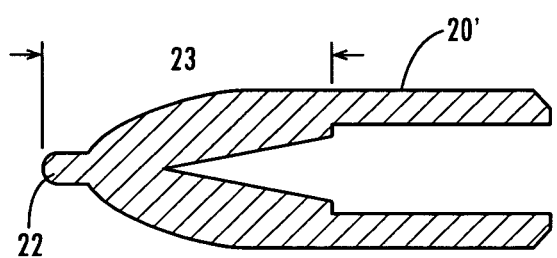
Figure 4R:
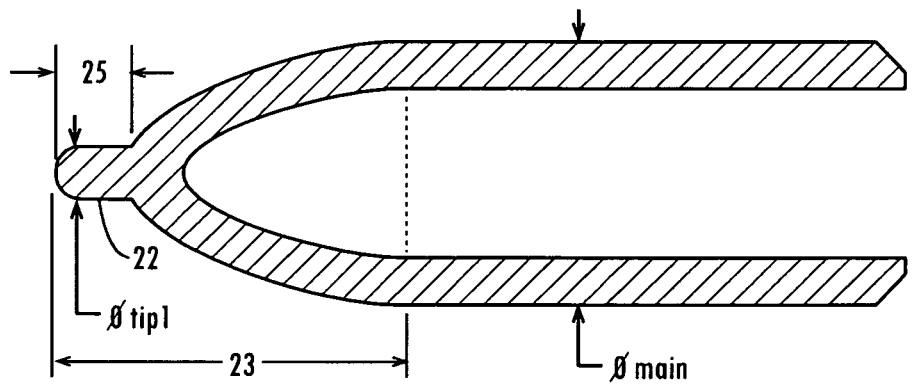

FIGS. 4P-4S show various tips that are adapted to facilitate dissection when connected to a device and inserted into a surgical space. In FIG. 4P, tip 20' is provided with a small (e.g., about 1 mm diameter) nipple or protrusion 22 to extend from the distal end of tip 20'. The length 25 of protrusion 22 may vary from about 0.25 to about 1.5 mm, and FIGS. 4P, 4Q and 4R show protrusions 22 of varying lengths. Also, any offset 23 provided may be variable, as with previously described embodiments. The configuration of FIG. 4Q shows a distal end portion of the tip having varied wall thickness. Alternatively, protrusion 22 may be formed as a knurled feature as shown in FIG. 4S, or other roughened feature that increases friction between tip 20' against tissue to facilitate dissection.

Figure 5A:
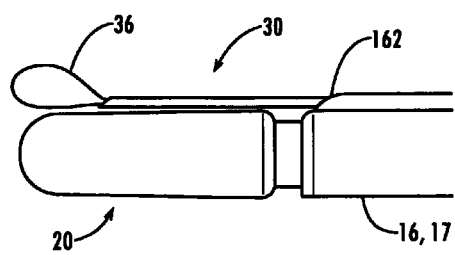
FIGS. 5A, 5B and 5C show a viewing tip, ball-ended tip and dissecting tip, respectively.
Figure 5B:
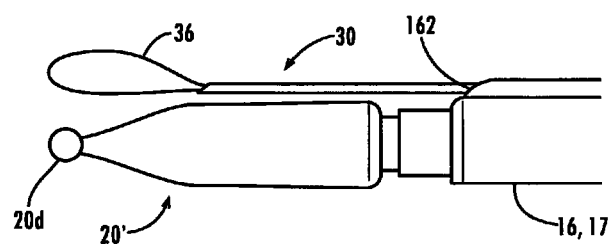
Figure 5C:
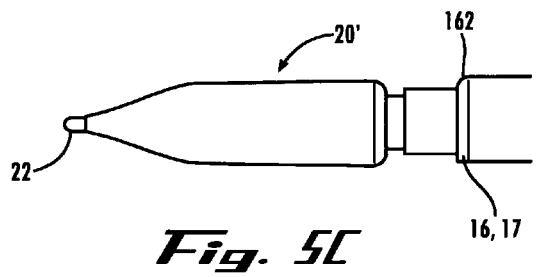

FIGS. 5A, 5B and 5C show a viewing tip 20, ball-ended tip 20' and dissecting tip 20', respectively. In each instance, one or more lumens 162 are provided in the shaft or tube 16,17 radially from the main lumen provided to receive the endoscope. In this way, suction, irrigation, or other implements can be delivered alongside tip 20,20'. FIGS. 5A and 5B each show a portion of a snare catheter 30 extending distally from lumen 162.

Referring back to FIG. 2B, suction tube 170 connects in fluid communication with suction luer 180, which may be made from TYGON® tubing or other vinyl, PVC or nylon surgical tubing. Suction luer 180 is further provided at a proximal end thereof with luer connector 182 configured to be connected with a source of vacuum, to thereby deliver suction to the distal end of device 10 through suction tube 170 and suction opening 178s. Similarly, an introducer tube 184 (FIG. 2C) may be provided to connect with snare luer 162sn to guide a snare catheter into device 10, through snare lumen 162sn and distally out of snare opening 178sn. Alternatively, proximal luer connector 182 may be connected to a fluid source (e.g., a syringe) to deliver irrigation, or a wash for lens cleaning. This irrigation can also be used in conjunction with an ablation probe (e.g., microwave powered probe, or other known ablation power source) to deliver local fluidic cooling in the vicinity of the ablation probe.

In FIG. 2D, handle 160 is provided as two handle halves 160a,160b and is rotatable with respect to shaft 17. In this way, the light cable connected to 131 can be rotated to be moved out of the operator's way by rotating handle 160 without the need to rotate shaft 17.

FIG. 3A shows an assembled view and FIG. 3B shows an exploded view of another embodiment of a device 10 with endoscope inserted. Shaft 16 of endoscope is inserted through the main lumen of shaft 17 so that the distal tip of the endoscope is positioned within tip 20, as described above. Snare catheter 30 is inserted through the lumen formed in tube 17s so that the distal loop (snare) of the snare catheter can be advanced distally of the distal opening of the lumen through tube 17s. Tube 17s is mounted externally of tube 17 and runs parallel therewith, so that the lumen in tube 17s is parallel with the main lumen of shaft 17.

Figure 10A:
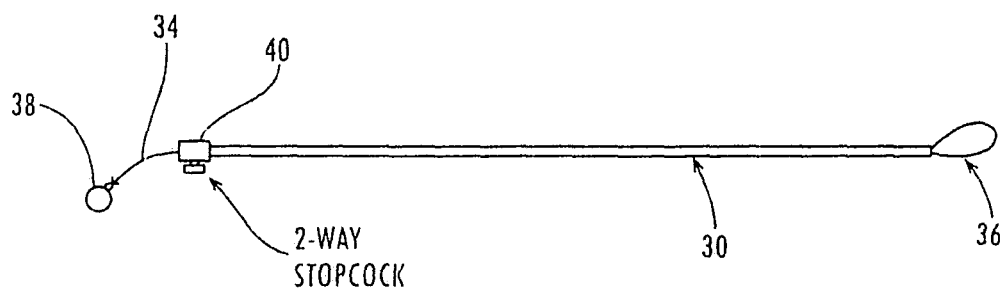
FIG. 10A shows an embodiment of a snare catheter that may be inserted into a tube or lumen for routing to a desired surgical location in a reduced-access surgical site.
Figure 10B:
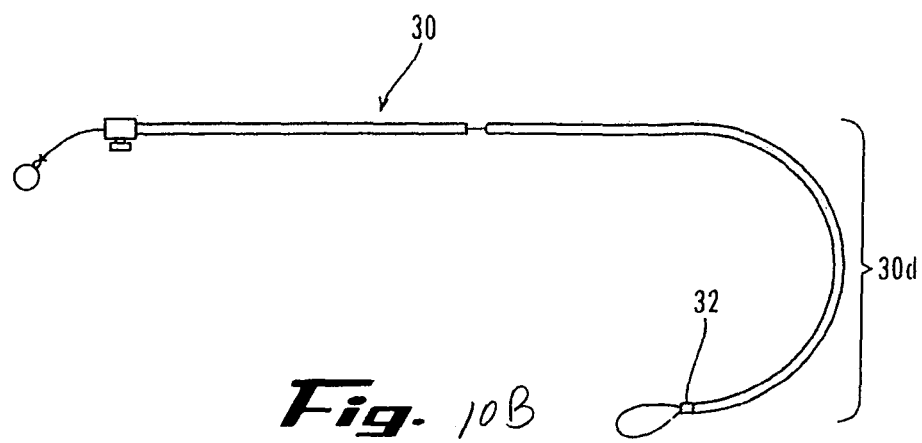
FIG. 10B shows an embodiment of a snare catheter having a preconfigured bend in its distal section when in an unstressed state.

FIG. 10A shows an embodiment of snare catheter 30 that may be inserted into tube 14 or through lumen 162sn in tube 17 and lumen 178 in tip 20,20' for routing to a desired surgical location in a reduced-access surgical site. Snare catheter 30 may be constructed of flexible plastic material such as high density polyethylene (HDPE), polytetrafluoroethylene (PTFE, e.g., TEFLON®), polyvinyl chloride, nylon, or the like. Snare catheter 30 may be formed to be substantially straight in an unstressed state (FIG. 10A) or to have a preconfigured bend in its distal section 30d as shown in FIG. 10B, (e.g., of about the last 10-15 cm of catheter length, which may assist in maneuvering the catheter along a similar curved pathway within the body, such as directing the tip downward after it has been passed through tube 14,17. Catheter 30 is sufficiently small to be easily slid through tube 14 or lumen 162sn and may be on the order of up to about 0.100" in outside diameter, typically no greater than about 0.087", for example. Catheter 30 may be provided with a rigid distal tip 32 made from a biocompatible metal or rigid polymer. Rigid tip 32 allows the snare to hold the ball tip 20d securely, as it does not give as the ball tip is drawn against it, wherein a soft tip may allow the ball tip to slip out when traction is applied to the snare catheter.

Catheter 30 is tubular, to allow suture line or wire 34 to pass therethrough. Suture line 34 includes a suture loop 36 and may be formed with a sliding knot (an Endoloop) in a distal end thereof. Suture loop 36 is located distally of the distal end of catheter 30. Suture loop may be formed from a conventional suture material or braided stainless steel wire cable, for example. Alternatively, the entire suture line may be made of NITINOL®, or other nickel-titanium alloy without the need to use a sliding knot. The proximal end of suture line or wire 34 (or tail of the suture loop) extends through catheter 30 and proximally out of the proximal end of catheter 30, where it may be attached to a pull tab 38. Further, a lock 40 such as a two-way stopcock, clamp, hemostats, or other surgical clamp, tool or locking mechanism may be provided to grasp suture line or wire 34 and abut the proximal end of catheter 30 to prevent backsliding of catheter 30 with respect to suture line 34 (i.e., sliding of catheter 30 proximally with respect to suture line 34) as this device is drawn by ball end 20*d*, or used to draw (route) an ablation device or other element into a desired surgical position, as will be described below.

Figure 11A:
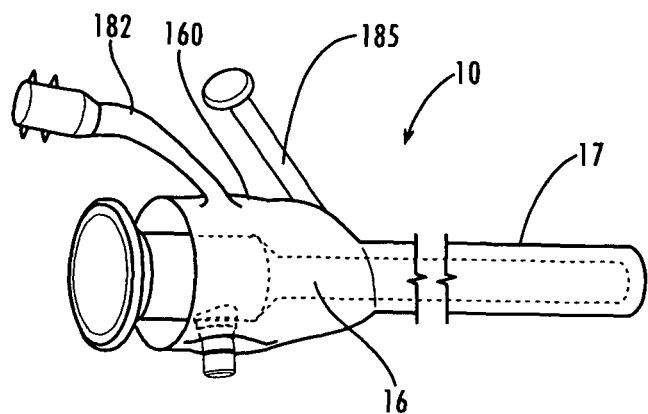
FIGS. 11A and 11B illustrated a partial view and sectional view of the distal end of another arrangement of an endoscope and tube, in which no tip is used.
Figure 11B:
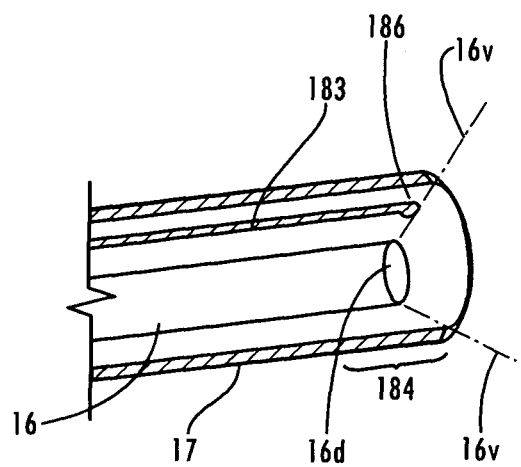

FIGS. 11A-11B illustrate another arrangement of an endoscope and tube 17, in which no tip 20,20' is present at all. Instead, tube 17 extends distally past the distal end (opening/lens through which light is received for viewing through the endoscope) 16*d* of the endoscope to shield it from contact with tissues as device 10 is traversed toward a surgical site along a pathway through and around tissues. The distal end of tube 17 is open and endoscope 16 views through the open end of tube 17. A luer fitting and tubing 185, or other input feature for connecting to a source of pressurized saline or other fluid may extend from handle 160 and fluidly connect with irrigation tube or lumen 183. At the distal end of tube or lumen 183, a nozzle 186 may be angled toward or oriented toward the distal end 16*d* of the endoscope, in a position that is out of the field of view (indicated by the dotted lines 16*v* in FIG. 11B). In this way, the distal tip 16*d* can be constantly, intermittently, or at will, irrigated to ensure that the lens of the endoscope does not become smudged or covered with blood or other tissue. Suction may be applied in any of the same manners through luer connector 182 as suction is applied to the distal end of tube 17 through one or more lumens to uptake the irrigation fluid. At least the distal end portion of tube 17 may be formed to be clear (transparent) to ensure that the field of vision 16*v* is not obstructed. Thus, the distal end portion of tube 17 physically shields 184 the distal end of the endoscope without inhibiting visibility.

Figure 12H:
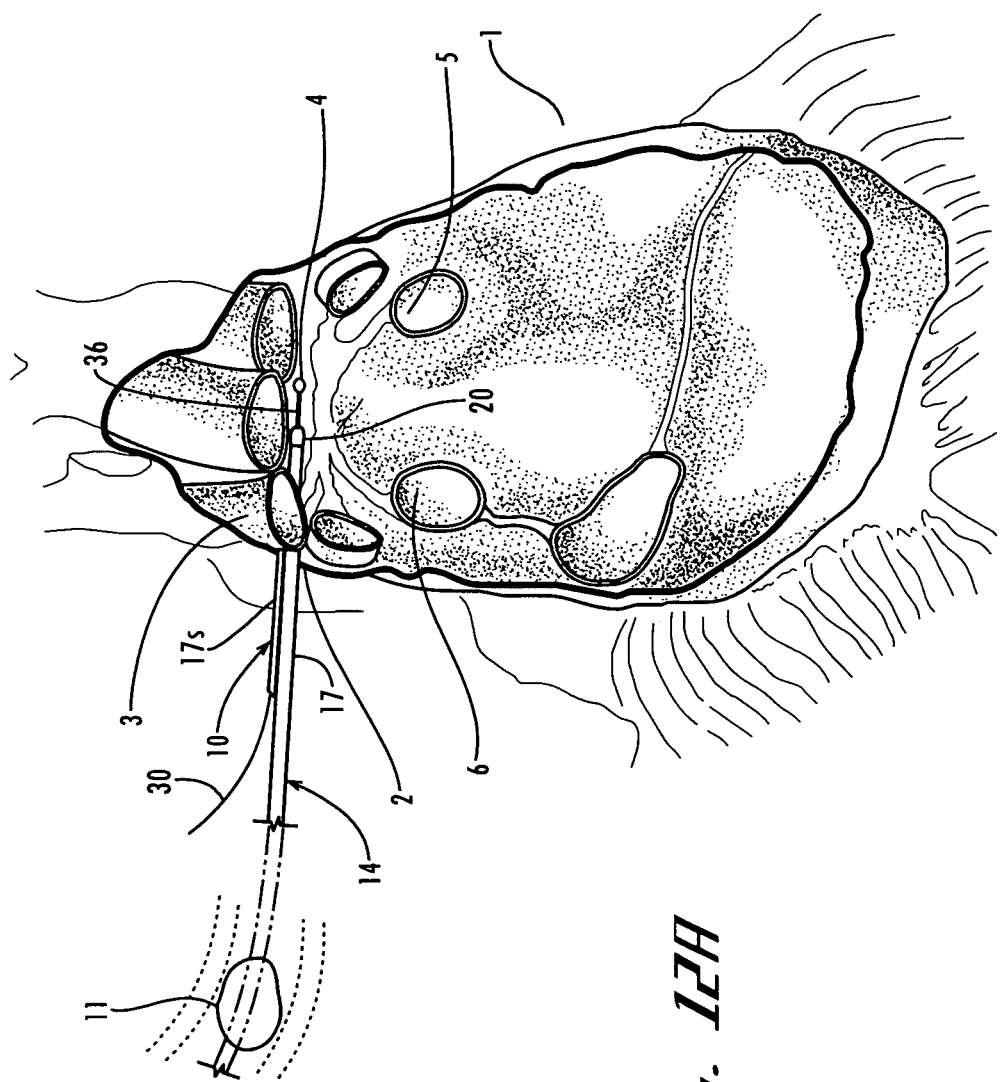
FIG. 12A illustrates a cutaway anterior view of a human heart with an instrument being used to penetrate the pericardial reflection.
FIG. 12B shows advancement of a snare loop to pass superiorly over the left pulmonary veins, around the left pulmonary veins and into the oblique pericardial sinus.
FIG. 12C shows an instrument having been inserted into the oblique sinus via a small opening in the patient.
FIG. 12D shows an ablation device fixed to the proximal end of a member having been routed around the pulmonary veins.

An example of using devices described herein in a method according to the present invention will now be described, initially with reference to FIG. 12A. FIG. 12A illustrates a cutaway anterior view of a human heart 1 with instrument 10 being used to penetrate the pericardial reflection 2. The right side of the pericardium has been previously incised, using endoscopic shears (not shown). At least one port or opening 11 is formed in the right chest of the patient (e.g., a port 11 though the second or third intercostal space of the right chest) to provide access to the heart by instrument 10. Instrument 10 is next inserted through opening 11 and tip 20,22 is used to dissect through pericardium 2 until superior vena cava 3 can be visualized through endoscope 16. Dissection may be performed by carefully scraping tip 20/protrusion 22 against the pericardial tissue to separate it with a side-to-side or up-and-down motion of tip 20, for example. Dissection through the pericardial membrane (pericardial reflection) is made posterior to the superior vena cava thereby providing an entrance to the transverse pericardial sinus 4. Upon achieving access to the transverse pericardial sinus 4 with instrument 10, snare catheter 30 may be inserted into the lumen in tube 17*s* and then distally advanced to extend snare loop distally from the lumen in tube 17*s*, as shown in FIG. 12A, to place it into the transverse pericardial sinus. Although the anatomical structures described herein are well-known and would be readily understood by those of ordinary skill in the art reading the present disclosure and referring to the Figs. herein, additional views may be found in United States Application Publication No. US2004/111101 A1, (e.g., see FIG. 1 and description thereof), which published on Jun. 10, 2004 and which is hereby incorporated herein, in its entirety, by reference thereto. Snare loop 36 may continue to be advanced until it passes superiorly over the left pulmonary veins, around the left pulmonary veins 5 and into the oblique pericardial sinus 7, as shown in FIG. 12B.

Figure 12B:
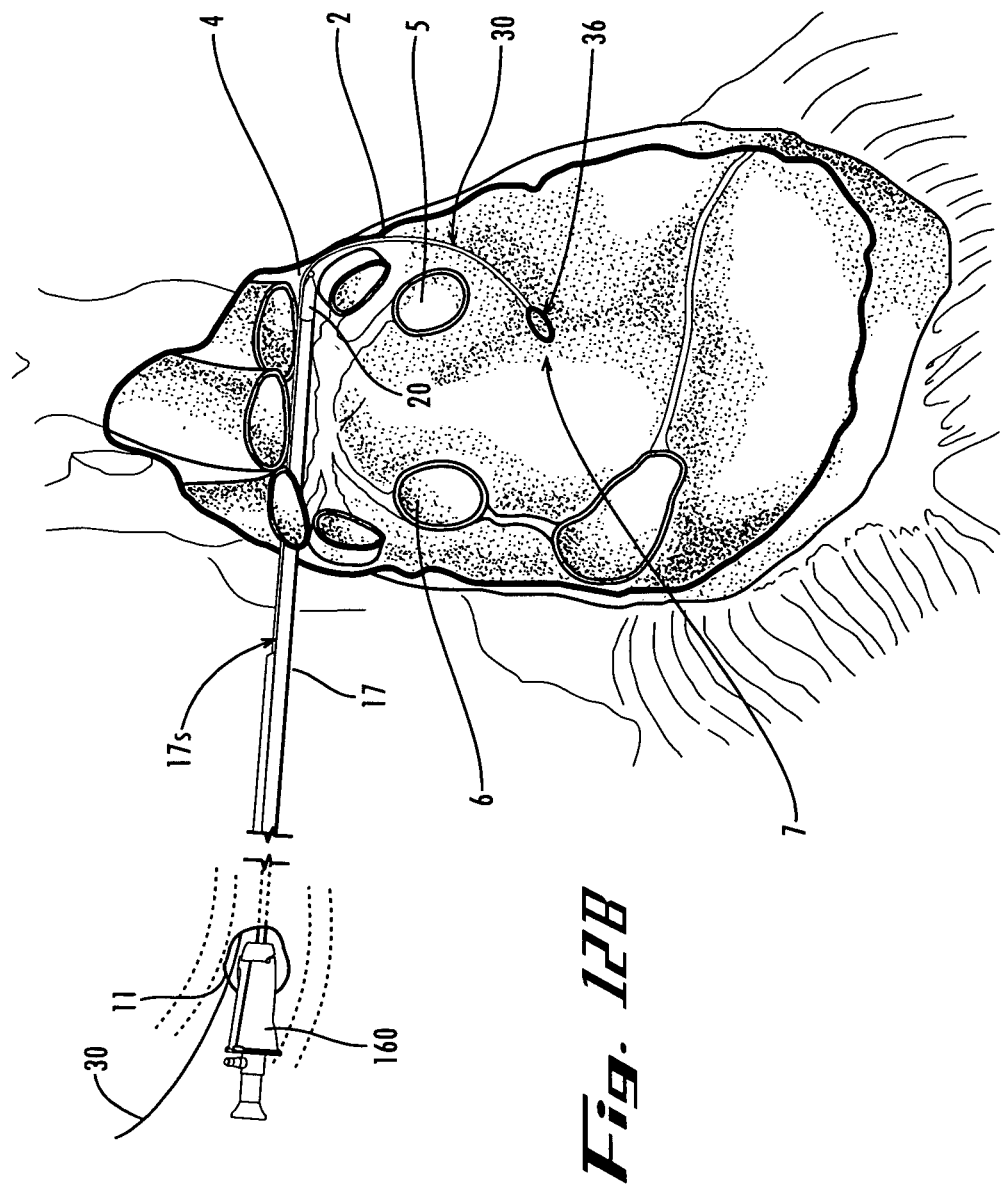

In FIG. 12A, as snare catheter 30 is being distally advanced, the distal end of catheter 30 (i.e., snare loop 36) contacts against the pericardium 2 on, the left side of the heart, and upon further distal advancement of catheter 30, the distal end of catheter 30 and suture loop 36 are deflected downwardly and are further advanced, into the oblique pericardial sinus 7, which is a majority of the region shown just beneath the left 5 and right 6 pulmonary veins on the posterior aspect of the heart in FIG. 12B. As can be seen in FIG. 12B, catheter 30 at this stage has begun to encircle the pulmonary veins 5,6. At this stage, instrument 10 may be removed, while leaving snare catheter 30 in place.

Next, with catheter 30 remaining in place as shown in FIG. 12B, instrument 10 may be reinserted through opening 13 and used to dissect the pericardium at a location posterior to the inferior vena cava to form an opening to the oblique pericardial sinus. Alternatively, instrument 10 may be reinserted through opening 11 to perform this dissection in a similar manner. This is described in more detail in application Ser. No. 11/138,950. In either case, after the dissection instrument 10 may then be inserted into the oblique pericardial sinus 7. FIG. 12C shows instrument 10 having been inserted into the oblique sinus via opening 13. Insertion may be performed while viewing through the endoscope 16 to align tip 20 with suture loop 36. Upon successfully passing tip 20 through suture loop 36 as shown in FIG. 12C, the operator next applies traction to suture line 34, while holding catheter 30 stationary with respect to movement of the suture line 34. This causes suture loop 36 to cinch down as suture line 34 is pulled through the sliding knot of the suture loop 36. If the loop 36 is formed of NITINOL®, or other nickel-titanium alloy, no sliding knot is present, rather the loop diameter decreases by virtue of the loop being pulled into the catheter. This action is continued until suture loop 36 is in tight contact with device 10 proximal of tip 20, thereby effectively "lassoing" instrument 10. Note that since instrument 10 necks down just proximal of tip 20 as shown in FIGS. 1A and 1B, that suture loop is capable of maintaining a grip on device 10, even under tension. A lock (not shown) may be fixed to suture line or wire 34 in a position abutting the proximal end of catheter 30 to prevent catheter 30 from backsliding, as noted above, and particularly to prevent suture loop 36 from expanding.

Figure 12D:
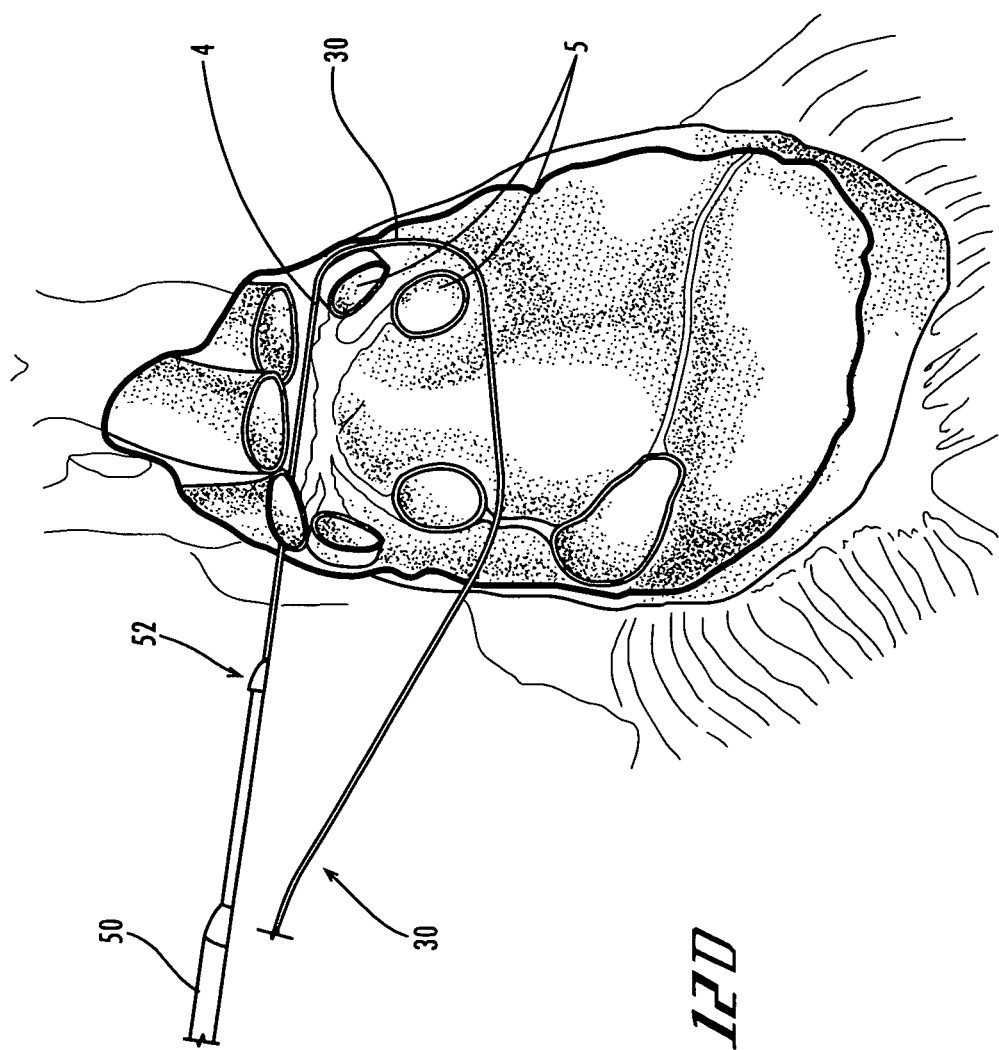

Once instrument 10 has been captured by suture loop 36, as described, instrument 10 is then withdrawn back out of the opening into which it was inserted, drawing suture loop 36 and the distal end portion of snare catheter 30 with it, out of the body. An ablation device 50 is fixed to the proximal end of suture line 34 (FIG. 12D), after removing the lock (if used). As one method, suture line 34 may be tied to a distal leader 52 of ablation device 50. A suitable ablation device that may be used as ablation device 50 is the Flex 10 microwave probe (Guidant Corporation, Santa Clara, Calif.), although the present invention is not limited to use of this product only. Other ablation devices configured to form a long linear lesion and which are sufficiently flexible to surround the pulmonary veins as described herein may be substituted. Further, the energy type for performing the ablation need not be microwave energy, but may alternatively be any of the other types of energy that have been used to form lesions (e.g., Rf, electrical, heat, chemical, ultrasonic, etc.).

Continued pulling on the distal end portion of catheter 30 draws catheter 30 further out of the opening which, as a consequence, draws ablation device 50 in through opening 11 and leads ablation device 50 around the pulmonary veins into the position previously occupied by catheter 30. At this stage, lesions can be formed by applying ablation energy through the ablation device 50 to ablate a pathway about three-quarters of the way around the pulmonary veins. Graspers or other instrument for use in an endoscopic environment can then be inserted through opening 11 and used to grasp the distal end of ablation device 50, and draw it superiorly so that it overlaps with the proximal end portion of the ablation device 50, thereby closing the loop around the pulmonary veins. The last quarter of the pathway can then be ablated to complete the formation of lesions all the way around the pulmonary veins. Alternatively, the overlapping procedure can be performed with the graspers prior to forming any lesions, and then lesions can be formed all the way around the pulmonary veins.

Prior to commencing ablation, adequate positioning/location of the ablation device 50 can be confirmed by maneuvering and viewing through device 10 at locations along the ablation device 50, relative to the tissues that the device is located along. After formation of the lesions and removal of the ablation device 10 can again be inserted through opening 11 and/or opening 13 to inspect the lesions to determine whether they have been adequately formed. If, upon inspection, it is determined that further ablation needs to be performed (such as when a continuous lesion has not been formed all the way around the pulmonary veins, or a portion of the pathway formed by the lesions has been inadequately formed, for example), then the ablation device may be reinstalled in at least the position where the further ablation is required, using the techniques described above, and additional ablation energy can be applied to the target location where it has been determined that further ablation is necessary. Re-inspection can be performed after this, using instrument 10 as described. This process can be iterated, if desired, until the surgeon is satisfied that the lesions have been adequately formed.

When using the Flex 10 or similar product, ablation device 50 may be actuated to incrementally form the lesion around the pulmonary veins, a segment at a time. For example, when using the Flex 10, a segment of tissue about one inch in length is ablated with each incremental ablation step. While the ablation device remains stationary, an antenna slides inside of it to change the location of tissue affected by energy emission from the antenna. The superior port 11 may be approximately 10 to 15 mm in diameter, and the inferior port 13 may be approximately 5 to 12 mm in diameter, but is typically about 5 mm in diameter.

Figure 13A:
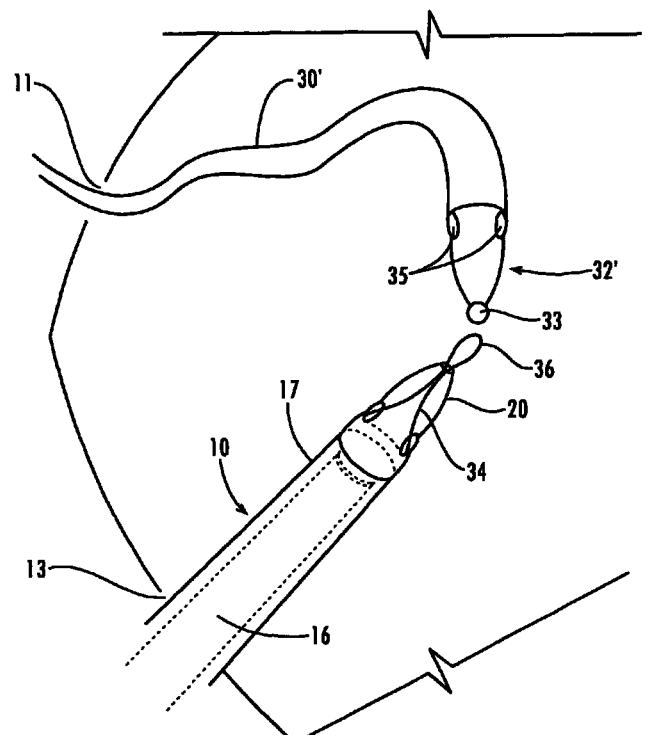
FIG. 13A illustrates an alternate arrangement of devices that may be used in a procedure like that described with regard to FIGS. 12A-12D, to route an ablation device in order to form an encircling pathway of lesions around the pulmonary veins.

FIG. 13A illustrates an alternate arrangement of devices that may be used in a procedure like that described above with regard to FIGS. 12A-12D, to route an ablation device 50 in order to form an encircling pathway of lesions around the pulmonary veins. In this example, catheter 30' is provided as a semi-flexible sleeve. Rigid tip 32' is provided with a ball-shaped end 33 that is configured to be engaged by a snare in a manner as described above. Rigid tip 32' and ball-shaped end are preferably made of a transparent plastic material to allow light to pass therethrough, and function as a lens for endoscope 16 as catheter 30' is installed as described below. One or more ports 35 may be provided in distal tip 32' which may be placed in fluid communication with a source of suction or irrigation via one or more lumens formed in the interior of flexible sleeve 30'.

Figure 13B:
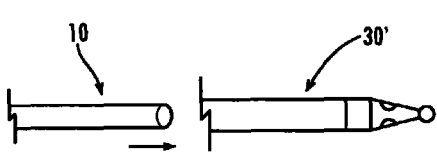
FIGS. 13B-13C show sliding the flexible device over a catheter for use in a procedure as described above with regard to FIG. 13A.
Figure 13C:
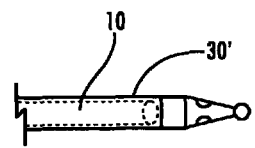

Catheter 30' is installed through opening 11 using instrument 10. Catheter 30' is configured and dimensioned to be slid over instrument 10 as illustrated in FIGS. 13B-13C. Once arranged as in FIG. 13C, catheter 30' is inserted through opening 11 and advanced to position ball-shaped end 33 superiorly of the left pulmonary veins and device 10 can then be withdrawn, leaving catheter 30' in position. Catheter 30', while being flexible enough to bend as it traverses around the pulmonary veins, has sufficient rigidity so that tip 32' can be distally advanced by pushing on a proximal portion of sleeve 30' from a location outside of the patient. As tip 32 is distally advanced, it (e.g., ball tip 33) contacts against the pericardium 2 on the left side of the heart, and upon further distal advancement of catheter 30', the distal end of catheter 30' (i.e., tip 32' and ball tip 33) are deflected downwardly and are further advanced, into the oblique pericardial sinus 7.

Next, device 10, having tip 20 installed thereon with sleeve 17 slid over the endoscope 16, as shown in FIG. 13A is inserted through an opening (13 or 11) and advanced into the oblique pericardial sinus to capture ball tip 33. This is illustrated in FIG. 13A. Upon successfully lassoing tip 32' with suture loop 36, suture loop 36 is retracted (slid proximally with respect to endoscope 16). As the proximal end loop of snare line 34 is fixed to sleeve 17 and snare line 34 is threaded through openings formed in tip 20 as shown in FIG. 13A, this action draws snare line into the distal opening of tip 20, thereby reducing the size of snare 36 and cinching the snare 36 around tip 32' in abutment against the proximal side of ball 33.

Once tip 32' has been captured by suture loop 36, as described, instrument 10 is then withdrawn back out of the opening into which it was inserted, drawing suture loop 36 and the distal end portion of catheter 30' with it, out of the body. The remainder of the procedure is the same as described above with regard to FIGS. 12C-12D. Alternative mechanisms may be provided for connecting instrument 10/instrument tip 20 with catheter 30/sleeve catheter 30' to perform the procedure described. For example, tip 32' may be provided with a pad of either the hook or loop portion of a hook and loop type fastening mechanism and tip 20 of instrument 10 may be provided with the opposite one of these. As another example, tip 20 and snare 36 may be provided with magnets on at least distal portions thereof that attract to one another when these component are brought near to one another.

Figure 14:
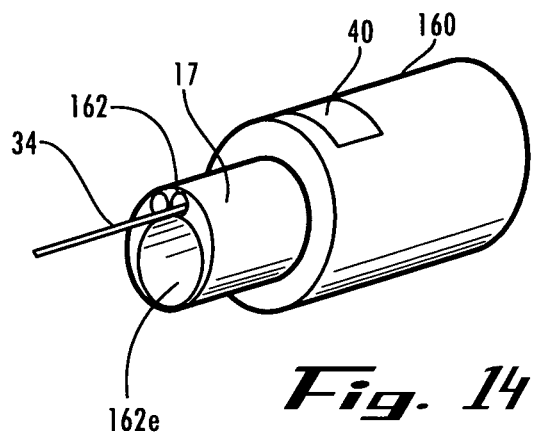
FIG. 14 illustrates one example of a lock, wherein an actuator is provided to be slid or rotated by an operator to tighten or loosen a clamp against a snare line.

As noted above with regard to FIG. 12C, a lock provided to fix suture line or wire 34 in a position to maintain the snare loop 36 cinched around the distal end portion of the catheter 30/sleeve catheter 30' to ensure that it maintains the connection as the catheter 30,30' is pulled out of the body. FIG. 14 illustrates one example of such a lock, wherein an actuator (e.g., thumb wheel) 40 is provided to be slid or rotated by the operator to tighten or loosen a clamp against snare line 34, thereby allowing snare line 34 to be slid relative to handle 160 when in the unlocked configuration, and locking the snare line 34 relative to the handle 160 when in the locked configuration.

Figure 15:
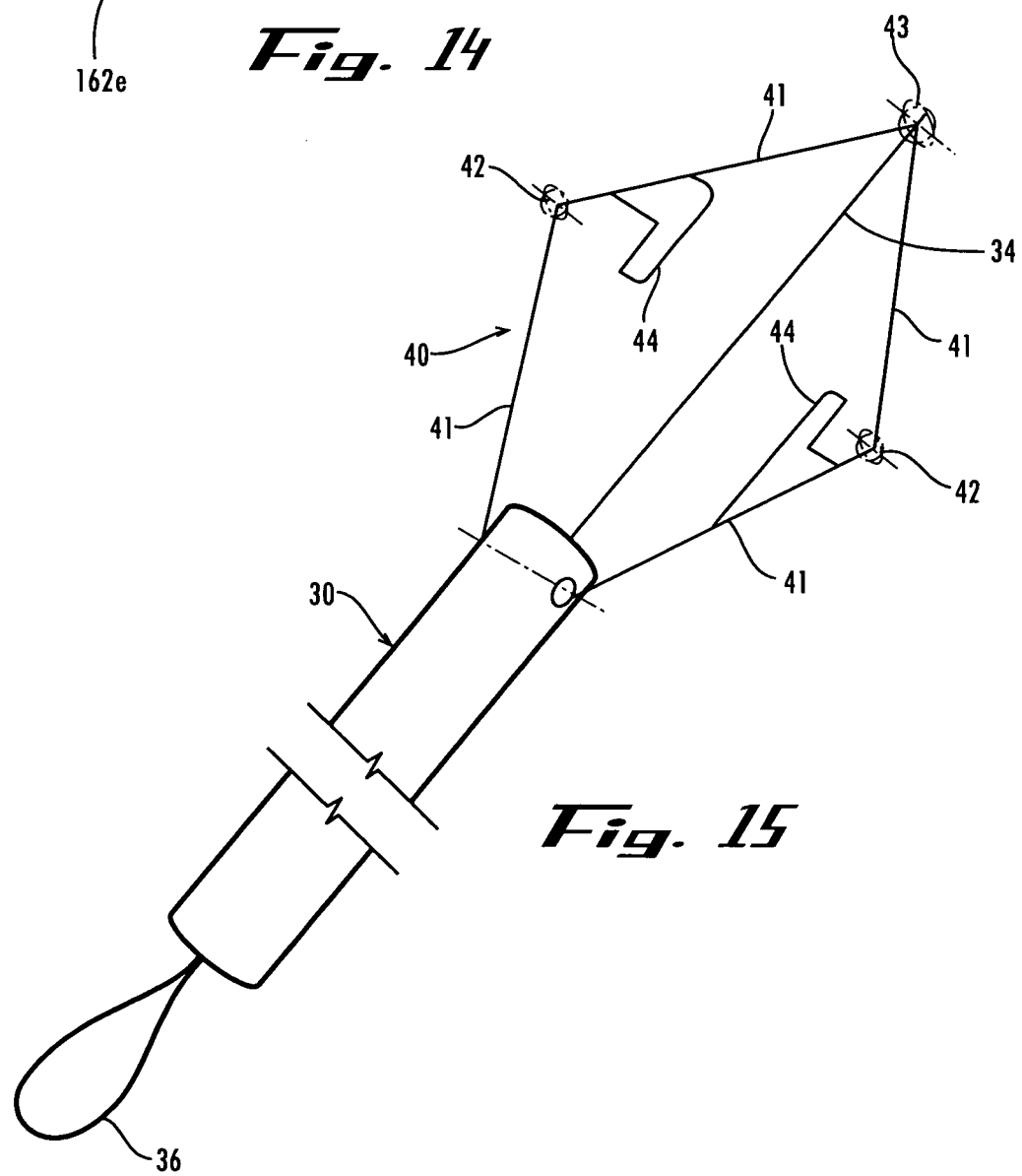
FIG. 15 illustrates an alternative locking mechanism that includes a four bar linkage.

FIG. 15 illustrates an alternative locking mechanism 40 that includes a four bar linkage mounted to a proximal end portion off snare catheter 30. Pairs of bars 41 are connected by pivot joints 42, with the two proximal-most bars 41 being joined by a third pivot joint 43. The proximal end of snare line 34 is also connected to this proximal joint 43. The distal-most bars 41 are pivotally mounted to a proximal end portion of snare catheter 30. Bars 41 are substantially rigid so that they do not bend significantly and thereby hold the intended position of the snare line 34. Lock 40 has an unlocked configuration as shown in FIG. 15 and a locked configuration. To lock the mechanism, the operator holds catheter 30 and pulls on pivot joint 43. This causes pivot joints 42 to move toward one another until locking clasps 44 push past one another. The extending arms of locking clasps deflect as they make contact with one another, allowing them to push past each other. Upon cessation of pulling on joint 43 and thus release of the pressure on pivot points 42, the extending arms of the locking clasps contact one another, thereby locking the locking mechanism in the locked configuration. In the locked configuration, bars 41 are more nearly aligned with the longitudinal axis of catheter 30. This extends the length of snare line 34 between the proximal end of catheter 30 and pivot joint 43, causing a withdrawal of snare line 34 and a portion of snare 36 into the distal end of catheter 30, thereby cinching down the size of snare 36. To unlock the mechanism, joint 43 is again pulled causing the joints 42 to again push towards one another, and then joint 43 is quickly released. When joint 43 is pulled, the locking clasps 44 are pushed beyond contact with each other thereby releasing their engagement. The segments 41 are biased toward the open position, such as by forming them from leaf springs biased to the open configuration, for example. The momentum generated by quickly releasing the pivot joints 43 allows clasps 44 to deflect and push past one another allowing the bars 41 to spring open to the open position shown in FIG. 15, as bars 41 are spring biased toward the open configuration. In one alternative configuration, the pair of bars on each side of snare line 34 may be replaced by a single spring steel band that is biased to the open configuration. This would also eliminate the pivot joints 42.

Figure 16A:
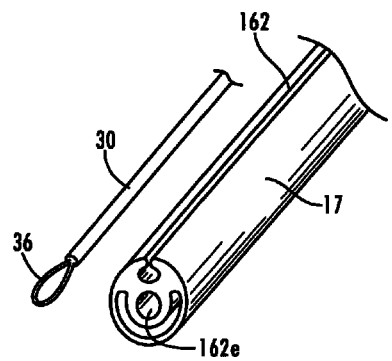
FIG. 16A-16B illustrate a partial perspective view and cross-sectional view of an alternative arrangement for releasing a snare catheter from a device.
Figure 16B:
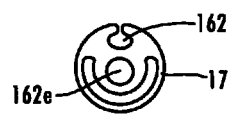

FIGS. 16A-16B illustrate an alternative arrangement for releasing snare catheter 30 from instrument 10 once snare has been placed into the transverse pericardial sinus as described above. In this arrangement, lumen 162 formed to receive snare catheter 30 is formed as a slot or groove that is configured to form a friction fit with snare catheter 30 upon receiving snare catheter 30 therein. FIG. 16B shows a cross sectional view of tube 17. At least the portion of tube surrounding groove 162 is formed of an elastomer, so that the opening that runs longitudinally of tube 17 can expand to receive or release snare catheter 30. Once installed, slot 162 maintains snare catheter 30 therein firmly. To release the snare catheter 30, snare catheter may be "peeled out" or "unzipped" from slot 162 starting from the proximal end portion, where the operator pulls the proximal end of snare catheter 30 out of slot 162 and this motion propagates to the distal end of snare catheter 30, thereby releasing snare catheter 30 from tube 17.

Figure 17A:
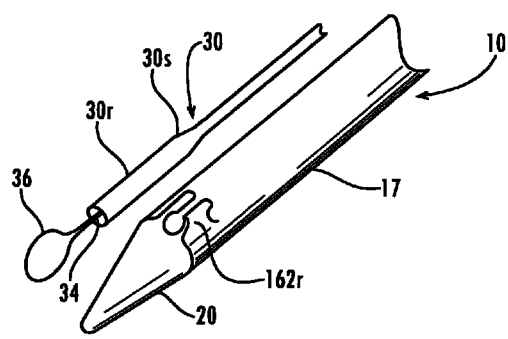
FIGS. 17A-17C illustrate another alternative arrangement for releasing a snare catheter from an instrument/device.
Figure 17C:
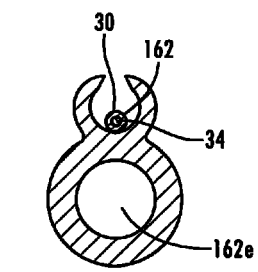
Figure 17D:
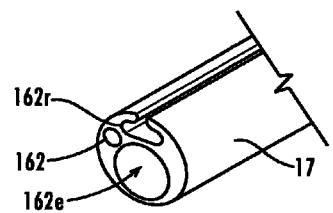
Figure 17B:
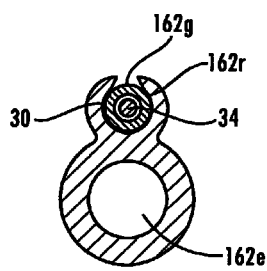

FIGS. 17A-17C illustrate another alternative arrangement for releasing snare catheter 30 from instrument 10. In this arrangement, lumen 162 is formed by a retaining eyelet 162r that extends radially from tube 17 and forms lumen 162 with a slot configuration (see the cross-sectional views of FIGS. 17B and 17C). Eyelet 162r may be formed of an elastomer, or from a more rigid polymer, or even metal, as it functions differently from the slot described above with regard to FIG. 16A. In this arrangement, snare catheter 30 includes a distal end portion 30r that has a larger outside diameter than the outside diameter of the remainder of the catheter 30. The outside diameter of end portion 30r is configured to form a friction fit with the inside diameter of lumen 162 formed by eyelet 162r. The gap 162g forming the slot in lumen 162 is wider than the outside diameter of the portion of snare catheter 30 that is proximal of the enlarged distal portion 30r. The outside diameter of snare catheter 30 is ramped or tapered 30s to transition the outside diameter from the main portion of catheter 30 to the enlarged distal portion 30r and to facilitate the loading and release functions of this arrangement.

To load or install catheter 30 on tube 17 so that it is fixed to tube 17, catheter 30 (the smaller diameter portion) is passed through gap 162g, as illustrated in the cross-sectional view of FIG. 17C. Catheter 30 is then retracted relative to tube 17 (e.g., by pulling on the proximal end portion of catheter 30 while holding tube 17 relatively fixed) to slide enlarged portion into a frictional fit with lumen 162, as illustrated in the cross-sectional view of FIG. 17B. In this arrangement, snare 36 and catheter 30 can be delivered to the transverse pericardial sinus, in a manner as described above. To release catheter 30 from the device, the operator can push on the proximal end portion of catheter 30 while holding the device (including tube 17) relatively motionless. This pushes enlarged distal portion 30r out of contact with lumen 162 and aligns a smaller outside diameter portion of catheter 30 with gap 162g as illustrated in FIG. 17C. At this time, catheter 30 can be lifted out through gap 162g, thereby releasing catheter 30 from tube 17 of device 10.

Figure 17E:

FIGS. 17D-17E illustrate a modification of the arrangement shown in FIGS. 17A-17C. In this arrangement, a keyed socket 162r is provided at a distal end portion of tube 17. A matching key 30r is provided to extend radially from a distal end portion of catheter 30. Key 30r is configured to form a friction fit with socket 162r when drawn into socket 162r by proximally pulling key 30r into socket 162r from a position distal of the opening of 162r. To release catheter 30, catheter 30 is pushed in the distal direction to drive key 30r out of contact with socket 162r.

Figure 18A:
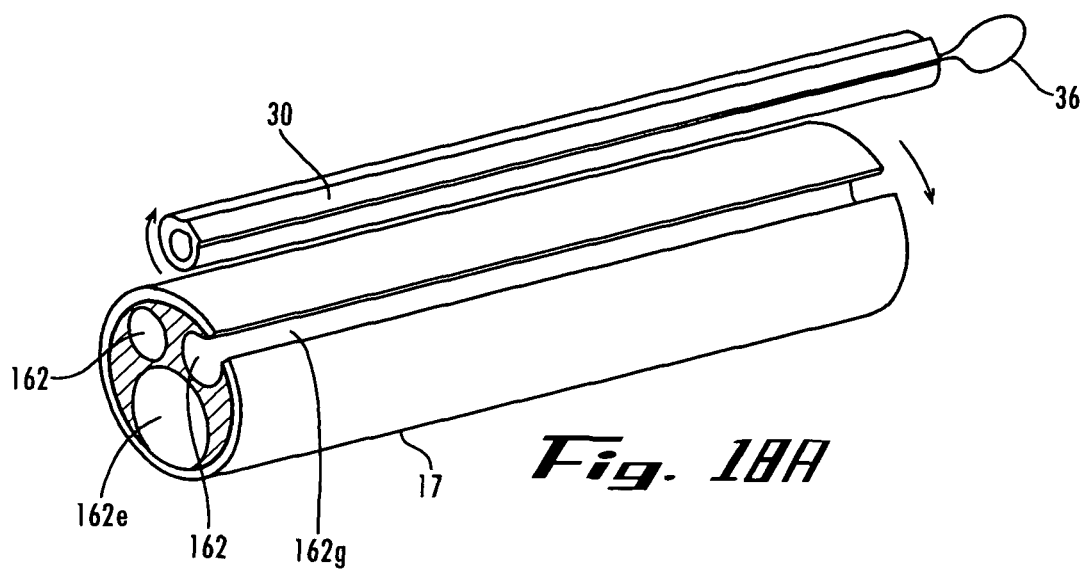
FIGS. 18A, 18B and 18C illustrate a released view, a captured view, and a cross-sectional view of the captured view of another quick release arrangement allows a snare catheter to be rapidly separated from a device.
Figure 18B:
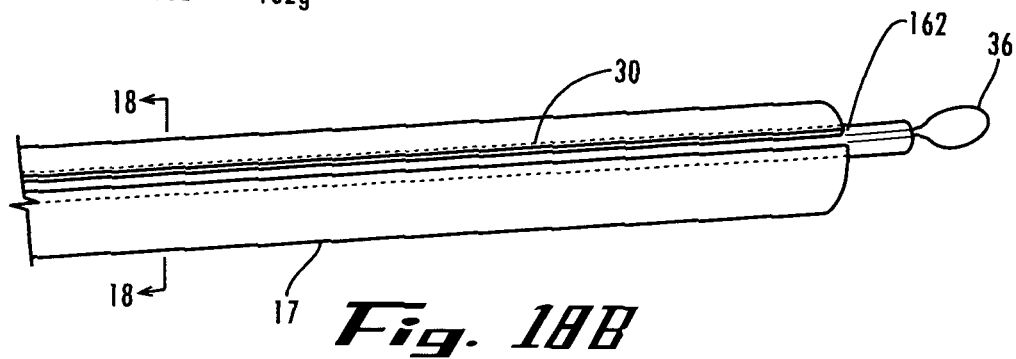
Figure 18C:
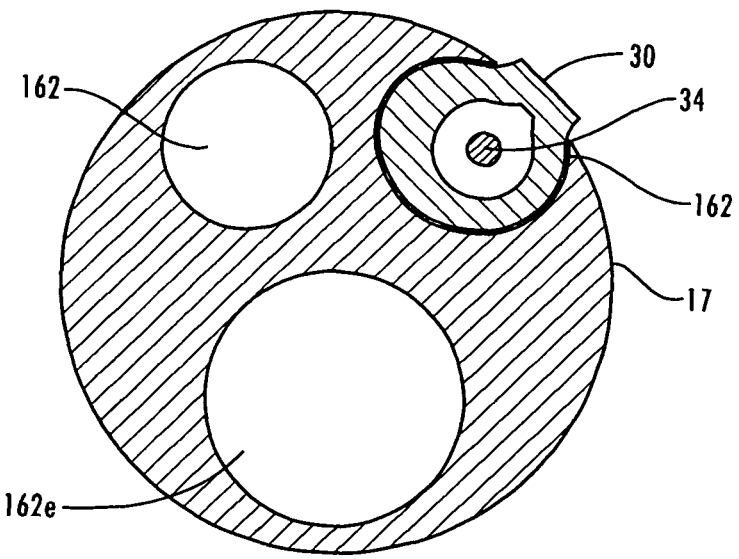

FIGS. 18A-18C illustrate another quick release mechanism that allows snare catheter 30 to be rapidly separated from tube 17 of device 10. In this arrangement, the lumen 162 configured to receive snare catheter 30 is slotted, as by gap 162g that has a sufficient width to allow snare catheter 30 to be rotated into lumen 162 in the direction of rotation indicated by the arrows in FIG. 18A. Both the lumen 162 and snare catheter 30 are asymmetrical in cross section, so as to define a cam surface circumferentially. These surfaces are matching so that the surface of catheter 30 follows the surface of lumen 162 as snare catheter 30 is rotated into place. Removal of catheter 30 from tube 17 occurs in the same manner, only by rotating catheter 30 in the opposite direction. FIG. 18B illustrates snare catheter 30 installed in tube 17 and FIG. 18C shows a cross sectional illustration of this taken along line 18-18.

Figure 19:
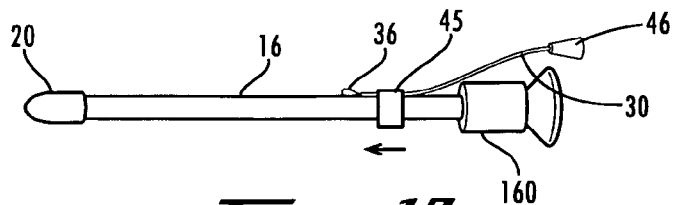
FIG. 19 illustrates an arrangement where a ring or sleeve is provided over the shaft of an endoscope so as to be freely slidable with respect thereto, and a snare catheter is releasably fixable to the ring or sleeve.

FIG. 19 illustrates an arrangement where tube 17 is done away with altogether. In this arrangement, a ring or sleeve 45 is provided over the shaft of endoscope 16 so as to be freely slidable with respect thereto. Snare catheter 30 is fixed to ring 45, such as by a releasable locking mechanism, e.g., a mechanism like that in FIG. 18A, or alternative. Endoscope 16 can be first inserted to perform the dissections, etc, and placed into the transverse pericardial sinus. Then a snare catheter 30 and ring 45 can be advanced distally over endoscope 16 to position snare 36 as desired. Catheter 30 can then be released from ring 45, such as by rotating it for example. Optionally, a rigid wire release mechanism 46 may be provided to run within or alongside of catheter 30 to the attachment to ring 45, which can be torqued to aid in the release function, and then withdrawn.

Figure 20B:
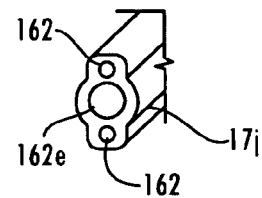
FIG. 20B is a perspective view of one of the jigs shown in FIG. 20A.
Figure 20A:
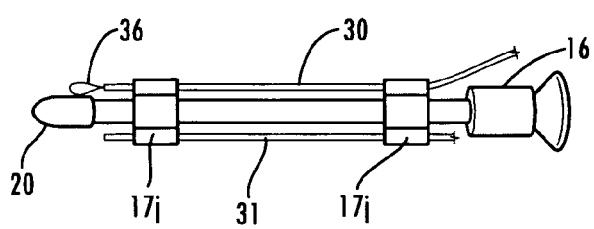
FIG. 20A illustrates another arrangement, wherein one or more jigs are provided through which a snare catheter or other tube or tool, and endoscope are passed.
Figure 20C:
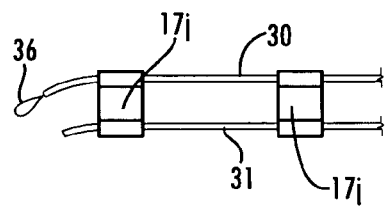
FIG. 20C shows the assembly of FIG. 20C without the endoscope.

FIGS. 20A-20C illustrate another arrangement that does not require tube 17. In this arrangement, one or more (typically two, although more or fewer may be used) jigs 17 are provided through which snare catheter 30 another tube 31 (which may function to deliver suction, irrigation, or delivery of other tools), and endoscope 16 are passed. Catheter 30 and tube 31 may form a friction fit with the lumens 162 though which they are passed, but endoscope shaft 16 is freely slidable within lumen 162e. In this way, once snare 36 has been placed in a desired location (e.g., transverse pericardial sinus), endoscope 16 can be withdrawn from lumens 162e and from the patient, leaving catheter 30 and tube 31 in place, held in their relative positions by jig(s) 17j, see FIG. 20C.

Figure 21A:
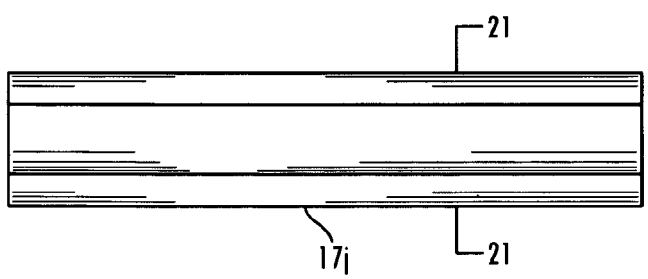
FIGS. 21A-21B illustrate a plan view and sectional view of a jig, wherein lumens formed in the jig are provided with slots or gaps that allow a snare catheter and/or other tools, and endoscope to be snapped in and out for rapid exchange.
Figure 21B:
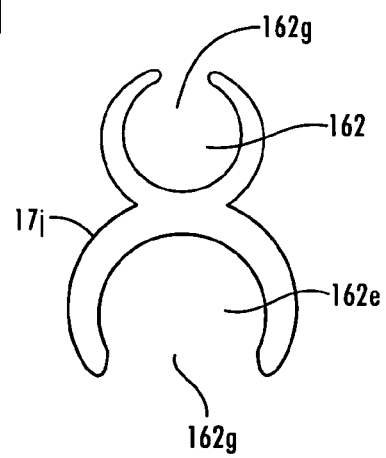

FIGS. 21A-21B show another jig arrangement 17j wherein the lumen 162 formed in jig 17j are provided with slots or gaps 162g that allow the snare catheter 30 and endoscope 16 to be snapped in and out for rapid exchange. Note that although jig 17*j* is shown as a single elongated jig, that a pair or more of similar, shorter jigs may be provided and snapped into place, in relative locations along the catheter 30 and endoscope 16 like that shown in FIG. 20A. Also, neither this jig 17*j* nor the jig 17*j* of FIG. 20A is limited to two lumens, as one or more additional lumens 162 may be provided for a suction line or other tube or instrument, for example.

Figure 22:
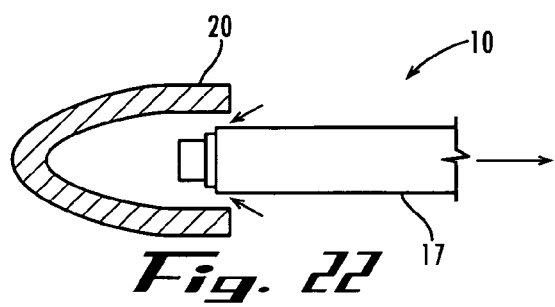
FIG. 22 illustrates a modification of a connection of a tip to a device that allows diffuse suction to be applied.

FIG. 22 illustrates a modification of a connection of tip 20 to device 10 that allows diffuse suction to be applied. In this arrangement, the inside diameter of the proximal opening of tip 20 is greater than the outside diameter of tube 17. Tip 20 may be mounted to tube 17 by a series of circumferentially spaced struts that extend radially from the distal end portion of tube 17, thereby maintaining a gap between the proximal end of tip 20 and the distal end of tube 17. Thus, when suction is applied through tube 17, fluid drawn through the gaps between tip 20 and tube 17 as indicated by the arrows in FIG. 22.

Figure 23A:
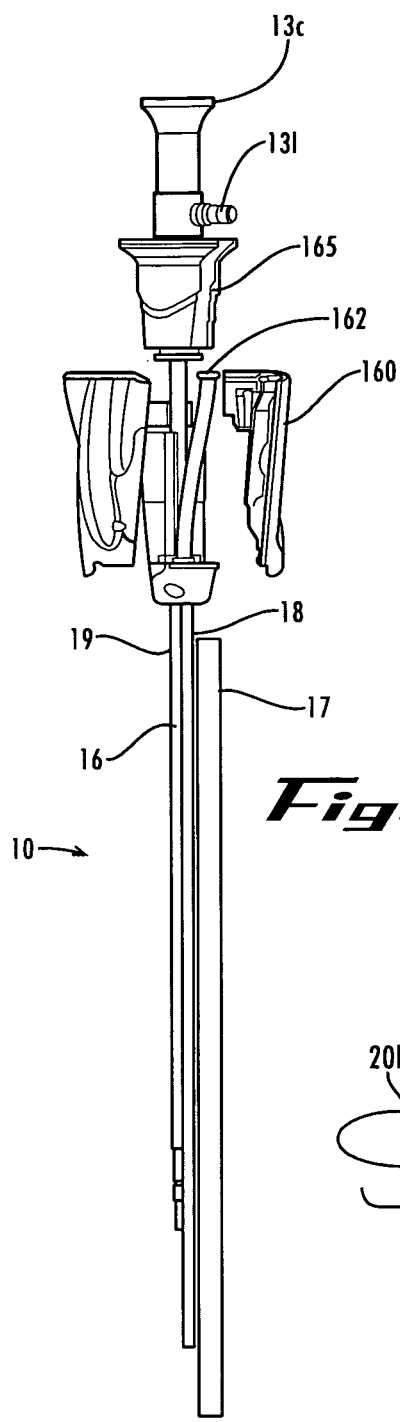
FIG. 23A shows an exploded view of another example of a device in accordance with an embodiment of the present invention.
Figure 23B:
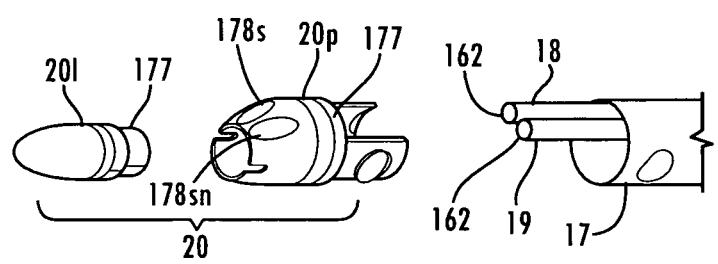
FIG. 23B is a partial, exploded view of the distal end portion of the device shown in FIG. 23A.

FIG. 23A shows an exploded view of another example of a device 10 in accordance with the present invention. Device 10 includes a bell 165 and handle 160 that attaches to tube 17 to receive endoscope 16 therein. Tube 17 thus functions as a cannula and is typically rigid, e.g., stainless steel or other metal tube or rigid polymer. Two service ports 162 are provided by tubes 18,19 received within tube 17, such as stainless steel hypotubes, for example (see the partial exploded view in FIG. 23B). Alternatively, only one such service port, or more than two service ports may be provided in the same manner. An example of an endoscope 16 that may be received in device 10 is the Guidant 7 mm Extended Length Endoscope, model FGVH-1111 (Guidant Corporation, Santa Clara, Calif.). A camera attachment 13*c* is provided at the proximal end of endoscope 16 for connecting a camera thereto, and a light source attachment 131 extends out from a proximal end portion of endoscope 16 for attachment to a light source via fiber optic cable. Bell 165 has the capacity to rotate about 300 degrees relative to handle 160 and tube 17, thus allowing a secure grip of the endoscope 16 at the endoscope's light source port 131. Service ports 162 are typically about 1 mm to about 6 mm in inside diameter, more typically about 1.5 to 3 mm inside diameter. In at least one embodiment, service ports are about 2 mm inside diameter and allow for passage of surgical tools (e.g., suction assembly, snare catheter (also referred to as routing snare), snare retrieval tool, graspers, etc.) therethrough to deliver the working ends of such tools out to the distal end of the device 10 through openings 178*s* and 178*sn*, respectively. Tube 17 is typically about 28-40 cm in length, more typically about 32-35 cm, but may be made to be longer or shorter as desired. Typically, tube 17 has an inner diameter in the range of about 9-12 mm, more typically about 10.3-10.9 mm. It should be noted that tube 17 is fixed by handle 160, thereby preventing it from rotating with respect to handle 160. For example, pins inside the handle halves of handle 160 may be provided to engage holes (not shown) through the wall of tube 17 thereby fixing tube 17 with respect to handle 160. This type of engagement is the same as that described with fixing tip 20 to the distal end of tube 17 (e.g., see FIG. 2B).

Distal tip 20 in this case includes lens 201 that is fixable to distal end piece 20*p* that includes the distal ends 178*s*,178*sn* of the service ports that are in fluid communication with lumens 162 when tip 20 is installed on tubes 17,18,19. Distal end piece 20*p* may be molded of rigid plastic or made of metal. Upon installation, the distal ends of tubes 18,19 are received in lumens 178*s*,178*sn* and distal end piece 20*p* may be connected to tube 17 in a manner described above with regard to FIG. 2B or by friction fit, or adhesives, or other fixation expedient. Lens 201 may be threaded to distal piece 20*p* or friction fit or otherwise mechanically connected for removability, but in the example shown, is fixed to distal end piece 20*p* via adhesive. A seal 177 may be provided to form an airtight seal between lens 201 and distal piece 20*p* in the same manner that seal 177 forms a seal between distal piece 20*p* and tube 17. Alternatively, only one seal 177 may be provided between components 201 and 20*p*, with no seal provided between components 20*p* and 17.

Lens 201 is optimized to provide visualization in the presence of an air space as well as in a fluid environment and in direct contact with tissue. The air chamber inside lens 201 is sealed via seal 177 to avoid fluid ingress and minimize fogging.

Figure 23C:
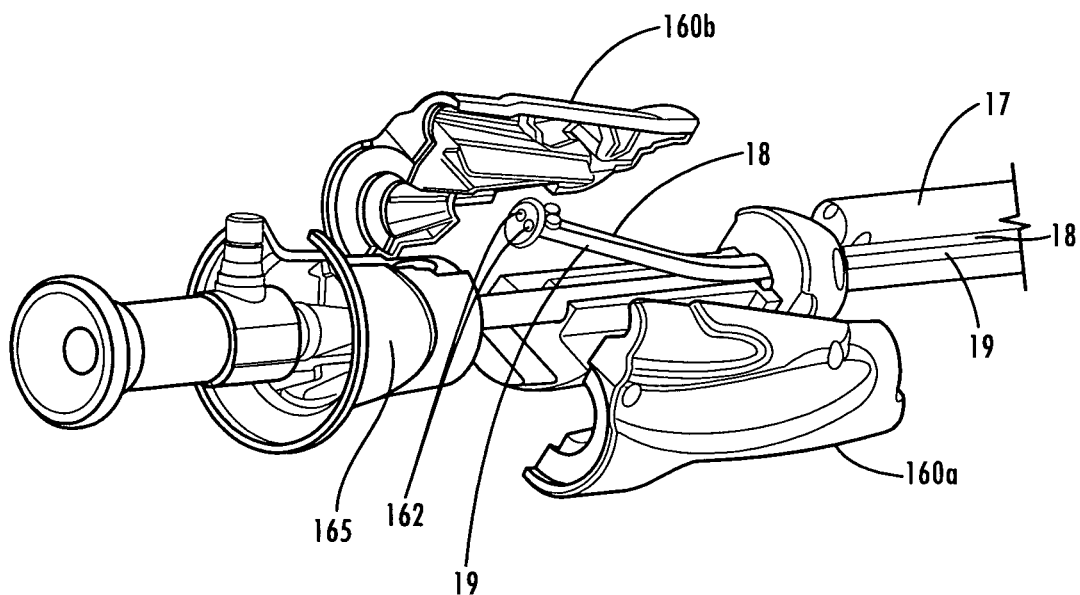
FIG. 23C is a partial, exploded view of the proximal end portion of the device shown in FIG. 23A.

FIG. 23C shows a proximal portion of the device 10 shown in FIG. 23A, with handle 160 in an exploded view, and tube 17 disassembled for a better view of tubes 18,19. The proximal ends of lumens 162 are shown at the proximal ends of tube 18,19, which are securely held in the recesses provided in handle halves 160*a*,160*b*. These are the locations at which tools are inserted for delivery of the working ends of such tools out of openings 178*s*, 178*sn*.

The boundaries of all components of device 10 that are to be inserted into the patient have been designed to be atraumatic and there are no sharp edges or abrupt transitions in these components in the assembled state. All components of device 10 of FIGS. 23A-23C may be mechanically connected, except that tip 201 is adhered to distal end 20*p*, as noted.

Figure 24:
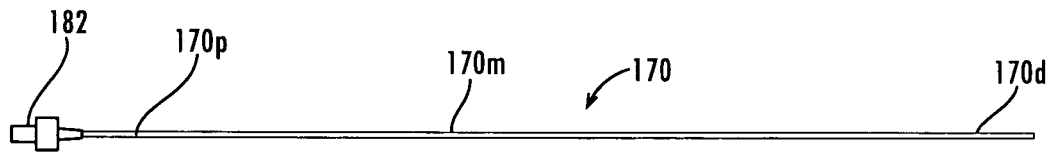
FIG. 24A illustrates another example of a snare catheter, which is also referred to as a "routing snare" tool.
FIG. 24B shows distal and proximal end portions of the snare routing tool shown in FIG. 24A.

FIG. 24 shows a suction assembly 170 that is configured and dimensioned to be slid through either of the service ports 162 in device 10. Suction assembly 170 may be provided with unlimited ability to slide through a lumen 162, or, alternatively, may be limited to a predefined range of motion by anchoring suction assembly 170 to handle 160 with a tether (not shown). A luer connector 182 (in this example, a female luer connector, although a male luer connector or other type of connector may be used) is provided at the proximal end of suction assembly 170 for connection of the assembly to a source of vacuum. A luer connector provides compatibility with most typical operating room vacuum sources. The main body of the suction assembly 170 may be provided with varying degrees of rigidity along its length. For example, the proximal end portion 170*p* may be rigid, such as a metal hypotube, for example, to facilitate the attachment of the connector 182 and to make it easier for an operator to grip the tube. The middle portion 170*m* of the tubing may be a plastic tubing that is flexible enough to easily traverse the shallow curvature of the hypotubes 18,19 of the service ports 162, but rigid enough to permit the tool to be advanced and retracted by pushing and pulling on the proximal end portion of tube 170 without elastic response. The distal portion 170*d* of tube 170 is still more flexible to provide atraumatic interaction with the tissues of the patient, yet stiff enough to maintain an open passage for vacuumed fluids. In this regard, distal portion is relatively short to prevent it from collapsing upon itself under strong vacuum. For example, the length of distal portion 170*d* may be from about 0.05" to about 0.75", typically about 0.30". Optionally, the tube structure of distal portion 170*d* may be provided with small side holes (not shown) extending through the wall of the tube to further assist in preventing the distal portion from collapsing upon itself when under strong vacuum. Distal portion 170*d* may also be colored with a color that provides great contrast relative to the patient's tissue so that it can be easily viewed and located in the view through the endoscope.

Figure 24A:
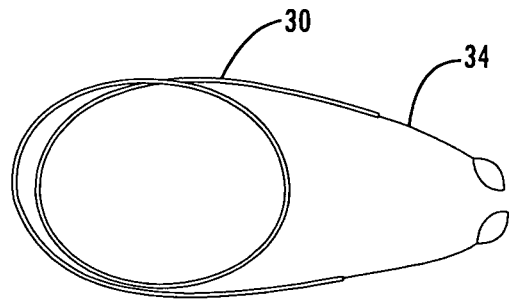

FIG. 24A illustrates another example of a snare catheter, which is also referred to as a "routing snare" tool. This example is configured and dimensioned to be slide through either of the lumens 162 in device 10 of FIG. 23A. The outer tubing, catheter or outer sleeve 30 is also referred to as the snare guide 30 and is made of a flexible plastic, e.g., high density polyethylene, or other flexible plastics that have been mentioned above. Snare guide 30 may have a length on the order of 28 to 60 inches, typically about 30 to 40 inches, but may be made longer if desired. The outside diameter of snare guide 30 may be in the range of about 0.070 to about 0.100 inches, typically about 0.076 to about 0.090 inches. The inside diameter of snare guide 30 may be in the range of about 0.040 to about 0.70 inches, typically about 0.048 to about 0.058 inches. Both ends of snare guide 30 may be chamfered to make them less traumatic to the anatomy during insertion of either end into a patient, and easier to advance through a cannula, such as lumen 162, for example, as well as easier to navigate in the surgical site. The average wall thickness of snare guide is in the range of about 0.010 to about 0.020 inches, typically about 0.015 inches to provide for a strong wall that can receive the snare assembly without failure. This thickness of the wall also provides sufficient column strength to allow it to be advanced through lumen 162 and the anatomy by pushing on a proximal portion of snare guide 30 that is outside of these structures, without buckling of the snare guide 30. Snare guide 30 may also be colored with a color (e.g., bright orange) that provides great contrast relative to the patient's tissue so that it can be easily viewed and located in the view through the endoscope.

Figure 24B:
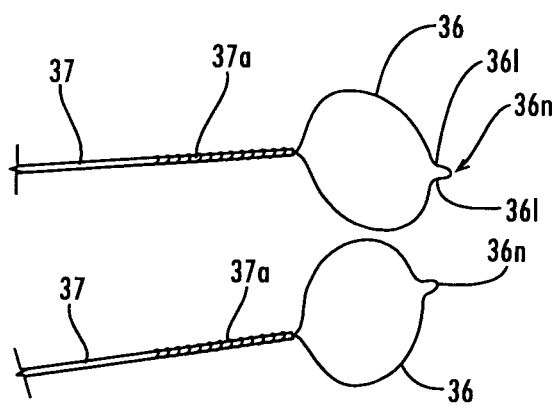

The snare assembly is made up of the snare line 34, e.g., a core mandrel of nickel-titanium alloy, which may have a diameter of about 0.020 to about 0.025 inches, in one embodiment, about 0.023±0.004 inches. The mandrel ends may be ground down to a smaller diameter (e.g., in one embodiment, to about 0.018±0.003 inches) over a length of about four to ten inches at each end to increase maneuverability, both by the smaller diameter and by the increased flexibility that results from the smaller diameter. Snare loops 36 are provided at both ends of the snare line and may be formed of braided nickel-titanium wire formed by standard nickel-titanium shape memory metal processing. Upon braiding and shaping the material into the form of snare loops 36, at the ends of each loop 36, a long straight portion of the loop material is left extending from the braided loop. These two long straight portions are paced in contact with the core mandrel of the snare line 34 for connection therewith. Snare loops 36 are maintained in connection with snare line 34 by Fluorinated Ethylene-Propylene (FEP) heat shrink tubing 37 (outer heat shrink tubing) that is shrunk over the extensions from the loops 36 that are in contact with the mandrel when the heat shrink tubing is applied, see FIG. 24B. The strength of the bond between snare 36 and mandrel 34 allows for tension loads to exceed six to nine pounds prior to failure, typically about nineteen to twenty-four or more pounds force. Heat shrink tubing 37 may have a shrink factor of about 1.5 to 1.7:1. In one embodiment the shrink factor is about 1.6:1. Heat shrink tubing 37 may extend about six to fourteen inches from the ends of the mandrel toward the middle, typically about nine to eleven inches. The wire that forms the snare loops 36 extends about 1-/2 to two inches, typically about one inch, beyond the end of the mandrel 34 and heat shrink tubing 37 before bending to form the loop. An inner heat shrink tubing 37a may be provided over the parallel wires that form both ends of the loop 36. Inner heat shrink tubing may have a shrink factor of about 1.2 to 1.4:1, typically about 1.3:1. The transition between outer 37 and inner 37a heat shrink tubes is made atraumatic by fusing the tubes together. The inner heat shrink tubing 37a may be color coded so that a user can easily and immediately differentiate between the proximal and distal snares 36, especially in the case where both snares 36 (i.e., both ends of the snare assembly) are fed through a common port or incision in the patient (e.g., opening 11). For example, in FIG. 24B, the heat shrink tubing 37 adjacent the distal snare 36 is clear and the heat shrink tubing 37 adjacent the proximal snare 36 is black. Of course, other colors may be substituted. For example, white and black may be used to provide maximum contrast. Black and green, or some other color combination may alternatively be used. Typically, the color combination chosen will provide sufficient contrast or color distinction to accomplish the intended function.

The wire from which snares 36 are made may be a braided wire. Mandrel 34 is typically formed as a single rod or wire. In one embodiment, the wire is a seven strand braid of Nitinol® (nickel-titanium alloy) and is about 0.012±0.003 inches in diameter, with each strand being approximately 0.0035 inches in diameter. In one embodiment, snare loop 36 defines an angle relative to mandrel 34 of about 29±14 degrees. At this transition, a large radius of curvature of about ½ to 1.5 inches is defined. The profile of snare loop 36 can be substantially round or oval. The diameter or length may be about 0.4 to 1.2 inches, typically between about 0.6 and 0.9 inches. All curves on the snares (loops) 36 are gentle and composed of large radius curvature. The snares 36 may be provided with a kink or nipple 36n that may facilitate capturing a ball tip or other object to be lassoed. Kink or nipple 36n helps reduce local stresses at the tip. The kink is not provided with a sharp tip to avoid stress concentration and potential failure of such a sharp tip. Nipple or kink 26n distributes the loads and bend angles of the shape memory material in the loop 36, so that there is no location in the loop that is bent beyond its plastic deformation limit. Kink or nipple 36n may comprise substantially parallel legs 361 that are about 0.06±0.05 inches apart, typically about 0.06±0.02 inches apart, and about 0.06±0.05 inches long, typically about 0.06±0.02 inches long, and join at the distal end of nipple 36n in along a tangent radius to the loop.

The materials of the snare guide 30 and snare assembly allow it to be sterilized under gamma ray irradiation, ethylene oxide sterilization, or other known methods of sterilization.

FIGS. 25A-25C show a snare capture tool 100 that is configured and dimensioned to be deployed through either of lumens 162 in device 10 of FIG. 23A. Snare capture tool may be deployed into service port 162 at the proximal end of either tube 18 or 19 and delivered through either opening 178s or 178sn and placed for capture by snare loop 36 similar to the way that tip 20,20',22 was described as being captured above. Thus, device 10 of FIG. 23A does not require the use of a ball-ended tip, as a bullet-shaped tip or other shape optimized for viewing can be used as snare capture tool 100 is used to capture snare loop 36.

At the proximal end of snare capture tool 100 a grip or handle 102 may be provided to facilitate handling and operation of the tool 100 by a user. An elongated metal wire mandrel 104 (e.g., stainless steel, nickel-titanium alloy or other biocompatible metal, typically stainless steel) extends from grip 102 at the proximal end of tool 100 to ball 106 at the distal end of tool 100, which it typically welded to mandrel 104. Ball 106 may be made from the same material as mandrel 104 and is typically stainless steel. A polymeric layer 108 is formed over the majority of mandrel 104 which increases the diameter of the main body, but is still a small enough diameter to pass freely through lumen 162. Layer 108 may be made from high density polyethylene, or other flexible plastics that have been mentioned above. The thickness of layer 108 maintains the mandrel centered inside lumen 162 and provides added stability to ball 106 and bare mandrel 104 at the distal end portion of tool 100 during use.

A spring 110 is provided over layer 108 and abuts a portion of grip 102 at a proximal end thereof. Spring 110 has a diameter that prevents it from entering lumen 162. Thus, when tool 100 is inserted into service port 162 it can be advanced until the distal end of spring 110 abuts the service port 162 at the proximal end of either tube 18 or tube 19. In this position, ball 106 is positioned just inside of lumen 178s or 178sn, and the bare portion of mandrel 104 is retained within lumen 162. Upon pushing grip 102 to compress spring 110, ball 106 and the bare portion of the mandrel 104 are extended out of opening 178s or 178sn (as well as past the distal end of tip 20, so as to be in a working configuration. Layer 108 may be color coded to visually differentiate it from the color of the snare guide. Upon release of the grip 102, spring 110 expands, drawing the distal end of tool 100 back into lumen 162, into a stowed configuration.

In the working configuration, ball 106 can be maneuvered into position to be lassoed by snare loop 136 or ball 106 can be maneuvered to "spear" through the opening in snare loop 136, after which snare loop 136 can be cinched down to perform the capture. The "bare" portion of the mandrel 104 that exists between ball 106 and the distal end of layer 108 provides a reduced diameter (less than that of ball 106 and less than that of layer 108) that provides a contact area on which snare loop 136 may be cinched down against. After cinching, the cinched snare is prevented from sliding off the distal end of tool 100 by the larger diameter of ball 106 and is prevented from sliding proximally along tool 100 by the shoulder formed by the distal end of layer 108 which has a larger diameter.

In one use of device 10 and associated tools described above with regard to FIGS. 23A-25C, device 10, with suction assembly 170 inserted through one of the service ports/lumens 162 is placed under direct visualization through opening 11 on the ride hand side of the patient's chest. Tip 20/device 10 is then advanced over the collapsed right lung and through an opening (e.g., incision) formed in the pericardial sac and into the transverse pericardial sinus. Suction may be applied continuously, intermittently, or on an as needed basis during these procedures via suction assembly 170 that is connected to a source of suction. After the inside surface of the pericardial sac at the left side of the patient's heart is visualized through endoscope 16 (and tip 20), routing snare 30 (snare guide and snare assembly) are inserted into the available service port 162. Snare 30 is advanced beyond the distal end 20 of device 10 under visualization via endoscope 16 and tip 20. Snare mandrel 34 flexes as snare 36 contacts the internal surface of the pericardial sac and advances toward the apex of the heart, around the left pulmonary veins, as the snare catheter assembly 30 is further distally advanced. Device 10 is then removed out of opening 11 while maintaining the snare guide and snare assembly 30 in position.

Device 10 is then reintroduced into the surgical area by passing it in through opening 13. Note that, in an alternative procedure, device 10 may be reinserted through opening 11 to perform this part of the procedure. Note further, that for embodiments where snare catheter is provided for rapid exchange/release from tube 17, that device 10 does not even need to be completely removed from opening 11 prior to continuing with this part of the procedure. In this case, device 10 is inserted through opening 13 and tip 20 is advanced into the pericardial sac and traversed to the oblique sinus 7. Device 10 and routing snare 30 are manipulated until the distal end of routing snare 30/snare 36 are visible via endoscope 16. At this time, snare capture tool 100 is introduced into the available service port 162 and advanced through lumen 162. By compressing spring 110, ball 106 and bare mandrel portion 104 extend past distal tip 20 and ball 106 is inserted through the opening in snare 36. Snare mandrel 34 is then retracted proximally while holding snare guide 30 in place to reduce the diameter of the loop of snare 36 thereby cinching snare 36 against the bare mandrel portion 104. The cinched snare may be locked in position using any of the locking mechanisms described above. Alternatively, a surgeon may simply clamp the snare mandrel 24 where it extends proximally from the proximal end of snare guide, using a hemostat or other common surgical clamp to prevent mandrel 34 from sliding distally with respect to snare guide 30. Next, device 10 is withdrawn from the opening, thereby bringing snare capture tool 100 and snare assembly 30 with it, and routing the snare assembly/routing snare 30 further around the pulmonary veins.

Once the distal end of the routing snare 30/snare loop 36 is outside of the patient's body, snare 36 is released (such as by unlocking the locking mechanism and pulling proximally on the snare guide) and removed from contact with the snare capture tool 100. The ablation device is next connected to the proximal end of the snare assembly 30. Device 10 can optionally be reintroduced into the patient to confirm, under direct visualization though device 10, adequate placement of the routing snare 30 prior to placing the ablation tool 50 using routing snare 30. In one embodiment, sutures extending from the ablation device 50 are tied to the proximal snare loop 36 of the snare assembly 30. The color coding of the shrink layers 37a may be used to ascertain that the connection is being made to the proximal snare 36. Once the sutures are tied, snare 36 is cinched down on the tied sutures to further secure the connection. The distal end portion of the snare routing assembly 30 is then pulled out of the patient, thereby routing the ablation device around the pulmonary veins. After the distal end of ablation device 50 is pulled out of the patient, the routing snare assembly 30 is disconnected from the ablation device, such as by reversing the connection procedures, or by cutting the connecting sutures. Device 10 can then be reinserted through opening 11 and or opening 13 to visually inspect the placement of the ablation device 50 prior to applying ablation energy. The rest of the procedure is the same as that described above with regard to FIGS. 12A-12D. After forming lesions, device 10 can again be reinserted to inspect the lesions formed to see if the ablation has been adequately performed to complete the electrical isolation of the pulmonary veins.

Figure 26C:
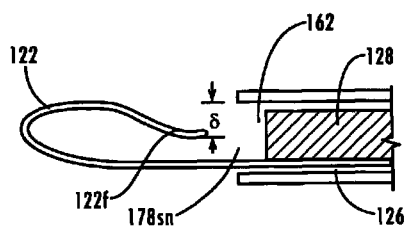
FIG. 26C illustrates a partial view of a hook tool in an alternative configuration.

FIGS. 26A-26C illustrate another tool 120 that may be used with device 10. Tool 120 is a slender, elongated retrieval hook tool configured and dimensioned to be slid though lumen 162. The distal end of hook tool 120 comprises a hook 122 that can be used to capture snare 36. Thus, hook tool 120 may be used as an alternative to snare capture tool 100 to capture snare 36 in the performance of a procedure, such as the procedure described above for example. Retrieval hook tool 120 is configured and dimensioned to be deployed through either of lumens 162 in device 10 of FIG. 23A. Retrieval hook tool 120 may be deployed into service port 162 at the proximal end of either tube 18 or 19 and delivered through either opening 178s or 178sn and used to hook snare 36.

At the proximal end of hook tool 120 an actuator or handle 124 may be provided to facilitate handling and operation of the tool 120 by a user. An elongated metal wire mandrel 126 (e.g., stainless steel, nickel-titanium alloy or other biocompatible metal, typically stainless steel) extends from actuator 124 at the proximal end of tool 120 to hook 122 formed at the distal end of tool 120. Hook 122 may be made from the same material as mandrel 126 and is typically bent or shaped from the same, such as a stainless steel wire, either round or flat, for example. A polymeric layer 128 may optionally be formed over the majority of mandrel 104 which increases the diameter of the main body, but is still a small enough diameter to pass freely through lumen 162. Layer 128 may be made from high density polyethylene, or other flexible plastics that have been mentioned above. The thickness of layer 128 maintains the mandrel centered inside lumen 162 in the configuration shown in FIG. 26A and provides added stability to hook 122 at the distal end portion of tool 120 during use.

A spring 110 is provided over mandrel 126 (and over layer 128 when used) and abuts a portion of actuator 124 at a proximal end thereof. Spring 110 has a diameter that prevents it from entering lumen 162. Thus, when tool 120 is inserted into service port 162 it can be advanced until the distal end of spring 110 abuts the service port 162 at the proximal end of either tube 18 or tube 19. In this position, hook 122 is positioned just inside of lumen 178s or 178sn, and the bare portion of mandrel 126, just proximal of hook 122 is retained within lumen 162. Upon pushing actuator 124 to compress spring 110, hook 122 and the bare portion of the mandrel 126 just proximal of hook 122 are extended out of opening 178s or 178sn (as well as past the distal end of tip 20, so as to be in a working configuration. Upon release of the actuator 124, spring 110 expands, drawing the distal end of tool 120 back into lumen 162, into a stowed configuration.

In the working configuration, hook 122 can be maneuvered into position to hook snare 36 to perform the capture, as illustrated in FIG. 26B. The "bare" portion of the mandrel 126 that exists between hook 122 and the distal end of layer 128 provides a reduced diameter and facilitates guiding the wire of snare 36 between the arms of hook 122 during the hooking procedure.

FIG. 26C illustrates a partial view of hook tool 122 in an alternative configuration. In this configuration, mandrel 126 is offset within layer 128 to minimize the likelihood of the free end 122f of hook 122 from catching on the wall of the distal end portion 20p (or other tube through which the hook tool 120 is inserted) upon retraction of the hook 122. By offsetting mandrel 126, the free end 122f is offset by a distance δ from the wall of lumen 162.

Figure 27A:
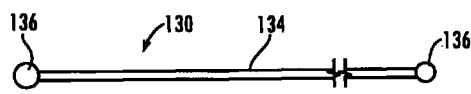
FIG. 27A illustrates a bolo tool that may be used in place of a snare assembly for routing an ablation device around the pulmonary veins.

FIG. 27A illustrates a bolo tool 130 that may be used in place of snare assembly 30 for routing an ablation device around the pulmonary veins. Bolo tool 130 is configured and dimensioned to be slid through either of the lumens 162 in device 10 of FIG. 23A. Tool 130 is typically made to have a length of about 28 to 60 inches, typically about 34 to 40 inches, but may be made longer or shorter if desired. The extended, slender body 134 of bolo tool 130 may be made as a core mandrel of solid or braided wire, e.g., from stainless steel or nickel-titanium alloy, or other biocompatible metal. A ball 136 is provided at each end of the bolo tool 130 may be formed of the same material from which mandrel 134 is formed. The materials of the bolo tool 130 allow it to be sterilized under gamma ray irradiation, ethylene oxide sterilization, or other known methods of sterilization.

Figure 27B:
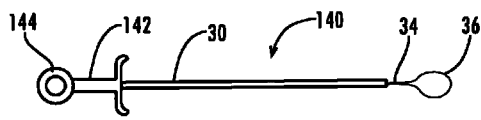
FIG. 27B shows a retrieval tool that may be used to retrieve the bolo tool shown in FIG. 27A.

In use, bolo tool 130 may be placed in the same manner that snare assembly 30 is placed, as described above. Once the distal ball 136 has been placed in the oblique sinus 7, device 10 is inserted to advance the distal tip 20 into the oblique sinus. A trigger snare tool (retrieval tool) 140 (see FIG. 27B) is provided to be placed to retrieve the bolo tool 130. Note that, alternatively, snare assembly 30 may be used to retrieve bolo tool 130. Trigger snare tool 140 includes a snare 36 at its distal end connected to a proximally located handle 144 via mandrel 34. The majority of mandrel 34 may be surrounded by a snare guide 30. The snare 36, mandrel 34 and snare guide may be made the same as that described above with regard to the snare assembly. In tool 140, trigger 142 is slidably positioned over handle 144. A spring (not shown) biases trigger 142 distally from handle 144 to cause snare guide 30 to translate distally with respect to mandrel 34, thereby cinching down the size of snare loop 36. In FIG. 27B, tool 140 is shown in the uncinched or open configuration, which is achieved by the operator squeezing trigger 142 back proximally against the handle 144. Upon release of the trigger 142, the spring drives trigger 142 and snare guide 30 distally with respect to handle 144 and mandrel 34.

Figure 27C:
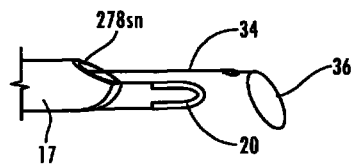
FIG. 27C illustrates a distal end portion of a retrieval tool.

Snare 36 may be formed (such as by shape memory setting, or mechanical deformation) so that when trigger 140 is retracted to the open configuration, snare 36 deploys at a predetermined acute angle with respect to the longitudinal axis of mandrel 34, as shown in FIG. 27C, e.g., less than about 30 degrees, typically about 15 to 25 degrees. This angulation places snare 36 more directly in the field of view of the endoscope 16 through tip 20.

Figure 28A:
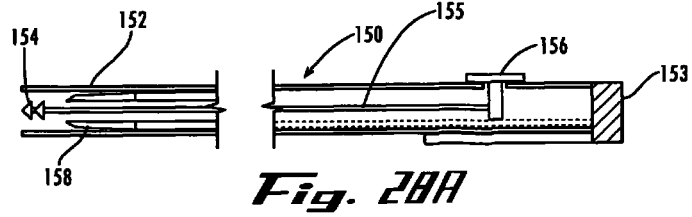
FIG. 28A illustrates a perforation tool that may be used to perforate the pericardial sac prior to introduction of a device therethrough.

FIG. 28A illustrates a perforation tool 150 that may be used to perforate the pericardial sac prior to introduction of device 10 therethrough, for example. Perforation tool 150 is configured and dimensioned to be slid through either of the lumens 162 in device 10 of FIG. 23A for use therewith. A protective sheath 152 is provided to surround the working components of tool 150 as it is traversed through a lumen 162. Sheath 152 has a limited amount of flexibility to manage the curvature of the lumens 18, 19, and may be made of plastic, e.g., HDPE. A needle (or barbed needle, as shown) 154 is provided at a distal end portion of tool 150 and is connected to actuator 156 via needle shaft 155. Actuator 156 is slidable with regard to sheath 152 so that sliding of actuator 156 distally relative to sheath 152 drives needle 154 distally of the distal end of sheath 152. In the case of a needle, this action can be used to perforate the pericardium. In the case of a barbed needle 154, this action pierces the pericardium. Upon retraction of actuator 156 (i.e., sliding it proximally with respect to sheath 152) the barb(s) of barbed needle 154 retains the pericardium and draws it against cutter blade 158 mounted within tool 150, to cut a larger hole in the pericardium. Optionally, cutter blade 158 may be connected to a second actuator 153 at the proximal end portion of tool 150 that may be rotated or oscillated to increase the cutting action of blade 158 against the pericardial tissue. Tool 150 may also be used for dissecting through the pericardial reflections.

Figure 28B:
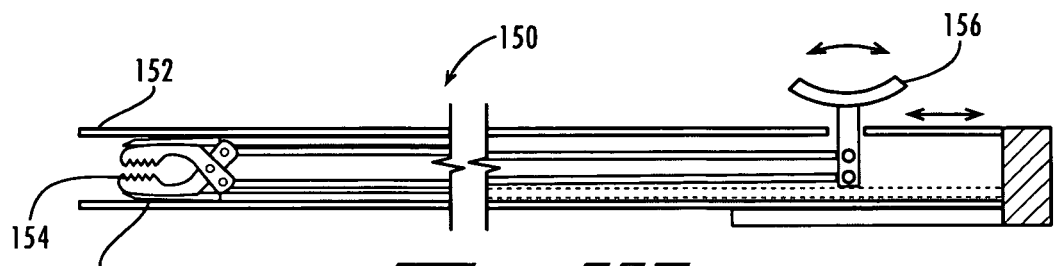
FIG. 28B shows an alternative arrangement of a perforation tool in which graspers are provided to grasp the pericardial tissue, to draw it back against a cutter blade to form an opening in the pericardial tissue.

FIG. 28B shows an alternative arrangement of a perforation tool 150 in which graspers 154 are provided to grasp the pericardial tissue, to draw it back against cutter blade 158 to form the opening in the pericardial tissue. Perforation tool 150 is configured and dimensioned to be slid through either of the lumens 162 in device 10 of FIG. 23A for use therewith. Graspers 154 are mechanically linked to actuator 156 which is slidable with respect to sheath 152 to advance the graspers distally out of sheath 152 and to retract graspers 158 back into sheath 152 to pull the tissue against cutter 158. Actuator 156 also rocks with respect to sheath 152 (see rotational arrows) to operate the opening and closing of the jaws of grasper 154. Tool 150 may also be used for dissecting through the pericardial reflections.

Figure 28C:
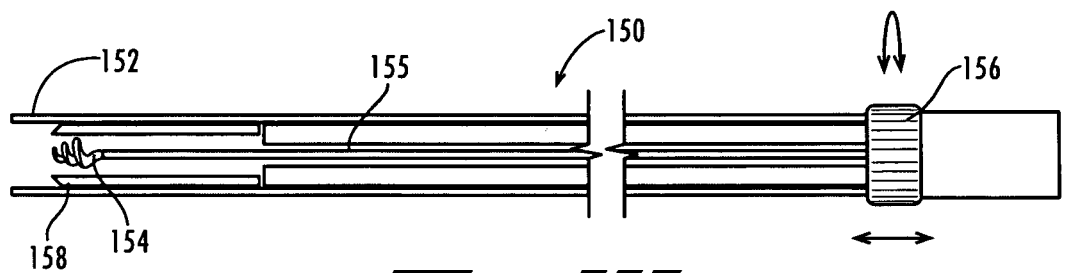
FIG. 28C shows another alternative arrangement of a perforation tool, wherein the grasping implement provided in this example is a cork screw configuration, which can be screwed into the pericardial tissue to grasp or secure it, to draw it back against a cutter blade.

FIG. 28C shows another alternative arrangement of a perforation tool 150 in which the grasping implement 154 provided in this example is a cork screw configuration, which can be screwed into the pericardial tissue to grasp or secure it, to draw it back against cutter blade 158 to form the opening in the pericardial tissue. Perforation tool 150 is configured and dimensioned to be slid through either of the lumens 162 in device 10 of FIG. 23A for use therewith. Cork screw tip 154 is mechanically linked to actuator 156 via rod 155. Actuator 156 is slidable with respect to sheath 152 to advance the cork screw tip 154 distally out of sheath 152 and against the tissue to be grasped, and to retract cork screw 154 back into sheath 152 to pull the tissue against cutter 158. Actuator 156 is also rotatable to drive the screwing of the cork screw into the tissue to be perforated. Actuator may be slid distally with respect to sheath 152 at the same time that it is rotated to help drive the cork screw tip 154 into the tissue. Tool 150 may also be used for dissecting through the pericardial reflections.

Figure 28D:
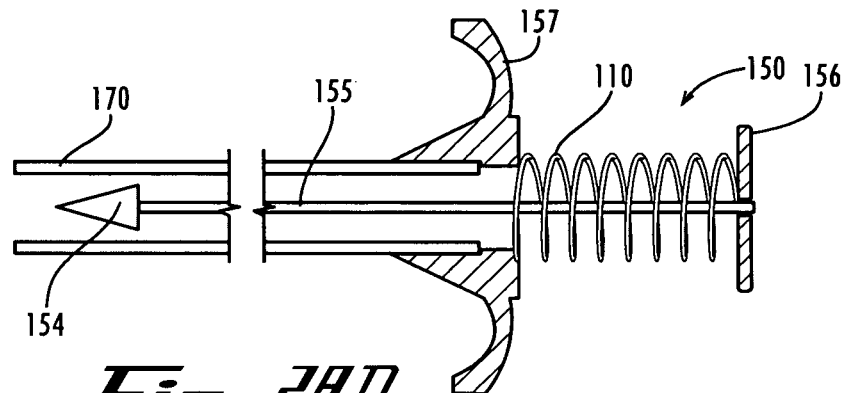
FIG. 28D shows another alternative arrangement of a perforation tool that may be used to form an opening in the pericardial tissue and/or used for dissection through the pericardial reflections.

FIG. 28D shows another alternative arrangement of a perforation tool 150 that may be used to form an opening in the pericardial tissue and/or used for dissection through the pericardial reflections. Perforation tool 150 is configured and dimensioned to be slid through either of the lumens 162 in device 10 of FIG. 23A for use therewith. Advantageously, tool 150 is also adapted to be delivered through suction assembly 170, or other catheter, for example. Thus handle 157 is configured to be mounted to a connector of a suction assembly (for example, by being fitted with the mating counterpart of luer connector 182). A spike 154, sharpened end of wire 155 or other sharpened feature configured to pierce through tissue upon an impulsive impact is provided at the distal end of shaft 155 which is connected proximally to actuator 156. In this example, actuator 156 is a plunger type actuator. Thus, upon pressing on actuator (e.g. with a thumb) while holding handle relatively stationary (such as by holding the finger grips with the fingers), tip 154 is impulsively driven into the pericardium or other tissue against which the tube 170 has been contacted to drive an opening through the tissue. Upon release of the actuator 156, spring 110 retracts tip 154 out of the tissue and back into tubing 170.

Figure 28E:
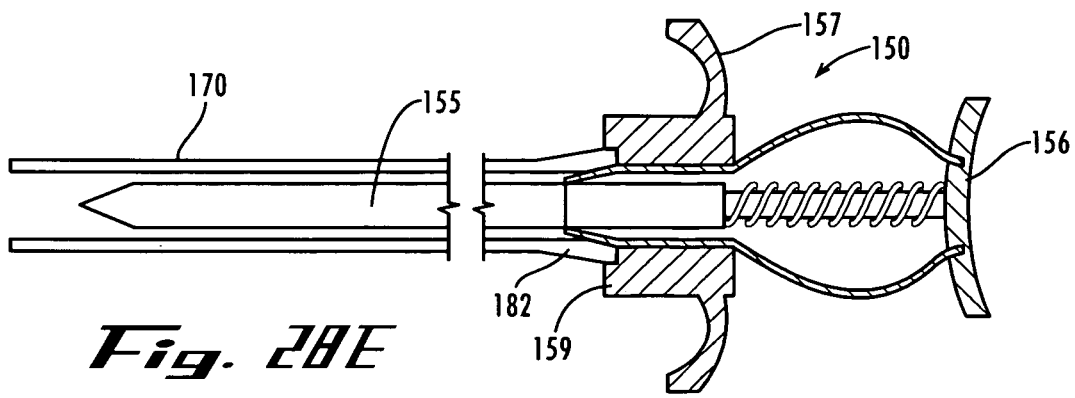
FIG. 28E shows still another alternative arrangement of a perforation tool that may be used to form an opening in the pericardial tissue and/or used for dissection through the pericardial reflections.

FIG. 28E shows another alternative arrangement of a perforation tool 150 that may be used to form an opening in the pericardial tissue and/or used for dissection through the pericardial reflections. Perforation tool 150 is configured and dimensioned to be slid through either of the lumens 162 in device 10 of FIG. 23A for use therewith. Advantageously, tool 150 is also adapted to be delivered through suction assembly 170, or other catheter, for example. Thus handle 157 is configured to be mounted to a connector of a suction assembly (for example, by being fitted with the mating counterpart 159 of luer connector 182). A sharpened end of shaft 155 is provided in this embodiment for piercing tissue. Alternatively, a spike, or other sharpened configuration may be provided. Shaft 155 is connected proximally to actuator 156. In this example, actuator 156 is a plunger type actuator. Thus, upon pressing on actuator (e.g. with a thumb) while holding handle 157 relatively stationary (such as by holding the finger grips with the fingers), tip 154 is impulsively driven into the pericardium or other tissue against which the tube 170 has been contacted to drive an opening through the tissue. Upon release of the actuator 156, spring 110 (in this example, a leaf spring) retracts tip 154 out of the tissue and back into tubing 170.

FIG. 29A illustrates a partial view of a mapping probe tool 210 that may be used to gauges the effectiveness of a lesion formed during an ablation procedure as described herein. Mapping probe tool 210 is configured and dimensioned to be slid through either of the lumens 162 in device 10 of FIG. 23A for use therewith. Optionally, tool 210 may also be adapted to be delivered through suction assembly 170, or other catheter, for example.

In the example shown, tool 210 is provided with a long slender tube 211 having sufficient length to simultaneously extend from both distal and proximal openings of lumen 162 of device 10. Optionally, tool 210 as shown in FIG. 29A, as well as any variations or other embodiments of mapping probe tool, may be provided with a handle at a proximal end thereof, such as a handle of the type described with regard to FIG. 25B, for example. Further optionally, a biasing member, such as a spring, may be provided to function in the manner described above with regard to spring 110 (FIG. 25B). That is, when biasing member is biased by driving the proximal portion of tool 210 distally, the probe mapping elements are extended distally from the distal end of lumen 162 (or suction tube or other catheter), and when this biasing is released, the biasing member draws the probe mapping elements back into concealment within the distal end portion of the vessel (lumen 162, suction tube or other catheter) through which the tool has been inserted.

Tube 211 is provided with at least a pair of probe mapping elements 212 on a distal end portion thereof. Probe mapping elements 212 may be provided as electrodes, for example, which are configured to emit an electrical signal as well as receive an electrical signal. Elements 212 are separated by a distance along the tube 210 that is configured to place the elements 212 on opposite sides of a lesion that has been formed by ablation. Typically, this distance is in the range of about 1 mm to about 20 mm. In one example, this distance is about 6 mm. An electrical wire 212 is connected to each mapping element 214, and wires 212 extend proximally through tube 210 and extend proximally out of tube to be connected to a power source and metering equipment so that the results of mapping can be measured. Alternatively, a solid rod may be substituted for tube 211, in which case, wires 214 can be run externally of the rod, and optionally fixed to the external wall of the rod, at one or a plurality of points along the length of the rod, or continuously over the length of the rod.

To perform a mapping procedure, after insertion of tool 210 through device 10 as described and positioned distally so that electrodes 212 are exposed, electrodes 212 are placed on opposite sides of a lesion in contact with tissues that have not been ablated. Then a signal is emitted through one of electrodes 212, while the opposite electrode is configured to receive the emitted signal. Depending upon the strength of the signal received, and potentially also a time delay from emission to reception, known electronic measurement equipment can indicate whether the lesion has been sufficiently formed. When a fully encircling lesion has been completed, there should be substantially no reception of a signal emitted from inside the circle, when attempting to receive it outside the circle, or vice versa. It is noted that electrodes 212 may be configured, so that the functions of the emitter and receiver electrodes may be readily switched, so that mapping can be conducted in either direction between the electrodes.

FIG. 29B shows a variation of the tool 210 of FIG. 29A. In this example, the distal end portion of tube or rod 210 is biased in the bent configuration shown. Bend 213 is configured to orient the distal end portion of tool 210 with respect to the remainder of the tool at an acute angle. Bend 213 is flexible, such as a living joint, or hinged and biased with a biasing member, so that the distal end portion of tool 210 may be substantially axially aligned with the remainder of the tool when it is inserted into lumen 162 or other catheter. When the distal end portion is passed distally out of the distal end of the lumen 162 or other catheter, the distal end portion of tool 210 then resumes its bent configuration. This bent configuration can facilitate the placement of the mapping elements 212 on opposite sides of a lesion, as the distal end portion of tool 210 is oriented more transverse to a lesion by the preconfigured bend.

FIG. 29C shows another variation of the tool 210 of FIG. 29A. In this example, the distal end portion of tube or rod 210 is preconfigured into a Y-shaped configuration, thereby separating elements 212 by a distance established between the open arms of the Y-shape, as shown. The open Y-shape configuration is the unbiased configuration, and is deformable (such as by biasing forces) to substantially align the open arms of the Y-shaped end so that they can be inserted into a lumen 162 or other catheter. In this regard, the Y-shaped end may be resilient and elastically deformable. Alternatively, the Y-shaped end may be hinged and biased to the open configuration, similar to the manner described with regard to bend 213 above in the bent configuration shown. In the closed configuration, Y-shaped end 215 has the arms substantially in a parallel configuration so that it can be passed through lumen 162 or other catheter. When the distal end portion 215 is passed distally out of the distal end of the lumen 162 or other catheter, the distal end portion 215 of tool 210 then resumes its open Y-shaped configuration as shown in FIG. 29C. This can facilitate the placement of the mapping elements 212 on opposite sides of a lesion, as the arms 215a separate the elements 212 upon the expansion to the open configuration.

FIG. 30 illustrates a partial view of a linear ablating probe tool 220 that may be used with device 10 to form a linear lesion. Linear ablating probe tool 220 is configured and dimensioned to be slid through either of the lumens 162 in device 10 of FIG. 23A for use therewith. Optionally, tool 220 may also be adapted to be delivered through another catheter, for example.

In the example shown, tool 220 is provided with a long slender tube 221 having sufficient length to simultaneously extend from both distal and proximal openings of lumen 162 of device 10. Optionally, tool 220 as shown in FIG. 30, as well as any variations or other embodiments of mapping probe tool, may be provided with a handle at a proximal end thereof, such as a handle of the type described with regard to FIG. 25B, for example. Further optionally, a biasing member, such as a spring, may be provided to function in the manner described above with regard to spring 110. In any case, an actuator 226, such as a triggering mechanism, button or other actuating mechanism may be provided to allow an operator to commence delivery of ablation energy to linear ablation element 222. When a biasing member such as spring 110 is employed, it can be biased by driving the proximal portion/handle of tool 220 distally. As a result the ablation element 222 extends distally from the distal end of lumen 162 (or suction tube or other catheter), and when this biasing is released, the biasing member draws the ablation element 222 back into concealment within the distal end portion of the vessel (lumen 162, suction tube or other catheter) through which the tool has been inserted. If such a biasing arrangement is not used, the positions of the ablation element 222 can be controlled by manually sliding the tool 220 distally and proximally, respectively, with respect to the vessel that it is inserted through.

Tube 221 is provided with at one ablation conduit 224 to deliver ablation energy to ablation element 222 from a location outside of the patient and proximal of tool 220. In the case where ablation element ablates via Rf energy, heat, ultrasonic or microwave energy, conduit 221 may comprise at least one electrical wire, for example. For chemical ablation, conduit may comprise a tube for delivery of a chemical. For laser ablation, conduit may comprise at least one light guide, such as one or more optical fibers, for example. Linear ablation element may be on the order of about 0.5" to about 2.0", typically about 1" in length. Alternatively, a solid rod may be substituted for tube 221, in which case, conduit 224 can be run externally of the rod, and optionally fixed to the external wall of the rod, at one or a plurality of points along the length of the rod, or continuously over the length of the rod.

To perform a linear ablation procedure, after insertion of tool 220 through device 10 as described and positioned distally so that linear ablation element 222 is exposed, ablation element 222 is contacted to tissue in the target location to be ablated. Then ablation energy is provided to linear ablation element 222, either by user actuation of actuator 226, or by actuation of an ablation energy source connected to conduit 224 and located proximally of tool 220. Ablation energy is applied, either continuously, or intermittently, until a sufficient lesion is believed to have been formed, which may be based on visual observation through device 10. Thereafter, the sufficiency of the lesion may be checked using tool 210 in a manner as described above. Reapplication of ablation energy may be performed, if necessary, as many times a necessary, in the manner described above, until a satisfactory lesion has been formed.

FIG. 31 illustrates a distal end portion of a point/disk ablation probe tool 230 that may be used with device 10 to form a point lesion. Tool 230 may be useful for connecting previously formed linear lesions, where a small gap of non-ablated tissue remains therebetween, for example, or to ablate an ectopic focus identified by mapping, for example. Point/disk ablation probe tool 230 is configured and dimensioned to be slid through either of the lumens 162 in device 10 of FIG. 23A for use therewith. Optionally, tool 230 may also be adapted to be delivered through another catheter, for example. Tool 230 may be constructed in any of the ways and to have any of the features described above with regard to tool 220, with the difference being at the distal end portion of tool 230. Thus, only the distal end portion of tool 230 is described here and illustrated in FIG. 31. Also, tool 230 may perform ablation using any of the different types of ablation energy described above with regard to tool 220.

An ablation probe point 232 is provided on the distal tip of the distal end portion of tube 231 and is connected via an ablation conduit 231 to the proximal end of tool 230 in a manner as described above with regard to conduit 221. Ablation probe point 232 is dimensioned to be about the same or less than the outside diameter of tube 221, although alternative embodiments can be formed as a disk that is slightly larger in diameter than the outside diameter of tube 221. In effect, point 232 is actuated to form a small lesion that is not extended substantially linearly. As such, point 232, although typically disk shaped or semi-spherical, need not be, but could be any other shape that does not have an elongated dimension.

To perform a point ablation procedure, after insertion of tool 230 through device 10 and positioning tool 230 distally so that ablation probe point 232 is exposed, ablation probe point 232 is contacted to tissue in the target location to be ablated. Then ablation energy is provided to ablation probe point 232, in any of the manners described above with regard to providing ablation energy to linear ablation element 222. Ablation energy may be applied, either continuously, or intermittently, until a sufficient point lesion is believed to have been formed, which may be based on visual observation through device 10. Thereafter, the sufficiency of the lesion may be checked using tool 210 in a manner as described above. Reapplication of ablation energy may be performed, if necessary, as many times a necessary, in the manner described above, until a satisfactory lesion has been formed.

FIG. 32 illustrates a distal end portion of a monopolar cautery tool 240 that may be used with device 10 to cauterize tissue. Tool 240 may be useful for creating openings, such as through the pericardium for example, and/or to cut through unwanted adhesions, or other tissue needing to be cleared to perform a procedure. Monopolar cautery tool 240 is configured and dimensioned to be slid through either of the lumens 162 in device 10 of FIG. 23A for use therewith. Optionally, tool 240 may also be adapted to be delivered through another catheter, for example. Tool 240 may be constructed in any of the ways and to have any of the features described above with regard to tool 220, with the differences being at the distal end portion of tool 240. Also, rather than an ablation conduit, tool 240 is provided with an electrical wire 244 to deliver electrical energy to the distal end of the tool. Thus, only the distal end portion of tool 240 is described here and illustrated in FIG. 32.

A monopolar cauterizing element (such as an electrode, for example) 242 is provided on the distal tip of the distal end portion of tube 241 and is connected via electrical wire 241 to proximal end of tool 240, where wire 241 extends proximally to be connected to a power source that supplies the cauterizing energy. Alternatively, tool 240 may be modified to provide a bi-polar cauterizing system, as would be readily apparent to those of ordinary skill in the art.

To perform cauterization, after insertion of tool 240 through device 10 and positioning tool 240 distally so that cauterizing element 242 is exposed, cauterizing element 242 is contacted, or brought into close approximation with, tissue to be cauterized. Then cauterization energy is provided to cauterizing element 242, from an external power source, via electrical line 244. Cauterization energy may be applied, either continuously, or intermittently, until cauterization has been considered to have been successfully performed. Such consideration may be based on visual observation through device 10. Reapplication of cauterization energy may be performed, if necessary, as many times as necessary, in the manner described above, until a satisfactory cauterization has been achieved.

Figure 33:
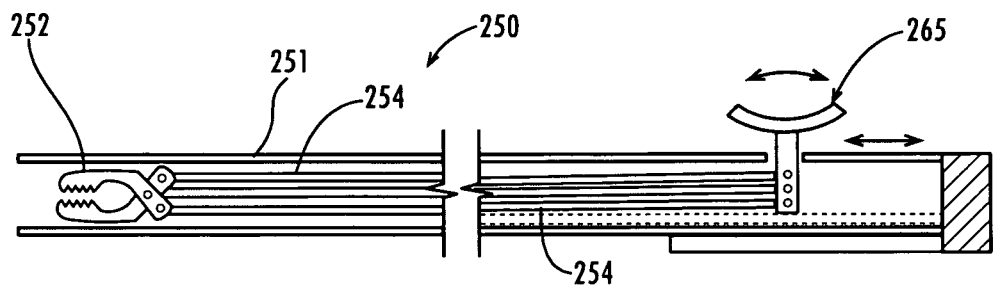
FIG. 33 illustrates graspers that may be used in a device described herein.

FIG. 33 illustrates graspers 250 that may be used with device 10 to grasp tissue in a reduced access surgical site. Graspers 250 are configured and dimensioned to be slid through either of the lumens 162 in device 10 of FIG. 23A for use therewith. Optionally, tool 250 may also be adapted to be delivered through a suction assembly or another catheter, for example.

In the example shown, tool 250 is provided with a long slender tube 251 having sufficient length to simultaneously extend from both distal and proximal openings of lumen 162 of device 10. Grasping jaws 252 are provided at a distal end portion of tool 250 and are connected to an actuator 256 located at a proximal end portion of tool 250, via linkage 254. When jaws 252 are in the retracted position, such as shown in FIG. 33, jaws 252 are concealed within the distal end portion of tube 251. This position is useful as tool 250 is advanced through lumen 162 or other catheter, to prevent jaws 252 from getting caught or jammed during translation of tool 250. Actuator 256 is slidably advanceable with respect to tube 251. Thus, by advancing actuator 256 distally with respect to tube 251, this extends grasping jaws 252 distally beyond the distal end of 252. This action is performed once the distal end of tube 252 has been placed near the target surgical area, such as by extending it beyond the distal end of lumen 162 in one example. Actuator 256 also rocks with respect to tube 251 to operate the opening and closing of jaws 252 via linkage 254.

Figure 34:
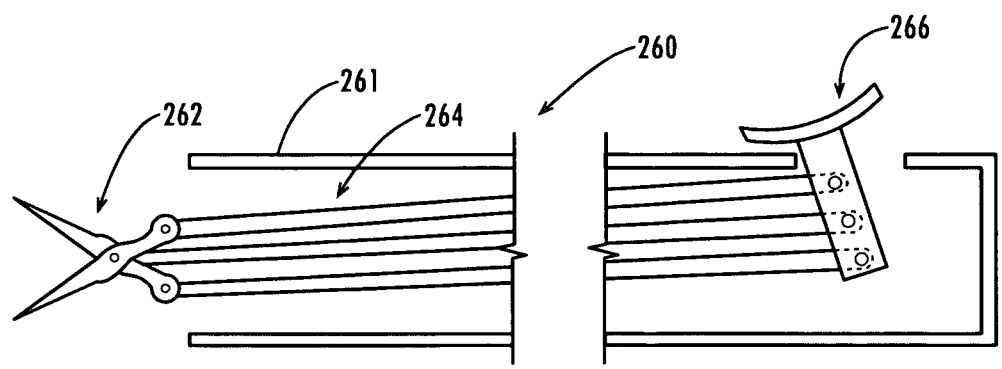
FIG. 34 illustrates scissors that may be used in a device described herein.

FIG. 34 illustrates scissors 260 that may be used with device 10 to cut tissue in a reduced access surgical site. Scissors 260 are configured and dimensioned to be slid through either of the lumens 162 in device 10 of FIG. 23A for use therewith. Optionally, scissors 260 may also be adapted to be delivered through a suction assembly or another catheter, for example.

In the example shown, tool 260 is configured similarly to graspers 250 described above with regard to FIG. 33. As such, only the differences at the distal end portion of the tool 260 and actuation thereof are described here. Scissor jaws 262 are provided at a distal end portion of tool 260 and are connected to an actuator 266 located at a proximal end portion of tool 260, via linkage 264. When scissor jaws 262 are in the retracted position, they are concealed within the distal end portion of tube 261. As shown in FIG. 34, scissor jaws 262 have been advanced distally beyond the distal end of tube 261, by sliding actuator 266 distally with respect to tube 261, so that scissor jaws 262 can be operated. Opening and closing of the scissor jaws in this example is controlled by rocking actuator 166. In FIG. 34, scissor jaws 262 have been opened by rocking actuator in the distal rotational direction.

Figure 35A:
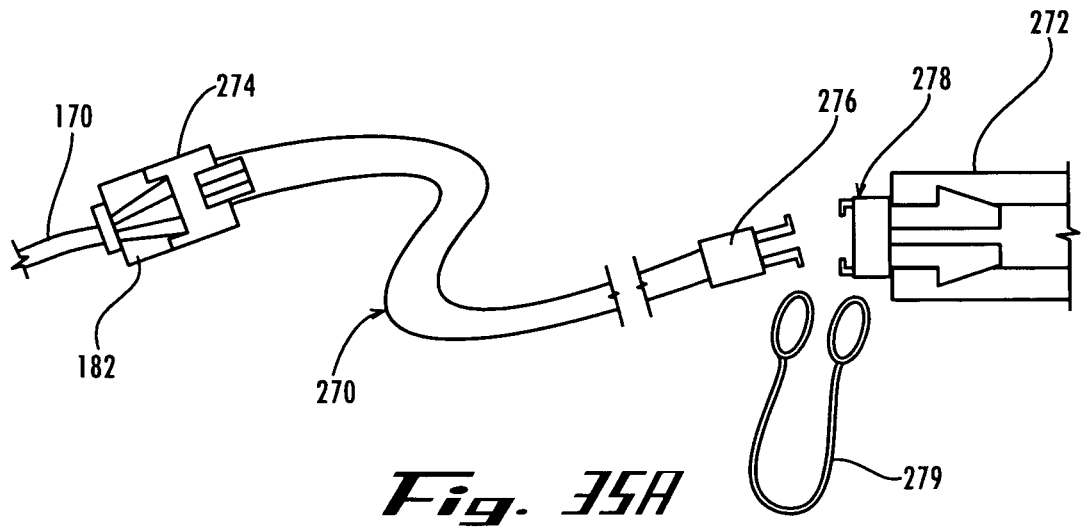
FIG. 35A illustrates an arrangement for minimizing side loading on a suction assembly during use with a device described herein, when the suction assembly is connected to a suction source.

The suction tubing provided in a typical operating room setting for the suction provided in the operating room is typically a fairly heavy gauge tubing relative to the tubing provided for suction assembly 170. Accordingly, side loading may be placed upon suction assembly 170 during use with device 10 when assembly 170 is connected to a suction source, due to the weight of the tubing connected to the suction source. One way of minimizing exposure to such loads is illustrated in FIG. 35A, where a length of tubing 270 that is lighter in gauge than the operating room suction tubing is provided as an extension tubing between suction assembly 170 and the operating room suction line 272. For example, tubing 270 may have an inside diameter of about 3/32 to 9/32 inches and an outside diameter of about 0.125 to about 0.375 inches, and may have a length of about two to five feet, typically about forty-two inches. A mating luer connector 274 is provided for connection with connector 182 of suction assembly 170 to provide fluid communication between tube 270 and tube 170. A barbed end connector 276 is provided at the proximal end to connect luer connector 278 at the proximal end of tube 270 with the suction line 272 for fluid communication therewith. This connection may then be fixed to a fixed structure on the operating table, such as a surgical drape for example, using a clamp 279, such as a towel clamp for example, while ensuring the slack is maintained in tube 270, so that any forces applied by tubing 272 to connection 276/278 are not transmitted to suction assembly 170.

Figure 35B:
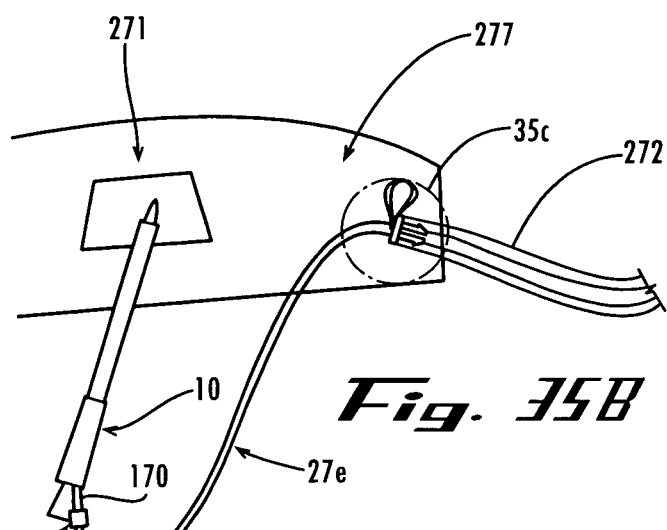
FIG. 35B illustrates an example of suction tube management wherein an extension tubing is in fluid communication with a suction assembly provided in a device that is configured to be used in surgical site.
Figure 35C:
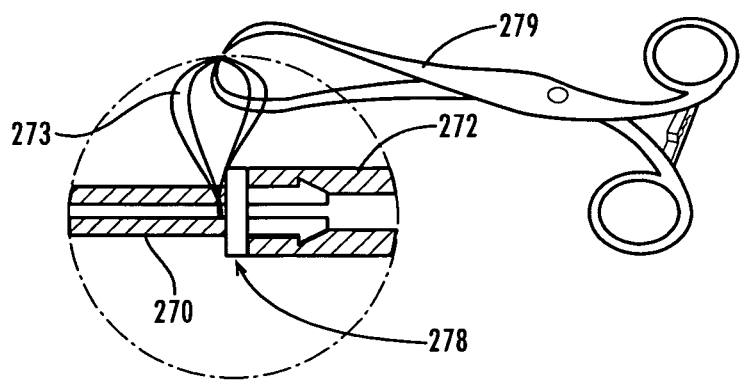
FIG. 35C illustrates a tether that is clamped to a surgical drape to accomplish the suction tube management described with regard to FIG. 35B.

FIG. 35B illustrates an example of suction tube management wherein extension tubing 270 is in fluid communication with suction assembly 170 provided in device 10 that is configured to be used in surgical site 271. In this arrangement, a tether 273 is provided at the proximal end of tubing 270 (which may be fixed to connector 278) and tether 273 is clamped to surgical drape 277 to accomplish the suction tube management, see the enlarged illustration of FIG. 35C.

Figure 36A:
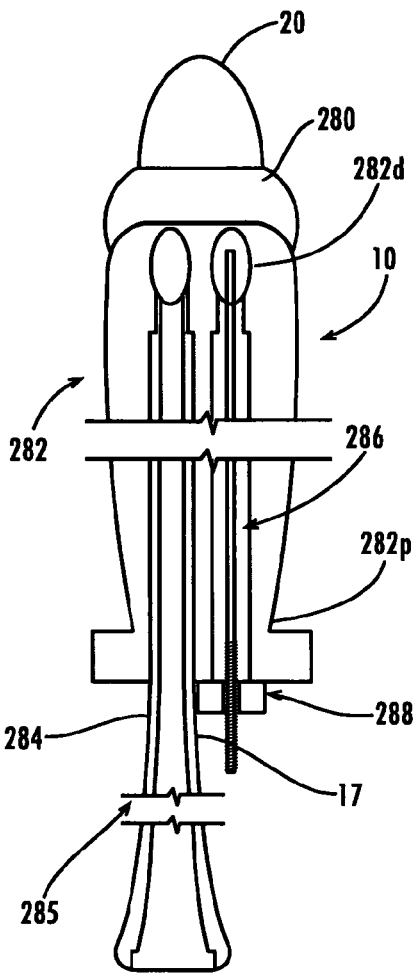
FIG. 36A shows another alternative arrangement of a device according to an embodiment of the present invention.

FIG. 36A shows another alternative arrangement of a device 10 according to the present invention. Although not all are shown in FIG. 36A, device 10 may include all of the features described above with regard to FIG. 23A. Additionally, device 10 is provided with an inflatable member 280, such as a toroidal balloon, or other shape, that is expandable around the base of the outside surface of tip 20 to achieve a temporary, atraumatic increase in the diameter at the distal end portion of device 10. This function can be used to support, reorient and help place the ablation device 50 in the surgical site. That is, the soft, atraumatic surface of the inflated member 280 can be pushed or pulled against the ablation device to reposition or reorient it, without significant risk of damaging tissues. Service port distal openings 278s, 278sn, if service ports are present, extend distally of inflatable member 280. Alternatively, inflatable member 280 can be expanded to facilitate the placement of other tools, such as snare assembly 30 or snare retrieval tool 100 or other tools described.

Figure 36B:
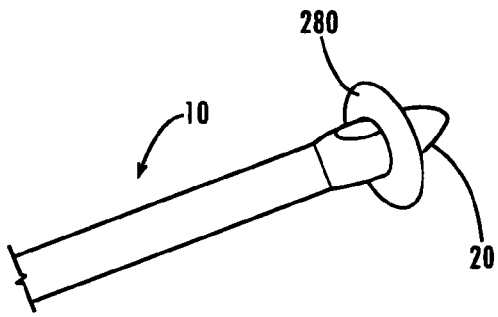
FIG. 36B illustrates the device of FIG. 36A with inflatable member inflated.
Figure 36C:
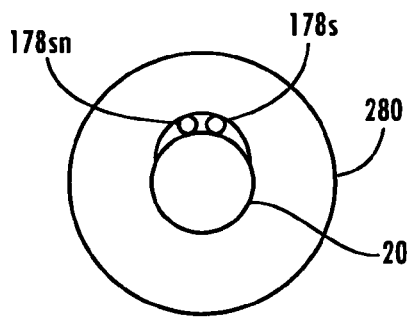
FIG. 36C shows an end view of the device shown in FIG. 36B.

FIG. 36B illustrates device 10 with inflatable member 280 inflated, and FIG. 36C shows an end view of device 10 of FIG. 36B. A fitting plug 282 is placed over shaft 17 of device 10 and is fixed to inflatable member 280 for holding inflatable member 280 in position over the proximal portion of tip 20. An inflation lumen 284 extends through fitting plug 282 and is in fluid communication with inflatable member 280. Fluid (isotonic saline, air or other fluid) is inputted through inflation port 285 under pressure to inflate inflatable member 285. A tensioning rod 286 interconnects the distal end portion 282d of fitting plug 282 to a proximal base portion 282p. Proximal base portion 282p is fixed with respect to tube 17 while distal end portion 282d can slide with respect thereto. A tensioning nut 288 is threaded over the proximal end portion of rod 286. When nut 288 is torqued to increase tension in rod 286, the distal portion 282d is drawn toward proximal portion 282p, drawing inflatable member 280 into position and maintaining it at the base of tip 20 as inflatable member expands.

Figure 37A:
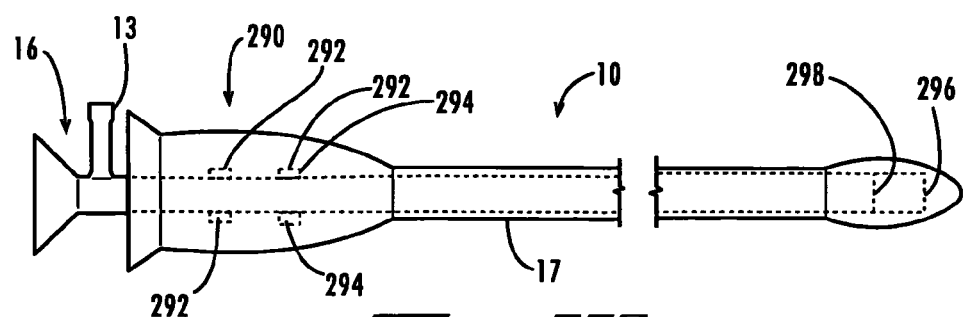
FIG. 37A illustrates a device with a positioning feature for positioning an endoscope at more that one predetermined location.

FIG. 37A illustrates a positioning feature for positioning endoscope 16 at more that one predetermined location. This feature may be employed with any of the devices 10 described herein. In this arrangement the proximal end portion of the lumen 162e into which the shaft of endoscope 16 is received may be provided with a wire form or other deflectable or spring loaded portion 290 including sockets 292 into which nubs, bumps or other protrusions 294 on the endoscope shaft 16 fits into when they are aligned with the sockets. In the example shown, endoscope can be placed into two predetermined locations longitudinally relative to tube 17 where protrusions 294-will snap into sockets 292. Note that this feature is not limited to two predetermined placement locations, as more can be added. Only two are shown for simplifying the drawing and explanation. In the position shown, protrusions are engaged in the more distal set of sockets 292 which positions the distal end of endoscope at position 296 for a close or more detailed field of view. Upon retracting endoscope 16 so that protrusions engage with the more proximal set of sockets 292, the distal end of endoscope 16 is positioned at location 298 to provide a wider field of view of the target.

Figure 37B:
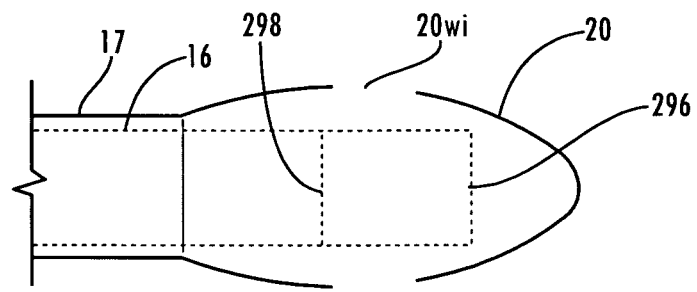
FIG. 37B illustrates a distal end portion of the device shown in FIG. 37A.

In addition to the ability to change the field of view of the endoscope with the above feature, an additional advantage may be provided when a tip 20 having one or more windows or openings 20wi is provided, as illustrated in FIG. 37B. In this instance, when tip 20 is in a liquid environment position 296 may be assumed, as little to no distortion occurs when viewing through the lens of tip 20. In a location where the environment of the tip is air, however, more distortion may be experienced. In this case, endoscope 16 can be retracted so that the distal tip of the endoscope assumes position 298, where viewing through the one or more openings 20wi can be performed to eliminate distortion.

Figure 37C:
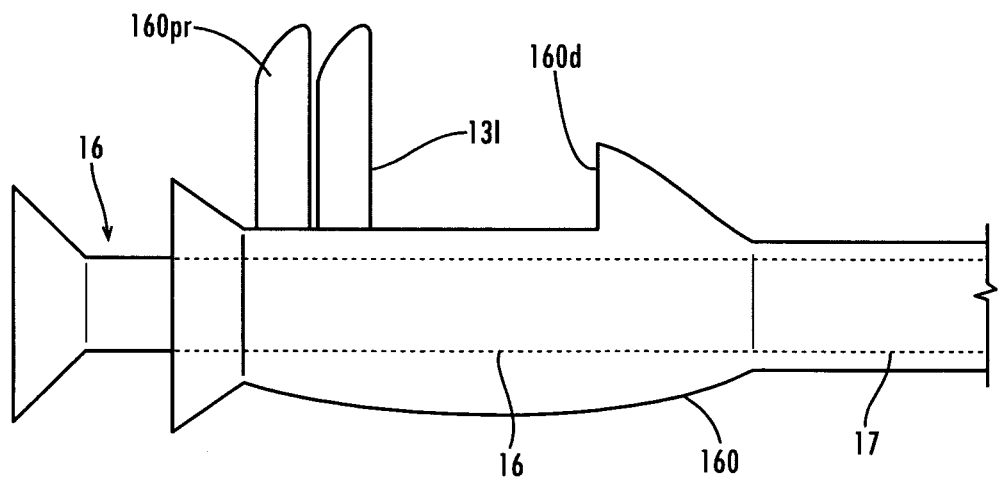
FIG. 37C illustrates an alternative arrangement that provides for placement of an endoscope in two different locations longitudinally relative to the tip of a device into which the endoscope is inserted.

FIG. 37C illustrates an alternative arrangement that provides for placement of endoscope in two different locations longitudinally relative to tip 20, wherein handle 160 is formed to include proximal and distal stops 160pr,160d. When endoscope 16 is positioned so that the light cable connector 131 abuts against proximal stop 160pr, as shown in FIG. 37C, then the distal end of endoscope 16 is placed at position 298, whereas when endoscope 16 is slid distally from this position to abut light cable connector 131 against distal stop 13d, then the distal end of endoscope 16 is placed at position 296.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A surgical system for performing minimally invasive surgical procedures, said system comprising:
an elongated body having a distal end portion, a proximal end portion, an external body surface, an interior region encompassed by the external body surface, and at least a first lumen and a second lumen extending at least partially through the interior region and generally along a direction of a longitudinal axis of said elongated body, wherein the first lumen is configured for receiving an endoscope therein; and
a lens having a bullet shaped configuration forming an elongated distal tip that extends distally with respect to said distal end portion of said elongated body,
wherein the elongated distal tip comprises a curved and blunt distal end allowing for blunt dissection of tissue and a sidewall extending from a proximal end of the elongated distal tip to the curved and blunt distal end that allows for viewing of the surgical field therethrough.

2. The system of claim 1, further comprising a handle attached to said proximal end portion of said elongated body.

3. The system of claim 2, further comprising a bell rotatably attached to said handle, wherein said bell is rotatable relative to said handle when said system is in an operative configuration.

4. The system of claim 1, wherein said elongated body is substantially rigid.

5. The system of claim 1, wherein the second lumen comprises a service port adapted to receive a tool other than an endoscope.

6. The system of claim 5, comprising two of said service ports.

7. The system of claim 5, wherein each said service port comprises a tube received within said elongated body.

8. The system of claim 7, wherein each said tube comprises a stainless steel hypotube.

9. The system of claim 1, further comprising an endoscope positioned in said lumen that is configured for receiving an endoscope therein.

10. The system of claim 7, wherein said distal tip further comprises at least one lumen therethrough, each said lumen of said distal tip being configured and dimensioned to receive one of said tubes therein and provide an exit opening for said service port through said distal tip.

11. The system of claim 1, further comprising a seal between said lens and a portion of said distal tip proximal to said lens.

12. The system of claim 7, wherein a proximal end portion of each said tube is securely held by a handle attached to said proximal end portion of said elongated body.

13. The system of claim 1, wherein said lens is removably mounted to a portion of said distal tip via mechanical connection.

14. The system of claim 13, wherein said lens is removably mounted to said portion of said distal tip via at least one of friction fitting and threads.

15. The system of claim 1, wherein said lens is fixed to a portion of said distal tip via adhesive.

16. The system of claim 1, wherein said distal tip is fixable to a distal end piece that includes at least one lumen, said distal end piece being mountable to said distal end portion of said elongated body, wherein said at least one lumen of said distal end piece aligns in communication with respective ones of at least one of said first and second lumens of said elongated body, in fluid communication therewith, to function as at least one service port.

17. The system of claim 1, wherein said distal end comprises a protrusion extending distally from a distal end portion of said distal tip, said distal end portion comprising a curved surface converging toward a longitudinal axis of said distal tip.

18. The system of claim 1, further comprising a snare device extending through said second lumen, said snare device having a snare on a distal end thereof.

19. The system of claim 18, wherein said snare device further comprises a snare on a proximal end thereof.

20. The system of claim 2, wherein said handle comprises an open proximal end configured to receive an endoscope therethrough.

21. The system of claim 2, wherein said handle captures said proximal end portion of said elongated body, thereby preventing axial movement of said elongated body with respect to said handle.

22. The system of claim 2, wherein said handle allows rotation of said elongated body with respect to said handle.

23. The system of claim 2, wherein said handle prevents rotation of said elongated body with respect to said handle.

24. The system of claim 2, wherein a recess is provided in a portion of said handle, said recess being configured and dimensioned to receive a light cable that extends from an endoscope, when said endoscope is received in said elongated body.

25. The system of claim 1, further comprising an insert mounted within said elongated body, wherein said insert and said elongated body cooperate to define said first and second lumens, said first and second lumens each being defined by a surface of said elongated body and a surface of said insert, respectively.

26. The system of claim 25, wherein said insert forms a friction fit with said elongated body within said elongated body.

27. The system of claim 25, further comprising a second insert, interchangeable with said first insert, wherein said second insert and said elongated body cooperate to form lumens having at least one of: a different size, different relative positioning and different number of lumens relative to size, positioning and number of said first and second lumens formed in cooperation between said elongated main body and said insert.

28. The system of claim 10, further comprising a second tip that is interchangeable with said distal tip, said second tip comprising at least one of: a different size, different relative positioning and different number of lumens relative to size, positioning and number of said at least one lumen formed in said distal tip.

29. The system of claim 1, wherein said distal tip is axially aligned with said first lumen, and wherein said second lumen is not configured for receiving said endoscope therein and is positioned radially outwardly from said first lumen, such that an implement can be delivered though said second lumen and a distal end portion of said implement is deliverable alongside said distal tip.

30. The system of claim 1, further comprising a suction luer in fluid communication with one of said first and second lumens and extending from said proximal end portion of said elongated body.

31. The system of claim 1, further comprising an introducer tube in fluid communication with one of said first and second lumens and extending from said proximal end portion of said elongated body.

32. The system of claim 30, wherein said elongated body comprises three lumens, said system further including an introducer tube in fluid communication with a lumen other than said lumen configured and adapted to receive an endoscope and said lumen in fluid communication with said suction luer, said introducer extending from said proximal end portion of said elongated body.

33. The system of claim 1, wherein said distal tip is releasably attachable to said elongated body.

34. The system of claim 1, further comprising a suction tube extending through one of said first and second lumens and providing fluid communication between said distal and proximal end portions of said elongated body.

35. The system of claim 1, further comprising a suction tube extending through one of said first and second lumens and providing fluid communication between said distal tip and said proximal end portion of said elongated body.

36. The system of claim 1, wherein said distal tip comprises an inner stop configured to prevent distal advancement of a distal end of said endoscope therepast, to establish an offset between the distal end of said distal tip and a distal end of said endoscope.

37. The system of claim 1, wherein said lens comprises an outer lens, said distal tip further comprising an inner tapered lens configured to break up reflections when viewing through said endoscope.

38. The system of claim 1, wherein said distal end portion of said elongated body has a first cross-sectional area and said proximal end portion of said elongated body has a second cross-sectional area, said second cross-sectional area being greater than said first cross-sectional area.

39. The system of claim 1, wherein said distal end portion of said elongated body is teardrop-shaped in cross-section.

40. The system of claim 39, wherein said proximal end portion of said elongated body is circular in cross-section.

41. The system of claim 1, wherein said lumens are formed by metal tubes within said elongated tubular body.

42. The system of claim 1, further comprising a retrieval hook tool extending through one of said first and second lumens, said retrieval hook tool comprising a hook at a distal end thereof.

43. The system of claim 1, further comprising a perforation tool extending through one of said first and second lumens, said perforation tool comprising a needle or barbed needle at a distal end thereof, said needle or barbed needle being extendable distally of said distal end portion of said elongated body.

44. The system of claim 43, wherein said perforation tool further comprises a cutter blade, said barbed needle being retractable proximally to draw tissue engaged by said barb needle into contact with said cutter blade.

45. The system of claim 1, further comprising a perforation tool extending through one of said first and second lumens, said perforation tool comprising graspers adapted to be extended distally to grasp tissue; and a cutter blade, said graspers being retractable proximally to draw tissue engaged by said graspers into contact with said cutter blade.

46. The system of claim 1, further comprising a perforation tool extending through one of said first and second lumens, said perforation tool comprising a cork screw adapted to be extended distally to engage tissue; and a cutter blade, said corkscrew being retractable proximally to draw tissue engaged by said corkscrew into contact with said cutter blade.

47. The system of claim 1, further comprising a perforation tool extending through one of said first and second lumens, said perforation tool comprising a spike configured to pierce through tissue upon an impulsive impact; and a plunger type actuator located on a proximal end portion of said perforation tool.

48. The system of claim 1, further comprising a mapping probe tool extending through one of said first and second lumens, said mapping probe tool comprising at least a pair of mapping elements on a distal end portion thereof, said mapping elements being extendable distally of a distal opening of said lumen.

49. The system of claim 48, wherein said distal end portion of said mapping probe tool is bent at an angle to a longitudinal axis of a remainder of said mapping probe tool when said mapping probe tool is in an unbiased state.

50. The system of claim 48, wherein said distal end portion of said mapping probe tool is formed in a Y-shape when in an unbiased state, one of said mapping elements being located on one arm of the Y-shape and a second of said mapping elements being located on an arm opposite said one arm.

51. The system of claim 1, further comprising a linear ablating probe tool extending through one of said first and second lumens, said linear ablating probe tool comprising a linear ablation element on a distal end portion thereof.

52. The system of claim 1, further comprising a point ablation probe tool extending through one of said first and second lumens, said point ablation probe tool comprising an ablation probe point on a distal tip thereof.

53. The system of claim 1, further comprising a cautery tool extending through one of said first and second lumens, said cautery tool comprising a cauterizing element on a distal end portion thereof.

54. The system of claim 1, further comprising graspers extending through one of said first and second lumens, said graspers comprising a tube having sufficient length to simultaneously extend from both distal and proximal openings of said lumen, grasping jaws provided at a distal end portion of said graspers, and an actuator located at a proximal end portion of said graspers, said actuator linked to said grasping jaws for operation thereof.

55. The system of claim 1, further comprising scissors extending through one of said first and second lumens, said scissors comprising a tube having sufficient length to simultaneously extend from both distal and proximal openings of said lumen, scissor jaws provided at a distal end portion of said scissors, and an actuator located at a proximal end portion of said scissors, said actuator linked to said scissor jaws for operation thereof.

56. The system of claim 1, further comprising an inflatable member that is expandable around a base of said distal tip to achieve a temporary, atraumatic increase in diameter at a distal end portion of said system.

57. The system of claim 56, further comprising a fitting plug positioned over said elongated body and fixed to said inflatable member for holding said inflatable member in position over said base of said distal tip.

58. The system of claim 57, further comprising a tensioning member interconnecting said fitting plug and said inflatable member, said tensioning member being adjustable to draw said inflatable member into a desired position at said base of said distal tip.

59. The system of claim 1, wherein said first lumen comprises a positioning feature for positioning the endoscope at more than one predetermined location.

60. The system of claim 59, wherein said positioning feature comprises biased sockets configured to receive protrusions on the endoscope therein.

61. The system of claim 1, wherein said distal tip includes at least one window proximal of a distal end of said distal tip, through which viewing by the endoscope is permitted.

62. The system of claim 2, wherein said handle includes proximal and distal stops so that when said endoscope is inserted in said first lumen, a light cable of said endoscope abuts said proximal stop for placing said endoscope in one predetermined location relative to said elongated body, and abuts said distal stop for placing said endoscope in a second location relative to said elongated body.

63. The system of claim 1, wherein the elongated body further comprises a semi-flexible sleeve having distal and proximal sleeve end portions and wherein the elongated distal tip is rigid and attachable to a distal end of the elongated body therethrough.

64. The system of claim 63, wherein said sleeve is sufficiently flexible to navigate around pulmonary veins to at least partially encircle the pulmonary veins and said sleeve is sufficiently rigid so that a proximal portion of said sleeve outside of a patient can be pushed on to advance said distal end portion of said sleeve within the patient.

65. The system of claim 63, further comprising an endoscope inserted in said sleeve, said endoscope having a flexible or malleable shaft and being positioned for viewing through said distal tip.

66. The system of claim 63, wherein said distal tip comprises at least one port in fluid communication with said at least one lumen in said elongated body.

67. The system of claim 1, wherein the elongated body further comprises a semi-flexible sleeve having distal and proximal sleeve end portions, and wherein the system further comprises a capturing feature extending distally from a distal end of the elongated body.

68. The system of claim 67, further comprising an endoscope inserted in said sleeve, the endoscope having a distal tip attached thereto that extends distally of the distal end of the elongated body.

69. The system of claim 68, wherein said capturing feature comprises a snare threaded through openings in the distal tip to extend distally therefrom.

70. The system of claim 69, wherein the elongated body is slidable proximally with respect to the distal tip to cinch down the snare.

71. The system of claim 67, wherein the capturing feature comprises a pad of either a hook or a loop portion of a hook and loop type fastening mechanism.

72. The system of claim 67, wherein the capturing feature comprises a magnet.

73. The system of claim 1, wherein the second lumen comprises a slot opening to an external surface of the elongated body, and wherein the slot is configured and dimensioned to releasably secure a tool therein via friction fit.

74. The system of claim 73, wherein the tool comprises a snare catheter.

75. The system of claim 73, wherein the lens that is alignable with one of the first lumen that is configured for receiving an endoscope therein.

76. The system of claim 73, wherein the slot extends over a majority of a length of said elongated body.

77. The system device of claim 73, wherein the slot is formed in an eyelet on the distal end portion of the elongated body.

78. The system device of claim 77, wherein the tool includes a distal end portion having a first outside diameter larger than an outside diameter of a portion of the tool immediately proximal of the distal end portion of the tool, wherein the portion immediately proximal is slidable through the slot, and wherein retraction of the tool being positioned through the slot and into the lumen that the slot opens to, secures the distal end portion in the eyelet.

79. The system of claim 73, wherein the slot is formed by a keyed socket on the distal end portion of the elongated member.

80. The system device of claim 73, wherein the second lumen having the slot is asymmetrical in cross-section and forms a cam surface permitting the tool to be rotated into the second lumen.

81. The system of claim 1, further comprising:
an endoscope having an elongated shaft having distal and proximal end portions, wherein the distal tip is attachable to the distal end portion of the endoscope; and
a ring provided over the elongated shaft of the endoscope and axially slidable with respect thereto, the ring being configured and dimensioned to releasably fix a distal end portion of a tool thereto.

82. The system of claim 81, wherein said ring comprises a releasable locking mechanism.

83. The system of claim 81, wherein said tool comprises a snare catheter.

84. The system of claim 1, wherein the elongated body is configured and dimensioned to apply suction through the elongated distal tip attachable to said distal end portion, wherein the elongated distal tip has a proximal opening having an outside diameter that is greater than an outside diameter of the distal end of the elongated body, such that a gap is formed between the elongated distal tip and the elongated body when the elongated distal tip is attached to the aid elongated body, facilitating diffuse application of suction.

85. The system of claim 84, further comprising struts interconnecting said distal tip and said elongated body.

86. The system of claim 1, further comprising a routing snare tool configured and dimensioned to be slid through the second lumen of the elongated body, wherein the routing snare tool comprises
a flexible outer tube having sufficient column strength to advance the tool through the second lumen by pushing on a proximal portion of said outer tube from a location outside of the second lumen, to advance said tube without buckling;
a snare line having a length greater than a length of said flexible outer tube; and
a snare loop fixed to an end of said snare line via heat shrink tubing.

87. The system of claim 86, wherein the routing snare tool further comprises a second snare loop fixed to an opposite end of said snare line via heat shrink tubing.

88. The system of claim 87, wherein both ends of said outer tube are chamfered.

89. The system of claim 87, wherein said heat shrink tubing is color coded differently with respect to each snare loop to facilitate ready visual distinction between the two snare loops.

90. The system of claim 86, wherein said snare loop comprises a kink extending distally from a remainder of said snare loop.

91. The system of claim 86, wherein said snare loop is angled, with respect to a longitudinal axis of said snare line, by an angle of less than about thirty degrees.

92. The system of claim 86, further comprising a lock configured to fix a position of said snare line relative to said outer tube to maintain said snare loop in a cinched configuration.

93. The system of claim 92, wherein said lock comprises an actuator configured to move a clamp into contact with said snare line.

94. The system of claim 92, wherein said lock comprises a pair of locking clasps that are alternatively lockable and releasable by the same actuating movement by a user.

95. The system of claim 1, further comprising a capture tool configured and dimensioned to be slid through the second lumen of the elongated body, wherein the snare capture tool comprises
an elongated mandrel configured and dimensioned to be slid through the second lumen;
a handle fixed to a proximal end of said mandrel; and
a ball fixed at a distal end of said mandrel.

96. The system of claim 95, further comprising a polymeric layer formed over a majority of said mandrel, wherein a distal end portion of said mandrel extends from a distal end of said polymeric layer and is not covered thereby.

97. The system of claim 96, further comprising a compressible spring over said layer, a proximal end portion of said spring abutting said handle, said spring having an outside diameter larger than an inside diameter of said second lumen, thereby being prevented from insertion into said second lumen.

98. The system of claim 97, wherein said snare capture tool is configured and dimensioned, so that when said spring is compressed against a proximal end of the second lumen by advancing said handle distally with respect to said second lumen, said ball and at least a portion of said distal end portion not covered by said polymeric layer extend distally from a distal end of said second lumen, and when a driving force is released from said handle, said spring expands, thereby retracting said ball and said at least a portion of said distal end portion not covered by said polymeric layer into said second lumen.

99. The system of claim 1, further comprising a retrieval hook tool configured and dimensioned to be slid through the second lumen of the elongated body, wherein the retrieval hook tool comprises
an elongated mandrel configured and dimensioned to be slid through the second lumen;
a handle fixed to a proximal end of said mandrel; and
a hook provided at a distal end of said mandrel.

100. The system of claim 99, wherein the retrieval hook tool further comprises a polymeric layer formed over a majority of said mandrel, wherein a distal end portion of said mandrel extends from a distal end of said polymeric layer and is not covered thereby.

101. The system of claim 99, wherein the retrieval hook further comprises a compressible spring over said mandrel, a proximal end portion of said spring abutting said handle, said spring having aria outside diameter larger than an inside diameter of said second lumen, thereby being prevented from insertion into said second lumen.

102. The system of claim 101, wherein said retrieval hook tool is configured and dimensioned, so that when said spring is compressed against a proximal end of the second lumen by advancing said handle distally with respect to the second lumen, said hook extends distally from a distal end of the second lumen, and when a driving force is released from said handle, said spring expands, thereby retracting said hook into the second lumen.

103. The system of claim 100, wherein said mandrel is offset in said polymeric layer, such that longitudinal axes of said mandrel and said polymeric layer do not coincide.

104. The system of claim 1, further comprising a bolo tool configured and dimensioned to be slid through the second lumen of the elongated body, wherein the bolo tool comprises
    an elongated mandrel configured and dimensioned to be slid through the second lumen;
    a first ball provided at a proximal end of said mandrel; and
    a second ball provided at a distal end of said mandrel.

105. The system of claim 1, further comprising a trigger snare tool configured and dimensioned to be slid through the second lumen of the elongated body, wherein the trigger snare tool comprises
    an elongated mandrel configured and dimensioned to be slid through the second lumen;
    a snare provided at a distal end of said mandrel; and
    a snare guide into which said elongated mandrel is slidably received, said snare guide being configured and dimensioned to be slid through the second lumen, wherein said snare guide is slidable distally with respect to said mandrel to cinch down said snare.

106. The system of claim 105, wherein the trigger snare tool further comprises
    a handle provided at a proximal end of said mandrel;
    a trigger slidably positioned over said handle and fixed to a proximal end of said snare guide; and
    a biasing member that biases said trigger distally from said handle.

107. The system of claim 105, wherein said snare, when uncinched, is oriented at an acute angle with respect to a longitudinal axis of said mandrel.

108. The system of claim 1, further comprising a perforation tool configured and dimensioned to be slid through the second lumen of the elongated body, wherein the perforation tool comprises
    a perforating member connected to an actuator via an elongated shaft;
    a sheath configured and dimensioned to be slid through the second lumen of the elongated body and to surround said perforating member and said shaft during sliding within the second lumen;
    said actuator being operable to slide said perforating member distally with respect to said sheath to extend said perforating member distally beyond a distal end of said sheath.

109. The system of claim 108, wherein said perforating member comprises a needle.

110. The system of claim 108, wherein said perforating member comprises a spike.

111. The system of claim 108, wherein the perforation tool further comprises a handle mounted to a proximal portion of the perforation tool, said handle configured to be mated with a connector of a suction assembly.

112. The system of claim 108, wherein the perforation tool further comprises a cutting blade positioned proximally of said perforating member, said perforating member being configured to engage tissue, wherein said actuator is actuatable to retract said perforating member, after engaging tissue, to draw the tissue against said cutting blade, thereby cutting an opening through the tissue.

113. The system of claim 112, wherein the perforation tool further comprises a second actuator, said second actuator being linked to said cutting blade and operable to rotate said cutting blade.

114. The system of claim 112, wherein said perforating member comprises a barbed needle.

115. The system of claim 112, wherein said perforating member comprises a corkscrew.

116. The system of claim 112, wherein said perforating member comprises graspers.

117. The system of claim 116, wherein said actuator is further actuatable to open and close said graspers.

118. The system of claim 1, further comprising a mapping probe tool configured and dimensioned to be slid through the second lumen of the elongated body, wherein the mapping probe tool comprises
    an elongated member configured and dimensioned to be positioned in the second lumen and having a length sufficient to extend a proximal end portion of said elongated member from the proximal end of the second lumen while a distal end portion extends distally from a distal end of the second lumen;
    said distal end portion including at least a pair of probe mapping elements, said probe mapping elements being electrically connectable to a power source located proximally of the mapping probe tool via at least one electrical wire connected thereto.

119. The system of claim 118, wherein the mapping probe tool further comprises
    a handle fixed to a proximal end portion of said elongated member; and
    a biasing member configured to bias said handle away from the second lumen, said biasing member being configured and dimensioned to prevent insertion of said biasing member into the second lumen.

120. The system of claim 119, wherein said probe mapping tool is configured and dimensioned, so that when said handle is slid distally with respect to the second lumen, thereby biasing the biasing member, said probe mapping elements extend distally from a distal end of the second lumen, and when a driving force is released from said handle, said biasing member drives said handle proximally with respect to the second lumen, thereby retracting said probe mapping elements into the second lumen.

121. The system of claim 118, wherein said distal end portion is Y-shaped in an unbiased configuration, with one of each said pair of probes being located on opposite ones of open arms of said Y-shape.

122. The system of claim 118, wherein said distal end portion is angled to a longitudinal axis of a remainder of said elongated member when said elongated member is in an unbiased configuration.

123. The system of claim 1, further comprising a ablating probe tool configured and dimensioned to be slid through the second lumen of the elongated body, wherein the linear ablating probe tool comprises
    an elongated member configured and dimensioned to be positioned in the second lumen and having a length sufficient to extend a proximal end portion of said elongated member from the proximal end of the second lumen while a distal end portion extends distally from a distal end of the second lumen;
    a linear ablation member located at the distal end portion of said elongated member and configured to form a linearly extending lesion in tissue being treated thereby; and
    at least one ablation conduit connected to said linear ablation member and extending from said linear ablation member to a proximal end portion of said elongated member, a proximal end of each said ablation conduit being configured to be connected to a source of ablation energy located proximally of said tool.

124. The system of claim 123, wherein the linear ablating probe tool further comprises an actuator located on said proximal end portion of said elongated member, said actuator being operable by a user to deliver ablation energy to said linear ablation member.

125. The system of claim 123, wherein the linear ablating probe tool further comprises
a handle fixed to a proximal end portion of said elongated member; and
a biasing member configured to bias said handle away from the second lumen, said biasing member being configured and dimensioned to prevent insertion of said biasing member into the second lumen.

126. The system of claim 125, wherein said linear ablating probe tool is configured and dimensioned, so that when said handle is slid distally with respect to the second lumen, thereby biasing the biasing member, said linear ablation member extends distally from a distal end of the second lumen, and when a driving force is released from said handle, said biasing member drives said handle proximally with respect to the second lumen, thereby retracting said linear ablation member into the second lumen.

127. The system of claim 1, further comprising a ablation probe tool configured and dimensioned to be slid through the second lumen of the elongated body, wherein the point ablation probe tool comprises
an elongated member configured and dimensioned to be positioned in the second lumen and having a length sufficient to extend a proximal end portion of said elongated member from the proximal end of the second lumen while a distal end portion extends distally from a distal end of the second lumen;
an ablation probe point provided on a distal end of said elongated member and configured to form a point lesion in tissue being treated thereby; and
an ablation conduit connected to said ablation probe point and extending from said ablation probe point to a proximal end portion of said elongated member, a proximal end of said ablation conduit being configured to be connected to a source of ablation energy located proximally of said point ablation probe tool.

128. The system of claim 127, wherein the point ablation probe tool further comprises an actuator located on said proximal end portion of said elongated member, said actuator being operable by a user to deliver ablation energy to said ablation probe point.

129. The system of claim 127, wherein the point ablation probe tool further comprises
a handle fixed to a proximal end portion of said elongated member; and
a biasing member configured to bias said handle away from the second lumen, said biasing member being configured and dimensioned to prevent insertion of said biasing member into the second lumen.

130. The system of claim 129, wherein said point ablation probe tool is configured and dimensioned, so that when said handle is slid distally with respect to the second lumen, thereby biasing the biasing member, said ablation probe point extends distally from a distal end of the second lumen, and when a driving force is released from said handle, said biasing member drives said handle proximally with respect to the second lumen, thereby retracting said ablation probe point into the second lumen.

131. The system of claim 1, further comprising a cautery tool configured and dimensioned to be slid through the second lumen of the elongated body, wherein the cautery tool comprises
an elongated member configured and dimensioned to be positioned in the second lumen and having a length sufficient to extend a proximal end portion of said elongated member from the proximal end of the second lumen while a distal end portion extends distally from a distal end of the second lumen;
a cauterizing element provided on a distal end of said elongated member and configured to cauterize tissue; and
an electrical wire connected to said cauterizing element and extending from said cauterizing element to a proximal end portion of said elongated member, a proximal end of said electrical wire being configured to be connected to a power source located proximally of said cautery tool.

132. The system of claim 131, wherein the cautery tool further comprises an actuator located on said proximal end portion of said elongated member, said actuator being operable by a user to deliver energy to said cauterizing element.

133. The system of claim 131, wherein the cautery tool further comprises
a handle fixed to a proximal end portion of said elongated member; and
a biasing member configured to bias said handle away from the second lumen, said biasing member being configured and dimensioned to prevent insertion of said biasing member into the second lumen.

134. The system of claim 133, wherein said cautery tool is configured and dimensioned, so that when said handle is slid distally with respect to the second lumen, thereby biasing the biasing member, said cauterizing element extends distally from a distal end of the second lumen, and when a driving force is released from said handle, said biasing member drives said handle proximally with respect to the second lumen, thereby retracting said cauterizing element into the second lumen.

135. The system of claim 1, further comprising a graspers tool configured and dimensioned to be slid through the second lumen of the elongated body, wherein the graspers tool comprises
grasping jaws connected to an actuator via an elongated linkage;
a sheath configured and dimensioned to be slid through the second lumen of the elongated body and to surround said grasping jaws and said linkage during sliding within the second lumen;
said actuator being operable to slide said grasping jaws distally with respect to said sheath to extend said grasping jaws distally beyond a distal end of said sheath.

136. The system of claim 135, wherein said actuator is further actuatable to open and close said grasping jaws.

137. The system of claim 1, further comprising a scissors tool configured and dimensioned to be slid through the second lumen of the elongated body, wherein the scissors tool comprises
scissors jaws connected to an actuator via an elongated linkage;
a sheath configured and dimensioned to be slid through the second lumen of the elongated body and to surround said scissors jaws and said linkage during sliding within the second lumen;

said actuator being operable to slide said scissors jaws distally with respect to said sheath to extend said scissors jaws distally beyond a distal end of said sheath.

138. The system of claim 137, wherein said actuator is further actuatable to open and close said scissors jaws.

139. The system of claim 1, wherein the curved and blunt distal end is curved in a direction of the longitudinal axis of the distal tip to allow for blunt dissection.

140. The system of claim 1, wherein the distal tip is configured to provide an endoscopic field of view allowing for visibility of tissue from the distal tip proximal end to a location distal thereto.

141. The system of claim 1, wherein the distal tip is configured to allow for an endoscopic field of view along a length of the distal tip.

142. The system of claim 1, wherein the distal tip has a parabolic profile.

143. The system of claim 1, wherein the distal tip is radially symmetric about its longitudinal axis.

144. The system of claim 1, wherein a length of the distal tip is as least as large as the maximum width of the distal tip.

145. A surgical system for performing minimally invasive surgical procedures, said system comprising:
   a first elongated body having a distal end portion, a proximal end portion, an external body surface, an interior region encompassed by the exterior body surface, and at least one lumen extending at least partially through said interior region and generally along a direction of a longitudinal axis of said first elongated body and configured and dimensioned for receiving an endoscope therein;
   a second elongated body aligned substantially parallel with, external to and side-by-side of said first elongated body, said first elongated body also being external to said second elongated body, said second elongated body having distal and proximal end portions and at least one lumen extending generally along a direction of a longitudinal axis of said second elongated body and configured and dimensioned for receiving a tool other than said endoscope therein; and
   a lens having a bullet shaped configuration forming an elongated distal tip that is attachable to said distal end portion of said first elongated body, said distal tip comprising a curved and blunt distal end that encloses said distal end portion of said first elongated body when attached thereto for blunt dissection of tissue, and wherein a sidewall of the distal tip extending from a proximal end of the distal tip to the curved and blunt distal allows for visualization of a surgical field therethrough.

146. The system of claim 145, further comprising an endoscope positioned in said lumen that is configured and dimensioned for receiving an endoscope therein.

147. The system of claim 145, further comprising a handle attached to said proximal end portion of said first elongated body.

148. The system of claim 145, wherein said first and second elongated bodies are substantially rigid.

149. The system of claim 145, wherein said second elongated body is fixed externally to said first elongated body.

150. The system of claim 149, wherein said second elongated body is welded to said first elongated body.

151. The system of claim 145, further comprising a snare device extending through one of said at least one lumen of said second elongated body, said snare device having a snare on a distal end thereof.

152. The system of claim 15, wherein said snare device further comprises a snare on a proximal end thereof.

153. The system of claim 146, wherein said distal tip is attached to said distal end portion of said first elongated body, and wherein a distal end of said endoscope is positionable within said distal tip.

154. The system of claim 145, wherein said distal tip comprises a notch configured and dimensioned to receive a portion of a snare therein.

155. The system of claim 145, further comprising a tool other than an endoscope extending through one of said at least one lumens of said second elongated body.

156. The system of claim 155, wherein said tool is selected from the group consisting of: suction tool, snare capture tool, retrieval hook tool, bolo tool, trigger snare tool, perforation tool, mapping probe tool, linear ablating probe tool, point ablation probe tool, cautery tool, graspers tool, and scissors tool.

157. The system of claim 145, wherein the bullet shaped configuration of the elongated distal tip has a parabolic profile.

158. The system of claim 157, wherein when the elongated distal tip is attached to the elongated body, the elongated distal tip is longitudinally offset with respect to a distal opening of the second lumen such that the curved and blunt distal end extends distally beyond the opening.

159. The system of claim 145, wherein when the elongated distal tip is attached to the elongated body, the elongated distal tip is longitudinally offset with respect to a distal opening of the second lumen such that the curved and blunt distal end extends distally beyond the opening.

160. A minimally invasive method of routing a flexible tool around an internal structure in a patient's body, said method comprising the steps of:
   (a) inserting a device including an endoscope through a small opening in the patient and advancing the device to position a distal end of the device into a surgical space in which the internal structure resides, wherein the device comprises a surgical system for performing minimally invasive surgical procedures, wherein the system includes
      an elongated body having a distal end portion, a proximal end portion, an external body surface, an interior region encompassed by the external body surface, and at least a first lumen and a second lumen extending at least partially through the interior region and generally along a direction of a longitudinal axis of said elongated body, wherein the first lumen is configured for receiving the endoscope therein; and
      a lens having a bullet shaped configuration forming an elongated distal tip that extends distally with respect to said distal end portion of said elongated body, wherein the elongated distal tip comprises a curved and blunt distal end allowing for blunt dissection of tissue and a sidewall extending from a proximal end of the elongated distal tip to the curved and blunt distal end that allows for viewing of the surgical field therethrough;
   (b) inserting the flexible member through a service port in the device and extending a distal end portion of the flexible member distally of the second lumen of the elongated body joined by the service port;
   (c) visually confirming the distal end portion via the endoscope;
   (d) removing the device from the patient via the small opening while maintaining the flexible member in the patient, substantially in the current position of the flexible member;

(e) inserting the device through a second small opening in the patient and advancing the device to position the distal end of the device into the surgical space in which the internal structure resides, on a side of the internal structure opposite to the side in which the flexible member is placed;

(f) connecting the distal end of the device with the distal end portion of the flexible member; and (g) removing the device from the patient via the second small opening, thereby drawing the flexible member around the internal structure.

161. The method of claim 160, further comprising advancing the distal end of the flexible member partially around the internal structure after said removing the device from the patient via the small opening while maintaining the flexible member in the patient, substantially in the current position of the flexible member.

162. The method of claim 160, further comprising visualizing the distal end of the flexible member through the endoscope to align the device with the flexible member to perform said connecting step.

163. The method of claim 160, wherein the distal end of the flexible member comprises a snare loop and said connecting comprises cinching the snare loop over a distal end portion of the device.

164. The method of claim 160, further comprising fixing an ablation device to the proximal end of said flexible member and further advancing the flexible member by drawing the flexible member out of the second opening, thereby routing the ablation device around the internal structure.

165. The method of claim 160, wherein the internal structure comprises a plurality of pulmonary veins.

166. The method of claim 164, further comprising ablating tissue along a pathway defined by the ablation device around the internal structure.

167. The method of claim 160, wherein the distal end of the flexible member comprises a ball and said connecting comprises inserting a retrieval hook tool through a service port of the device, extending a hook of the retrieval hook tool distally of a distal end of a lumen that is in fluid communication with the service port, and hooking the distal end portion of the flexible member with the hook.

168. The method of claim 160, wherein the distal end of the flexible member comprises a snare loop and said connecting comprises inserting a retrieval hook tool through a service port of the device, extending a hook of the retrieval hook tool distally of a distal end of a lumen that is in fluid communication with the service port, and hooking the snare loop with the hook.

169. The method of claim 160, wherein the distal end of the flexible member comprises a ball and said connecting comprises inserting a trigger snare tool through a service port of the device, extending a snare of the trigger snare tool distally of a distal end of a lumen that is in fluid communication with the service port, and snaring the distal end portion of the flexible member by cinching down the snare loop after placing the snare loop over the ball.

170. The method of claim 160, further comprising:

after said inserting the through a small opening in the patient and prior to said advancing the device to position a distal end of the device into a surgical space in which the internal structure resides, perforating at least one tissue layer to establish a pathway for said advancing.

171. The method of claim 170, wherein said perforating comprises inserting a perforating tool through a service port of the device, extending a perforating member distally of a distal end of the second lumen that is in fluid communication with the service port and into contact with tissue to be perforated, and perforating the tissue.

172. The method of claim 170, wherein said perforating comprises inserting a perforating tool through a service port of the device, extending a perforating member distally of a distal end of the second lumen that is in fluid communication with the service port and into contact with tissue to be perforated, grasping the tissue and retracting the grasped tissue against a cutting blade, thereby perforating the tissue.

173. The method of claim 166, further comprising reinserting the device into at least one of said first and second openings, advancing the distal end of the device toward the internal structure, and visually inspecting at least a portion of the lesion formed around the internal structure via the endoscope.

174. The method of claim 166, further comprising reinserting the device into at least one of said first and second openings, advancing the distal end of the device toward the internal structure, inserting a mapping probe tool through a service port in the device, extending mapping probe elements distally of a distal opening of a lumen in fluid connection with said service port, contacting tissue on opposite sides of a lesion formed by said ablating with at least one mapping probe on each side of the lesion, and measuring sufficiency of the lesion formed with the mapping probe tool.

175. A minimally invasive method of routing a flexible tool around an internal structure in a patient's body, said method comprising the steps of:

(a) inserting a device including an endoscope through a small opening in the patient and advancing the device to position a distal end of the device into a surgical space in which the internal structure resides, wherein the device comprises a surgical system for performing minimally invasive surgical procedures, wherein the system includes an elongated body having a distal end portion, a proximal end portion, an external body surface, an interior region encompassed by the external body surface, and at least a first lumen and a second lumen extending at least partially through the interior region and generally along a direction of a longitudinal axis of said elongated body, wherein the first lumen is configured for receiving the endoscope therein; and a lens having a bullet shaped configuration forming an elongated distal tip that extends distally with respect to said distal end portion of said elongated, body, wherein the elongated distal tip comprises a curved and blunt distal end allowing for blunt dissection of tissue and a sidewall extending from a proximal end of the elongated distal tip to the curved and blunt distal end that allows for viewing of the surgical field therethrough;

(b) inserting the flexible member through a service port in the device and extending a distal end portion of the flexible member distally of the second lumen of the elongated body joined by the service port;

(c) visually confirming the distal end portion via the endoscope;

(d) retracting the device to remove the flexible member from a distal end of the second lumen, while maintaining the flexible member in the patient, substantially in the current position of the flexible member;

(e) distally advancing the device into patient to position the distal end of the device into the surgical space in which the internal structure resides, on a side of the internal structure opposite to the side in which the flexible member is placed;

(f) connecting the distal end of the device with the distal end portion of the flexible member; and (g) removing the device from the patient via the small opening, thereby drawing the flexible member around the internal structure.

176. The method of claim 175, further comprising advancing the distal end of the flexible member partially around the internal structure after removing the flexible member from the device while maintaining the flexible member in the patient, substantially in the current position of the flexible member.

177. The method of claim 175, further comprising fixing an ablation device to the proximal end of said flexible member and further advancing the flexible member by drawing the flexible member out of the opening, thereby routing the ablation device around the internal structure.

178. The method of claim 177, further comprising ablating tissue along a pathway defined by the ablation device around the internal structure.

179. A minimally invasive method of routing a flexible tool around an internal structure in a patient's body, said method comprising the steps of:

(a) inserting a device including an endoscope and a semi-flexible sheath slid over the endoscope through a small opening in the patient and advancing the device to position a distal end of the device into a surgical space in which the internal structure resides, the semi-flexible sheath including a rigid, transparent distal end that allows viewing therethrough via the endoscope, wherein the device comprises a surgical system for performing minimally invasive surgical procedures, wherein the system includes an elongated body having a distal end portion, a proximal end portion, an external body surface, an interior region encompassed by the external body surface, and at least a first lumen and a second lumen extending at least partially through the interior region and generally along a direction of a longitudinal axis of said elongated body, wherein the first lumen is configured for receiving the endoscope therein, and wherein the semi-flexible sheath forms the elongated body; and a lens having a bullet shaped configuration forming an elongated distal tip at the transparent distal end that extends distally with respect to said distal end portion of said elongated body, wherein the elongated distal tip comprises a curved and blunt distal end allowing for blunt dissection of tissue and a sidewall extending from a proximal end of the elongated distal tip to the curved and blunt distal end that allows for viewing of the surgical field therethrough;

(b) visually confirming placement of a distal end of the semi-flexible member via the endoscope;

(c) removing the endoscope from the patient via the small opening while maintaining the semi-flexible member and rigid distal end in the patient, substantially in the current position of the semi-flexible member and rigid distal end;

(d) inserting the endoscope through a second small opening in the patient and advancing the endoscope to position the distal end thereof into the surgical space in which the internal structure resides, on a side of the internal structure opposite to the side in which the semi-flexible member is placed;

(e) connecting the distal end of the endoscope with the distal end of the semi-flexible member; and (f) removing the endoscope from the patient via the second small opening, thereby drawing the semi-flexible member around the internal structure.

180. The method of claim 179, further comprising advancing the distal end of the semi-flexible member partially around the internal structure after said removing the endoscope from the patient via the small opening while maintaining the semi-flexible member in the patient, substantially in the current position of the flexible member.

181. The method of claim 179, further comprising visualizing the distal end of the flexible member through the endoscope to align the device with the flexible member to perform said connecting step.

182. The method of claim 179, further comprising sliding a sleeve having a distal tip over the endoscope prior to said inserting the endoscope through a second small opening.

183. The method of claim 182, wherein the sleeve comprises a snare loop extending from the distal tip, the snare loop being threaded through a distal tip and the distal tip being mounted to the endoscope.

184. The method of claim 183, wherein said connecting comprises cinching the snare loop around the distal end of the semi-flexible member.

185. The method of claim 184, wherein said cinching is performed by sliding the sleeve proximally with respect to the endoscope.

186. The method of claim 179, further comprising fixing an ablation device to the proximal end of the semi-flexible member and further advancing the semi-flexible member by drawing the semi-flexible member out of the second opening, thereby routing the ablation device around the internal structure.

187. The method of claim 186, further comprising ablating tissue along a pathway defined by the ablation device around the internal structure.

188. A method of performing rapid exchange of tools in a device while performing a minimally invasive surgical procedure, said method comprising the steps of:

(a) inserting a device having at least and an endoscope and a first tool received therein, through a small opening in the patient and advancing the device to position a distal end of the device into a reduced-access surgical space, wherein the device comprises a surgical system for performing minimally invasive surgical procedures, wherein the system includes an elongated body having a distal end portion, a proximal end portion, an external body surface, an interior region encompassed by the external body surface, and at least a first lumen and a second lumen extending at least partially through the interior region and generally along a direction of a longitudinal axis of said elongated body, wherein the first lumen is configured for receiving the endoscope therein and the second lumen is configured for receiving the first tool therein; and a lens having a bullet shaped configuration forming an elongated distal tip that extends distally with respect to said distal end portion of said elongated body, wherein the elongated distal tip comprises a curved and blunt distal end allowing for blunt dissection of tissue and a sidewall extending from a proximal end of the elongated distal tip to the curved and blunt distal end that allows for viewing of the surgical field therethrough;

(b) removing the first tool from the device, while maintaining the device and the endoscope in the surgical space; and (c) inserting a second tool into the device, thereby replacing the tool having been removed.

189. The method of claim 188, wherein said removing comprises removing the first tool through a slot opening to an external surface of the device from the second lumen in the device.

190. The method of claim 188, wherein the first tool comprises a snare catheter.

191. The method of claim 188, wherein said removing comprises removing the first tool from an eyelet on a distal end portion of said device.

192. The method of claim 189, wherein the second lumen from which the slot opens is asymmetrical in cross-section and forms a cam surface permitting a second tool to be rotated into the lumen.

193. The method of claim 188, wherein said device comprises a ring provided over an elongated shaft of the endoscope and axially slidable with respect thereto, and wherein said removing comprises releasing said first tool from said ring.

194. A method of relieving side loading by an operating room suction tubing on a device in fluid communication with the operating room suction tubing, said method comprising:
(a) connecting a distal end of a length of first tubing to a suction assembly of a device to be used to apply suction, wherein the length of first tubing has proximal and distal ends and has a lighter gauge than a gauge of the operating room suction tubing, wherein the device is a surgical system for performing minimally invasive surgical procedures, wherein the system includes
an elongated body having a distal end portion, a proximal end portion, an external body surface, an interior region encompassed by the external body surface, and at least a first lumen and a second lumen extending at least partially through the interior region and generally along a direction of a longitudinal axis of said elongated body, wherein the first lumen is configured for receiving the endoscope therein; and
a lens having a bullet shaped configuration forming an elongated distal tip that extends distally with respect to said distal end portion of said elongated body, wherein the elongated distal tip comprises a curved and blunt distal end allowing for blunt dissection of tissue and a sidewall extending from a proximal end of the elongated distal tip to the curved and blunt distal end that allows for viewing of the surgical field therethrough; and
(b) connecting the proximal end of said length of first tubing to the operating room suction tubing, thereby putting the suction assembly of the device in fluid communication with the operating room suction tubing.

195. The method of claim 194, further comprising clamping the length of first tubing to a support.

196. The method of claim 195, wherein the length of first tubing comprises a tether extending therefrom, and said clamping comprises clamping said tether to the support.

197. A tool for relieving side loading on a device in fluid communication with an operating room suction tube, wherein the device is a surgical system for performing minimally invasive surgical procedures, wherein the system includes
an elongated body having a distal end portion, a proximal end portion, an external body surface, an interior region encompassed by the external body surface, and at least a first lumen and a second lumen extending at least partially through the interior region and generally along a direction of a longitudinal axis of said elongated body, wherein the first lumen is configured for receiving the endoscope therein; and
a lens having a bullet shaped configuration forming an elongated distal tip that extends distally with respect to said distal end portion of said elongated body, wherein the elongated distal tip comprises a curved and blunt distal end allowing for blunt dissection of tissue and a sidewall extending from a proximal end of the elongated distal tip to the curved and blunt distal end that allows for viewing of the surgical field therethrough, said tool comprising:
a length of first tubing having a lighter gauge than a gauge of the operating room suction tubing, said length of first tubing having proximal and distal ends;
a first connector at a distal end of said first length of tubing configured and dimensioned to be connected to a suction assembly of the device, to establish fluid communication between the suction assembly and the length of first tubing;
a second connector at a proximal end of said length of first tubing configured and dimensioned to be connected to the operating room suction tube, to establish fluid communication between the operating room suction tube and the length of first tubing; and
a tether extending from the length of first tubing, said tether adapted to be clamped to a support.

* * * * *

UNITED STATES PATENT AND TRADEMARK OFFICE
CERTIFICATE OF CORRECTION

PATENT NO.        : 8,932,208 B2
APPLICATION NO.   : 11/544897
DATED             : January 13, 2015
INVENTOR(S)       : Amar Kendale et al.

Page 1 of 1

It is certified that error appears in the above-identified patent and that said Letters Patent is hereby corrected as shown below:

In the Claims

Claim 145, column 65, line 48, change "distal allows for visualization" to --distal end allows for visualization--

Signed and Sealed this
Twenty-second Day of December, 2015

Michelle K. Lee
*Director of the United States Patent and Trademark Office*